United States Patent
Abbate

(10) Patent No.: US 11,484,693 B2
(45) Date of Patent: *Nov. 1, 2022

(54) EXPANDABLE DEVICES AND METHODS FOR TREATING A NASAL OR SINUS CONDITION

(71) Applicant: Intersect ENT, Inc., Menlo Park, CA (US)

(72) Inventor: Anthony J. Abbate, Santa Clara, CA (US)

(73) Assignee: Intersect ENT, Inc., Menlo Park, CA (US)

( * ) Notice: Subject to any disclaimer, the term of this patent is extended or adjusted under 35 U.S.C. 154(b) by 605 days.

This patent is subject to a terminal disclaimer.

(21) Appl. No.: 16/432,187

(22) Filed: Jun. 5, 2019

(65) Prior Publication Data

US 2019/0314622 A1    Oct. 17, 2019

Related U.S. Application Data

(63) Continuation of application No. 12/779,240, filed on May 13, 2010, now Pat. No. 10,357,640.

(Continued)

(51) Int. Cl.
*A61F 2/82* (2013.01)
*A61F 2/18* (2006.01)
(Continued)

(52) U.S. Cl.
CPC ............. *A61M 31/00* (2013.01); *A61F 2/186* (2013.01); *A61F 5/08* (2013.01); *A61K 9/0043* (2013.01);
(Continued)

(58) Field of Classification Search
CPC .......... A61F 2/186; A61F 2/82; A61F 2/0105; A61F 2/01; A61F 5/08; A61M 2210/0618; A61K 9/0043
See application file for complete search history.

(56) References Cited

U.S. PATENT DOCUMENTS 374,026 A     11/1887  Williams
2,009,393 A    7/1935  Failla
(Continued)

FOREIGN PATENT DOCUMENTS

| AU | 2008/201495 A1 | 10/2008 |
|---|---|---|
| CN | 101189016 A | 5/2008 |
| DE | 101 05 592 A1 | 8/2002 |
| EP | 0 096 941 B1 | 9/1986 |

(Continued)

OTHER PUBLICATIONS

Becker, D.G. (2003). "The Minimally Invasive, Endoscopic Approach to Sinus Surgery," *Journal of Long-Term Effects of Medical Implants* 13(3):207-221.

(Continued)

*Primary Examiner* — Katherine M Rodjom
(74) *Attorney, Agent, or Firm* — Carter, DeLuca & Farrell LLP

(57) ABSTRACT

Described here are expandable devices and methods for using them. The devices generally comprise a hub and a plurality of legs extending therefrom. In some variations, the hub may comprise one or more domed portions, tapered portions, or the like. The legs may comprise one or more straight segments, one or more curved segments, or a combination thereof. The devices may comprise one or more polymers, and/or one or more portions of the device may be configured to biodegrade. In other variations, the device may be configured to release one or more drugs therefrom. Additionally, in some variations the devices may be configured to be self-expandable from a low-profile configuration to an expanded configuration.

20 Claims, 20 Drawing Sheets

Related U.S. Application Data

(60) Provisional application No. 61/178,896, filed on May 15, 2009.

(51) Int. Cl.
| | | |
|---|---|---|
| *A61M 31/00* | | (2006.01) |
| *A61F 5/08* | | (2006.01) |
| *A61K 9/00* | | (2006.01) |
| *A61B 6/00* | | (2006.01) |
| *A61M 25/00* | | (2006.01) |
| *A61F 2/01* | | (2006.01) |

(52) U.S. Cl.
CPC .......... *A61M 31/002* (2013.01); *A61B 6/481* (2013.01); *A61F 2/0105* (2020.05); *A61F 2/82* (2013.01); *A61M 25/00* (2013.01)

(56) References Cited

U.S. PATENT DOCUMENTS

| | | |
|---|---|---|
| 2,096,162 A | 10/1937 | Daley |
| 2,691,985 A | 10/1954 | Newsom |
| 3,049,125 A | 8/1962 | Kriwkowitsch |
| 3,473,165 A | 10/1969 | Gran et al. |
| 3,502,078 A | 3/1970 | Hill et al. |
| 3,517,128 A | 6/1970 | Hines |
| 3,570,494 A | 3/1971 | Gottschalk |
| 3,583,391 A | 6/1971 | Cox et al. |
| 3,766,924 A | 10/1973 | Pidgeon |
| 3,800,788 A | 4/1974 | White |
| 3,828,577 A | 8/1974 | Haynes |
| 3,894,539 A | 7/1975 | Tallent |
| 3,903,893 A | 9/1975 | Scheer |
| 3,913,584 A | 10/1975 | Walchle et al. |
| 4,094,303 A | 6/1978 | Johnston |
| 4,245,652 A | 1/1981 | Kelly et al. |
| 4,389,208 A | 6/1983 | LeVeen et al. |
| 4,419,095 A | 12/1983 | Nebergall et al. |
| D276,937 S | 12/1984 | Griggs |
| 4,534,761 A | 8/1985 | Raible |
| 4,580,568 A | 4/1986 | Gianturco |
| 4,604,920 A | 8/1986 | Dupke |
| 4,627,971 A | 12/1986 | Ayer |
| 4,650,488 A | 3/1987 | Bays et al. |
| 4,655,771 A | 4/1987 | Listen |
| 4,704,126 A | 11/1987 | Baswell et al. |
| 4,737,141 A | 4/1988 | Spits |
| 4,744,792 A | 5/1988 | Sander et al. |
| 4,753,636 A | 6/1988 | Free |
| 4,886,493 A | 12/1989 | Yee |
| 4,941,881 A | 7/1990 | Masters et al. |
| 4,964,850 A | 10/1990 | Bouton et al. |
| 5,000,957 A | 3/1991 | Eckenhoff et al. |
| 5,011,474 A | 4/1991 | Brennan |
| 5,035,706 A | 7/1991 | Giantureo et al. |
| 5,062,829 A | 11/1991 | Pryor et al. |
| 5,108,418 A | 4/1992 | Lefebvre |
| 5,116,311 A | 5/1992 | Löfstedt |
| 5,139,502 A | 8/1992 | Berg et al. |
| 5,139,510 A | 8/1992 | Goldsmith, III et al. |
| 5,139,832 A | 8/1992 | Hayashi et al. |
| 5,167,614 A | 12/1992 | Tessmann et al. |
| 5,189,110 A | 2/1993 | Ikematu et al. |
| 5,217,484 A | 6/1993 | Marks |
| 5,246,455 A | 9/1993 | Shikani |
| 5,256,146 A | 10/1993 | Ensminger et al. |
| 5,300,119 A | 4/1994 | Blom |
| 5,312,813 A | 5/1994 | Costerton et al. |
| 5,324,304 A | 6/1994 | Rasmussen |
| 5,336,163 A | 8/1994 | DeMane et al. |
| 5,342,296 A | 8/1994 | Persson et al. |
| 5,344,427 A | 9/1994 | Cottenceau et al. |
| 5,348,553 A | 9/1994 | Whitney |
| 5,350,580 A | 9/1994 | Muchow et al. |
| 5,391,179 A | 2/1995 | Mezzoli |
| 5,443,498 A | 8/1995 | Fontaine |
| 5,501,700 A | 3/1996 | Hirata |
| 5,507,210 A | 4/1996 | Paramest |
| 5,507,807 A | 4/1996 | Shippert |
| 5,512,055 A | 4/1996 | Domb et al. |
| 5,538,738 A | 7/1996 | Ritter et al. |
| 5,540,712 A | 7/1996 | Kleshinski et al. |
| 5,556,413 A | 9/1996 | Lam |
| 5,632,762 A | 5/1997 | Myler |
| 5,634,942 A | 6/1997 | Chevillon et al. |
| 5,645,584 A | 7/1997 | Suyama |
| 5,664,567 A | 9/1997 | Linder |
| 5,669,933 A | 9/1997 | Simon et al. |
| 5,672,179 A | 9/1997 | Garth et al. |
| 5,693,065 A | 12/1997 | Rains, III |
| 5,713,855 A | 2/1998 | Shippert |
| 5,725,525 A | 3/1998 | Kordis |
| 5,746,224 A | 5/1998 | Edwards |
| 5,749,921 A | 5/1998 | Lenker et al. |
| 5,792,100 A | 8/1998 | Shantha |
| 5,800,379 A | 9/1998 | Edwards |
| 5,800,429 A | 9/1998 | Edwards |
| 5,827,224 A | 10/1998 | Shippert |
| 5,895,408 A | 4/1999 | Pagan |
| 5,899,878 A | 5/1999 | Glassman |
| 5,928,190 A | 7/1999 | Davis |
| 5,931,852 A | 8/1999 | Brennan |
| 5,968,071 A | 10/1999 | Chevillon et al. |
| 5,992,000 A | 11/1999 | Humphrey et al. |
| 6,033,436 A | 3/2000 | Steinke et al. |
| 6,054,122 A | 4/2000 | MacPhee et al. |
| 6,063,102 A | 5/2000 | Morales |
| 6,074,381 A | 6/2000 | Dinh et al. |
| 6,082,990 A | 7/2000 | Jackson et al. |
| 6,092,273 A | 7/2000 | Villareal |
| 6,092,528 A | 7/2000 | Edwards |
| 6,108,886 A | 8/2000 | Kimes et al. |
| 6,113,641 A | 9/2000 | Leroy et al. |
| 6,123,697 A | 9/2000 | Shippert |
| 6,149,681 A | 11/2000 | Houser et al. |
| 6,149,944 A | 11/2000 | Jeong et al. |
| 6,152,946 A | 11/2000 | Broome et al. |
| 6,180,848 B1 | 1/2001 | Flament et al. |
| 6,190,353 B1 | 2/2001 | Makower et al. |
| 6,195,225 B1 | 2/2001 | Komatsu et al. |
| 6,200,335 B1 | 3/2001 | Igaki |
| 6,217,600 B1 | 4/2001 | DiMatteo |
| 6,224,626 B1 | 5/2001 | Steinke |
| 6,228,111 B1 | 5/2001 | Tormala et al. |
| 6,280,413 B1 | 8/2001 | Clark et al. |
| 6,290,728 B1 | 9/2001 | Phelps et al. |
| 6,297,227 B1 | 10/2001 | Johnson |
| 6,302,875 B1 | 10/2001 | Makower et al. |
| 6,306,084 B1 | 10/2001 | Pinczower |
| 6,329,386 B1 | 12/2001 | Mollison |
| 6,342,068 B1 | 1/2002 | Thompson |
| 6,347,241 B2 | 2/2002 | Burbank et al. |
| 6,350,465 B1 | 2/2002 | Jonnalagadda et al. |
| 6,352,547 B1 | 3/2002 | Brown et al. |
| 6,355,032 B1 | 3/2002 | Hovda et al. |
| 6,375,615 B1 | 4/2002 | Flaherty et al. |
| 6,386,197 B1 | 5/2002 | Miller |
| 6,398,758 B1 | 6/2002 | Jacobsen et al. |
| 6,447,530 B1 | 9/2002 | Ostrovsky et al. |
| 6,447,539 B1 | 9/2002 | Nelson et al. |
| 6,468,290 B1 | 10/2002 | Weldon et al. |
| 6,491,940 B1 | 12/2002 | Levin |
| 6,524,608 B2 | 2/2003 | Ottoboni et al. |
| 6,537,294 B1 | 3/2003 | Boyle et al. |
| 6,543,452 B1 | 4/2003 | Lavigne |
| 6,544,230 B1 | 4/2003 | Flaherty et al. |
| 6,555,566 B2 | 4/2003 | Ponikau |
| 6,562,058 B2 | 5/2003 | Seguin et al. |
| 6,565,597 B1 | 5/2003 | Fearnot et al. |
| 6,589,286 B1 | 7/2003 | Litner |
| 6,605,294 B2 | 8/2003 | Sawhney |
| 6,606,995 B1 | 8/2003 | Sadek et al. |
| 6,618,921 B1 | 9/2003 | Thornton |
| 6,685,648 B2 | 2/2004 | Flaherty et al. |

(56) References Cited

U.S. PATENT DOCUMENTS

| | | |
|---|---|---|
| 6,692,455 B2 | 2/2004 | Goode et al. |
| 6,695,856 B2 | 2/2004 | Kieturakis et al. |
| 6,709,465 B2 | 3/2004 | Mitchell et al. |
| 6,712,859 B2 | 3/2004 | Rousseau et al. |
| 6,715,485 B1 | 4/2004 | Djupesland |
| 6,719,934 B2 | 4/2004 | Stinson |
| 6,746,426 B1 | 6/2004 | Flaherty et al. |
| 6,749,617 B1 | 6/2004 | Palasis et al. |
| 6,884,260 B2 | 4/2005 | Kugler et al. |
| 6,942,690 B1 | 9/2005 | Pollock et al. |
| 6,945,992 B2 | 9/2005 | Goodson, IV et al. |
| 6,951,053 B2 | 10/2005 | Padilla et al. |
| 6,966,923 B2 | 11/2005 | Gittings |
| 7,018,401 B1 | 3/2006 | Hyodoh et al. |
| 7,072,720 B2 | 7/2006 | Puskas |
| 7,074,426 B2 | 7/2006 | Kochinke |
| 7,108,706 B2 | 9/2006 | Hogle |
| RE39,321 E | 10/2006 | MacPhee et al. |
| 7,179,275 B2 | 2/2007 | McGuckin, Jr. et al. |
| 7,195,016 B2 | 3/2007 | Loyd et al. |
| 7,225,518 B2 | 6/2007 | Eidenschink et al. |
| 7,235,099 B1 | 6/2007 | Duncavage et al. |
| 7,249,390 B2 | 7/2007 | Yale et al. |
| RE39,923 E | 11/2007 | Blom |
| 7,314,484 B2 | 1/2008 | Deem et al. |
| 7,316,147 B2 | 1/2008 | Perreault et al. |
| 7,361,168 B2 | 4/2008 | Makower et al. |
| 7,410,480 B2 | 8/2008 | Muni et al. |
| 7,419,497 B2 | 9/2008 | Muni et al. |
| 7,451,765 B2 | 11/2008 | Adler |
| 7,462,175 B2 | 12/2008 | Chang et al. |
| 7,476,648 B1 | 1/2009 | Tabata et al. |
| 7,500,971 B2 | 3/2009 | Chang et al. |
| 7,520,876 B2 | 4/2009 | Ressemann et al. |
| 7,544,192 B2 | 6/2009 | Eaton et al. |
| 7,559,925 B2 | 7/2009 | Goldfarb et al. |
| 7,641,644 B2 | 1/2010 | Chang et al. |
| 7,641,688 B2 | 1/2010 | Lesh |
| 7,645,272 B2 | 1/2010 | Chang et al. |
| 7,651,696 B2 | 1/2010 | Bates |
| 7,654,997 B2 | 2/2010 | Makower et al. |
| 7,658,758 B2 | 2/2010 | Diaz et al. |
| 7,658,764 B2 | 2/2010 | Reitan et al. |
| 7,662,141 B2 | 2/2010 | Eaton et al. |
| 7,662,142 B2 | 2/2010 | Eaton et al. |
| 7,686,798 B2 | 3/2010 | Eaton et al. |
| 7,691,094 B2 | 4/2010 | Eaton et al. |
| 7,713,255 B2 | 5/2010 | Eaton et al. |
| 7,717,933 B2 | 5/2010 | Becker |
| 7,740,642 B2 | 6/2010 | Becker |
| 7,753,929 B2 | 7/2010 | Becker |
| 7,771,482 B1 | 8/2010 | Karmon |
| 7,951,130 B2 | 5/2011 | Eaton et al. |
| 7,951,131 B2 | 5/2011 | Eaton et al. |
| 7,951,132 B2 | 5/2011 | Eaton et al. |
| 7,951,133 B2 | 5/2011 | Eaton et al. |
| 7,951,134 B2 | 5/2011 | Eaton et al. |
| 7,951,135 B2 | 5/2011 | Eaton et al. |
| 8,007,470 B2 | 8/2011 | Shirley et al. |
| 8,025,635 B2 | 9/2011 | Eaton et al. |
| 8,088,120 B2 | 1/2012 | Worsoff |
| 8,109,918 B2 | 2/2012 | Eaton et al. |
| 8,192,450 B2 | 6/2012 | Gonzales et al. |
| 8,197,433 B2 | 6/2012 | Cohen |
| 8,303,640 B2 | 11/2012 | Hepworth et al. |
| 8,337,454 B2 | 12/2012 | Eaton et al. |
| 8,500,776 B2 | 8/2013 | Ebner |
| 8,535,707 B2 | 9/2013 | Arensdorf et al. |
| 8,585,730 B2 | 11/2013 | Eaton et al. |
| 8,585,731 B2 | 11/2013 | Abbate et al. |
| 8,585,753 B2 | 11/2013 | Scanlon et al. |
| 8,721,591 B2 | 5/2014 | Chang et al. |
| 8,740,839 B2 | 6/2014 | Eaton et al. |
| 8,740,929 B2 | 6/2014 | Gopferich et al. |
| 8,763,222 B2 | 7/2014 | Abbate et al. |
| 8,802,131 B2 | 8/2014 | Arensdorf et al. |
| 8,858,974 B2 | 10/2014 | Eaton et al. |
| 8,986,341 B2 | 3/2015 | Abbate et al. |
| 9,585,681 B2 | 3/2017 | Eaton et al. |
| 9,782,283 B2 | 10/2017 | Abbate et al. |
| 10,010,651 B2 | 7/2018 | Eaton et al. |
| 10,232,152 B2 | 3/2019 | Abbate |
| 10,357,640 B2 * | 7/2019 | Abbate ................ A61M 31/00 |
| 10,406,332 B2 | 9/2019 | Abbate |
| 2001/0021871 A1 | 9/2001 | Stinson |
| 2002/0022048 A1 | 2/2002 | Bromberg |
| 2002/0051793 A1 | 5/2002 | Drabick |
| 2002/0051845 A1 | 5/2002 | Mehta et al. |
| 2002/0077693 A1 | 6/2002 | Barclay et al. |
| 2002/0111603 A1 | 8/2002 | Cheikh |
| 2002/0143387 A1 | 10/2002 | Soetikno et al. |
| 2002/0188344 A1 | 12/2002 | Bolea et al. |
| 2002/0198586 A1 | 12/2002 | Inoue |
| 2003/0033001 A1 | 2/2003 | Igaki |
| 2003/0040772 A1 | 2/2003 | Hyodoh et al. |
| 2003/0040790 A1 | 2/2003 | Furst |
| 2003/0055488 A1 | 3/2003 | Igaki |
| 2003/0064965 A1 | 3/2003 | Richter |
| 2003/0065346 A1 | 4/2003 | Evens et al. |
| 2003/0070682 A1 | 4/2003 | Wilson et al. |
| 2003/0105469 A1 | 6/2003 | Karmon |
| 2003/0133877 A1 | 7/2003 | Levin |
| 2003/0135266 A1 | 7/2003 | Chew et al. |
| 2003/0135268 A1 | 7/2003 | Desai |
| 2003/0135970 A1 | 7/2003 | Thornton |
| 2003/0147954 A1 | 8/2003 | Yang et al. |
| 2003/0157187 A1 | 8/2003 | Hunter |
| 2003/0158598 A1 | 8/2003 | Ashton |
| 2003/0195459 A1 | 10/2003 | Shippert |
| 2003/0203030 A1 | 10/2003 | Ashton et al. |
| 2003/0209835 A1 | 11/2003 | Chun et al. |
| 2003/0236570 A1 | 12/2003 | Cook et al. |
| 2004/0043052 A1 | 3/2004 | Hunter et al. |
| 2004/0064083 A1 | 4/2004 | Becker |
| 2004/0064150 A1 | 4/2004 | Becker |
| 2004/0073284 A1 | 4/2004 | Bates |
| 2004/0073299 A1 | 4/2004 | Hudson |
| 2004/0093062 A1 | 5/2004 | Glastra |
| 2004/0116958 A1 | 6/2004 | Gopferich et al. |
| 2004/0117004 A1 | 6/2004 | Osborne et al. |
| 2004/0133270 A1 | 7/2004 | Grandt |
| 2004/0176827 A1 | 9/2004 | Jacobson et al. |
| 2004/0236415 A1 | 11/2004 | Thomas |
| 2005/0038497 A1 | 2/2005 | Neuendorf et al. |
| 2005/0043706 A1 | 2/2005 | Eaton et al. |
| 2005/0043783 A1 | 2/2005 | Amis et al. |
| 2005/0055045 A1 | 3/2005 | DeVries et al. |
| 2005/0119725 A1 | 6/2005 | Wang et al. |
| 2005/0124560 A1 | 6/2005 | Sung et al. |
| 2005/0131460 A1 | 6/2005 | Gilford |
| 2005/0131514 A1 | 6/2005 | Hijlkema et al. |
| 2005/0131524 A1 | 6/2005 | Majercak et al. |
| 2005/0131525 A1 | 6/2005 | Hartley |
| 2005/0143817 A1 | 6/2005 | Hunter et al. |
| 2005/0163821 A1 | 7/2005 | Sung et al. |
| 2005/0165347 A1 | 7/2005 | Bardy |
| 2005/0203605 A1 | 9/2005 | Dolan |
| 2005/0229670 A1 | 10/2005 | Perreault |
| 2005/0234503 A1 | 10/2005 | Ravenscroft et al. |
| 2005/0240147 A1 | 10/2005 | Makower et al. |
| 2005/0245906 A1 | 11/2005 | Makower et al. |
| 2006/0004286 A1 | 1/2006 | Chang et al. |
| 2006/0004323 A1 | 1/2006 | Chang et al. |
| 2006/0020327 A1 | 1/2006 | Lashinski |
| 2006/0063973 A1 | 3/2006 | Makower et al. |
| 2006/0085027 A1 | 4/2006 | Santin |
| 2006/0095066 A1 | 5/2006 | Chang et al. |
| 2006/0106361 A1 | 5/2006 | Muni et al. |
| 2006/0106417 A1 | 5/2006 | Tessmer et al. |
| 2006/0135981 A1 | 6/2006 | Lenker et al. |
| 2006/0142736 A1 | 6/2006 | Hissink et al. |
| 2006/0162722 A1 | 7/2006 | Boehm et al. |
| 2006/0167540 A1 | 7/2006 | Masters et al. |
| 2006/0210605 A1 | 9/2006 | Chang et al. |

(56) References Cited

U.S. PATENT DOCUMENTS

| | | |
|---|---|---|
| 2006/0247499 A1 | 11/2006 | Butler et al. |
| 2006/0265042 A1 | 11/2006 | Catanese, III et al. |
| 2006/0276871 A1 | 12/2006 | Lamson et al. |
| 2007/0005094 A1* | 1/2007 | Eaton .................. A61P 37/00 606/199 |
| 2007/0055348 A1 | 3/2007 | Pryor |
| 2007/0079494 A1 | 4/2007 | Serrano |
| 2007/0100435 A1 | 5/2007 | Case et al. |
| 2007/0106366 A1 | 5/2007 | Delaloye et al. |
| 2007/0112373 A1 | 5/2007 | Carr et al. |
| 2007/0129751 A1 | 6/2007 | Muni et al. |
| 2007/0131525 A1 | 6/2007 | Lu et al. |
| 2007/0135789 A1 | 6/2007 | Chang et al. |
| 2007/0156211 A1 | 7/2007 | Ferren et al. |
| 2007/0162100 A1 | 7/2007 | Gabbay |
| 2007/0167682 A1 | 7/2007 | Goldfarb et al. |
| 2007/0179599 A1 | 8/2007 | Brodbeck et al. |
| 2007/0191922 A1 | 8/2007 | Hartley |
| 2007/0207186 A1 | 9/2007 | Scanlon et al. |
| 2007/0208252 A1 | 9/2007 | Makower |
| 2007/0208301 A1 | 9/2007 | Evard et al. |
| 2007/0227544 A1 | 10/2007 | Betsy et al. |
| 2007/0233225 A1 | 10/2007 | Rapacki et al. |
| 2007/0249896 A1 | 10/2007 | Goldfarb et al. |
| 2007/0250105 A1 | 10/2007 | Ressemann et al. |
| 2007/0269385 A1 | 11/2007 | Yun et al. |
| 2007/0270941 A1 | 11/2007 | Headley et al. |
| 2007/0282305 A1 | 12/2007 | Goldfarb et al. |
| 2007/0289677 A1 | 12/2007 | Ma et al. |
| 2007/0293726 A1 | 12/2007 | Goldfarb et al. |
| 2007/0293727 A1 | 12/2007 | Goldfarb et al. |
| 2007/0293946 A1 | 12/2007 | Gonzales et al. |
| 2007/0297186 A1 | 12/2007 | Hoover et al. |
| 2007/0299043 A1 | 12/2007 | Hunter et al. |
| 2008/0015540 A1 | 1/2008 | Muni et al. |
| 2008/0027481 A1 | 1/2008 | Gilson et al. |
| 2008/0053458 A1 | 3/2008 | De Silva et al. |
| 2008/0058295 A1 | 3/2008 | Chaudry |
| 2008/0058296 A1 | 3/2008 | Chaudry |
| 2008/0069858 A1 | 3/2008 | Weber |
| 2008/0077226 A1 | 3/2008 | Ouellette et al. |
| 2008/0077230 A1 | 3/2008 | Heaney et al. |
| 2008/0082162 A1 | 4/2008 | Boismier et al. |
| 2008/0085293 A1 | 4/2008 | Yang |
| 2008/0089952 A1 | 4/2008 | Hunter et al. |
| 2008/0097154 A1 | 4/2008 | Makower et al. |
| 2008/0097239 A1 | 4/2008 | Chang et al. |
| 2008/0097295 A1 | 4/2008 | Makower et al. |
| 2008/0097400 A1 | 4/2008 | Chang et al. |
| 2008/0097514 A1 | 4/2008 | Chang et al. |
| 2008/0097515 A1 | 4/2008 | Chang et al. |
| 2008/0097516 A1 | 4/2008 | Chang et al. |
| 2008/0097568 A1 | 4/2008 | Savage et al. |
| 2008/0097575 A1 | 4/2008 | Cottone |
| 2008/0097576 A1 | 4/2008 | Cottone et al. |
| 2008/0097580 A1 | 4/2008 | Dave |
| 2008/0097581 A1 | 4/2008 | Shanley |
| 2008/0097591 A1 | 4/2008 | Savage et al. |
| 2008/0103361 A1 | 5/2008 | Makower et al. |
| 2008/0103521 A1 | 5/2008 | Makower et al. |
| 2008/0103584 A1 | 5/2008 | Su et al. |
| 2008/0113000 A1 | 5/2008 | Hunter et al. |
| 2008/0119693 A1 | 5/2008 | Makower et al. |
| 2008/0125626 A1 | 5/2008 | Chang et al. |
| 2008/0125720 A1 | 5/2008 | Kim et al. |
| 2008/0132938 A1 | 6/2008 | Chang et al. |
| 2008/0145514 A1 | 6/2008 | Hunter et al. |
| 2008/0154237 A1 | 6/2008 | Chang et al. |
| 2008/0154250 A1 | 6/2008 | Makower et al. |
| 2008/0183128 A1 | 7/2008 | Morriss et al. |
| 2008/0195041 A1 | 8/2008 | Goldfarb et al. |
| 2008/0228085 A1 | 9/2008 | Jenkins et al. |
| 2008/0234720 A1 | 9/2008 | Chang et al. |
| 2008/0243140 A1 | 10/2008 | Gopferich et al. |
| 2008/0262468 A1 | 10/2008 | Clifford et al. |
| 2008/0262505 A1 | 10/2008 | Shahoian |
| 2008/0262508 A1 | 10/2008 | Clifford et al. |
| 2008/0262509 A1 | 10/2008 | Clifford et al. |
| 2008/0262510 A1 | 10/2008 | Clifford |
| 2008/0262593 A1 | 10/2008 | Ryan et al. |
| 2008/0275483 A1 | 11/2008 | Makower et al. |
| 2008/0281156 A1 | 11/2008 | Makower et al. |
| 2008/0287908 A1 | 11/2008 | Muni et al. |
| 2008/0306579 A1 | 12/2008 | Dolan et al. |
| 2008/0319424 A1 | 12/2008 | Muni et al. |
| 2009/0004272 A1 | 1/2009 | Gibson et al. |
| 2009/0004273 A1 | 1/2009 | Gibson et al. |
| 2009/0005763 A1 | 1/2009 | Makower et al. |
| 2009/0017090 A1 | 1/2009 | Arensdorf et al. |
| 2009/0028923 A1 | 1/2009 | Muni et al. |
| 2009/0030274 A1 | 1/2009 | Goldfarb et al. |
| 2009/0035351 A1 | 2/2009 | Berglund et al. |
| 2009/0036968 A1 | 2/2009 | Hepworth et al. |
| 2009/0036974 A1 | 2/2009 | Penn et al. |
| 2009/0041824 A1 | 2/2009 | Zugates et al. |
| 2009/0047326 A1 | 2/2009 | Eaton et al. |
| 2009/0047327 A1 | 2/2009 | Eaton et al. |
| 2009/0050145 A1 | 2/2009 | De Silva et al. |
| 2009/0056709 A1 | 3/2009 | Worsoff |
| 2009/0093823 A1 | 4/2009 | Chang et al. |
| 2009/0177272 A1 | 7/2009 | Abbate et al. |
| 2009/0182371 A1 | 7/2009 | Clausen et al. |
| 2009/0187098 A1 | 7/2009 | Makower et al. |
| 2009/0187211 A1 | 7/2009 | Mackiewicz |
| 2009/0192488 A1 | 7/2009 | Eaton et al. |
| 2009/0192489 A1 | 7/2009 | Eaton et al. |
| 2009/0192490 A1 | 7/2009 | Eaton et al. |
| 2009/0192491 A1 | 7/2009 | Eaton et al. |
| 2009/0192492 A1 | 7/2009 | Eaton et al. |
| 2009/0198179 A1 | 8/2009 | Abbate et al. |
| 2009/0198216 A1 | 8/2009 | Muni et al. |
| 2009/0220571 A1 | 9/2009 | Eaton et al. |
| 2009/0227945 A1 | 9/2009 | Eaton et al. |
| 2009/0238859 A1 | 9/2009 | Eaton et al. |
| 2009/0240112 A1 | 9/2009 | Goldfarb et al. |
| 2009/0306624 A1 | 12/2009 | Arensdorf et al. |
| 2009/0312745 A1 | 12/2009 | Goldfarb et al. |
| 2010/0043197 A1 | 2/2010 | Abbate et al. |
| 2011/0004193 A1 | 1/2011 | Eaton et al. |
| 2011/0004194 A1 | 1/2011 | Eaton et al. |
| 2011/0004195 A1 | 1/2011 | Eaton et al. |
| 2011/0004196 A1 | 1/2011 | Eaton et al. |
| 2011/0015612 A1 | 1/2011 | Arcand et al. |
| 2011/0021986 A1 | 1/2011 | Zamboni |
| 2011/0066135 A1 | 3/2011 | Eaton et al. |
| 2011/0125091 A1 | 5/2011 | Abbate |
| 2011/0167964 A1 | 7/2011 | Price |
| 2012/0101429 A1 | 4/2012 | Eaton et al. |
| 2013/0041463 A1 | 2/2013 | Ressemann |
| 2013/0066358 A1 | 3/2013 | Nalluri et al. |
| 2013/0231693 A1 | 9/2013 | Edgren et al. |
| 2013/0245608 A1 | 9/2013 | Muni et al. |
| 2013/0253567 A1 | 9/2013 | Edgren et al. |
| 2013/0281982 A1 | 10/2013 | Makower et al. |
| 2013/0304232 A1 | 11/2013 | Gries |
| 2014/0018839 A1 | 1/2014 | Renner et al. |
| 2014/0074065 A1 | 3/2014 | Muni et al. |
| 2014/0107615 A1 | 4/2014 | Doshi et al. |
| 2014/0276408 A1 | 9/2014 | Abbate |
| 2014/0283349 A1 | 9/2014 | Abbate et al. |
| 2014/0324025 A1 | 10/2014 | Arensdorf et al. |
| 2015/0081017 A1 | 3/2015 | Abbate et al. |
| 2016/0287854 A1 | 10/2016 | Eaton et al. |
| 2017/0128093 A1 | 5/2017 | Eaton et al. |
| 2019/0125935 A1 | 5/2019 | Eaton et al. |
| 2019/0143087 A1 | 5/2019 | Eaton et al. |

FOREIGN PATENT DOCUMENTS

| | | |
|---|---|---|
| EP | 0 423 916 A1 | 4/1991 |
| EP | 0 761 251 A1 | 3/1997 |
| EP | 0 938 880 A2 | 9/1999 |
| EP | 1 415 671 A1 | 5/2004 |
| EP | 1 870 057 A1 | 12/2007 |

(56) References Cited

FOREIGN PATENT DOCUMENTS

| | | |
|---|---|---|
| FR | 2 916 135 A1 | 11/2008 |
| GB | 165 537 A | 6/1921 |
| JP | 2-500521 A | 2/1990 |
| JP | H-04-25755 U | 2/1992 |
| JP | H-6-5800 Y2 | 2/1994 |
| JP | 6-506672 A | 7/1994 |
| JP | 6-329542 A | 11/1994 |
| JP | 8-117326 A | 5/1996 |
| JP | 11-309217 A | 11/1999 |
| JP | 2000-507630 A | 6/2000 |
| JP | 2001-506144 A | 5/2001 |
| JP | 2001-520188 A | 10/2001 |
| WO | WO-89/00839 A1 | 2/1989 |
| WO | WO-96/39098 A1 | 12/1996 |
| WO | WO-97/36949 A1 | 10/1997 |
| WO | WO-99/20261 A2 | 4/1999 |
| WO | WO-99/20261 A3 | 4/1999 |
| WO | WO-01/02024 A1 | 1/2001 |
| WO | WO-01/02024 C1 | 1/2001 |
| WO | WO-01/26658 A2 | 4/2001 |
| WO | WO-01/26658 A3 | 4/2001 |
| WO | WO-01/30411 A1 | 5/2001 |
| WO | WO-01/95834 A1 | 12/2001 |
| WO | WO-03/090818 A2 | 11/2003 |
| WO | WO-03/090818 A3 | 11/2003 |
| WO | WO-03/099359 A1 | 12/2003 |
| WO | WO-2004/016200 A1 | 2/2004 |
| WO | WO-2004/082525 A2 | 9/2004 |
| WO | WO-2004/082525 A3 | 9/2004 |
| WO | WO-2006/020180 A2 | 2/2006 |
| WO | WO-2006/020180 A3 | 2/2006 |
| WO | WO-2006/107957 A2 | 10/2006 |
| WO | WO-2006/107957 A3 | 10/2006 |
| WO | WO-2007/060972 A2 | 5/2007 |
| WO | WO-2007/060972 A3 | 5/2007 |
| WO | WO-2007/067451 A2 | 6/2007 |
| WO | WO-2007/067451 A3 | 6/2007 |
| WO | WO-2007/094004 A2 | 8/2007 |
| WO | WO-2007/094004 A3 | 8/2007 |
| WO | WO-2007/113586 A1 | 10/2007 |
| WO | WO-2007/134215 A2 | 11/2007 |
| WO | WO-2007/134215 A3 | 11/2007 |
| WO | WO-2007/139668 A2 | 12/2007 |
| WO | WO-2007/139668 A3 | 12/2007 |
| WO | WO-2008/008389 A2 | 1/2008 |
| WO | WO-2008/008389 A3 | 1/2008 |
| WO | WO-2008/025156 A1 | 3/2008 |
| WO | WO-2008/033533 A2 | 3/2008 |
| WO | WO-2008/051453 A2 | 5/2008 |
| WO | WO-2008/051453 A3 | 5/2008 |
| WO | WO-2008/051881 A2 | 5/2008 |
| WO | WO-2008/051881 A3 | 5/2008 |
| WO | WO-2008/054655 A2 | 5/2008 |
| WO | WO-2008/054655 A3 | 5/2008 |
| WO | WO-2008/070996 A1 | 6/2008 |
| WO | WO-2008/154143 A2 | 12/2008 |
| WO | WO-2008/154143 A3 | 12/2008 |
| WO | WO-2009/079418 A2 | 6/2009 |
| WO | WO-2009/079418 A3 | 6/2009 |
| WO | WO-2010/014834 A1 | 2/2010 |
| WO | WO-2010/130297 A1 | 11/2010 |
| WO | WO-2010/132648 A1 | 11/2010 |
| WO | WO-2012/083594 A1 | 6/2012 |
| WO | WO-2012/107229 A1 | 8/2012 |
| WO | WO-2012/150290 A1 | 11/2012 |
| WO | WO-2013/158337 A1 | 10/2013 |
| WO | WO-2014/151963 A1 | 9/2014 |

OTHER PUBLICATIONS

Bolliger, C.T. et al. (1999). "Evaluation of a New Self-Expandable Silicone Stent in an Experimental Tracheal Stenosis," Chest 115:496-501.

Corrected Notice of Allowability dated Jan. 24, 2019, for U.S. Appl. No. 15/007,848, filed Jan. 27, 2016, 2 pages.

Corrected Notice of Allowability dated Apr. 16, 2019, for U.S. Appl. No. 12/779,240, filed May 13, 2010, 4 pages.

Eberhart, R.C. et al. (2003). "Bioresorbable Polymeric Stents: Current Status and Future Promise," *J. Biomater. Sci. Polymer Edn.* 14(4):299-312.

European Search Report dated Feb. 21, 2011, for EP Patent Application No. 10011116.0 filed on Apr. 4, 2006, 8 pages.

European Search Report dated Feb. 21, 2011, for EP Patent Application No. 10011117.8 filed on Apr. 4, 2006, 8 pages.

European Search Report dated Feb. 21, 2011, for EP Patent Application No. 10011118.6 filed on Apr. 4, 2006, 9 pages.

European Search Report dated Sep. 25, 2012 for European Patent Application No. 10775524.1, filed on May 13, 2010, 9 pages.

Extended European Search Report dated Jun. 27, 2014, for European Patent Application No. 14156004.5, filed on May 13, 2010, 13 pages.

Extended European Search Report dated Nov. 16, 2016, for EP Application No. 16 165 633.5, filed on May 13, 2010, 9 pages.

Extended European Search Report dated Jun. 18, 2015, for EP Patent Application No. 08 863 327.6, filed on Jul. 16, 2010, 8 pages.

Extended European Search Report dated Jun. 26, 2015, for European Patent Application No. 09 803 604.9, filed on Jul. 30, 2009, 7 pages.

Extended European Search Report dated Oct. 24, 2016, for European Patent Application No. 16 182 023.8, filed on Mar. 12, 2004, 7 pages.

Extended European Search Report dated Jan. 27, 2017, for EP Application No. 14 770 721.0, filed on Mar. 13, 2014, 10 pages.

Final Office Action dated Apr. 12, 2012, for U.S. Appl. No. 12/883,087, filed Sep. 15, 2010, 7 pages.

Final Office Action dated Apr. 16, 2012, for U.S. Appl. No. 12/334,373, filed Dec. 12, 2008, 7 pages.

Final Office Action dated Aug. 18, 2010, for U.S. Appl. No. 11/775,157, filed Jul. 9, 2007, 12 pages.

Final Office Action dated Dec. 2, 2013, for U.S. Appl. No. 12/779,240, filed May 13, 2010, 10 pages.

Final Office Action dated Jan. 27, 2011, for U.S. Appl. No. 12/479,794, filed Jun. 6, 2009, 6 pages.

Final Office Action dated Jan. 8, 2009, for U.S. Appl. No. 10/800,162, filed Mar. 12, 2004, 5 pages.

Final Office Action dated Jul. 22, 2009, for U.S. Appl. No. 11/398,342, filed Apr. 4, 2006, 8 pages.

Final Office Action dated Jul. 8, 2010, for U.S. Appl. No. 11/398,342, filed Apr. 4, 2006, 7 pages.

Final Office Action dated Mar. 1, 2012, for U.S. Appl. No. 12/270,695, filed Nov. 13, 2008, 26 pages.

Final Office Action dated Mar. 6, 2013, for U.S. Appl. No. 13/341,732, filed Dec. 30, 2011, 7 pages.

Final Office Action dated May 19, 2014, for U.S. Appl. No. 13/341,732, filed Dec. 30, 2011, 7 pages.

Final Office Action dated May 29, 2012, for U.S. Appl. No. 12/334,382, filed Dec. 12, 2008, 7 pages.

Final Office Action dated May 30, 2013, for U.S. Appl. No. 12/541,840, filed Aug. 14, 2009, 11 pages.

Final Office Action dated May 5, 2014 for U.S. Appl. No. 12/883,087, filed Sep. 15, 2010, 10 pages.

Final Office Action dated Nov. 28, 2011, for U.S. Appl. No. 12/883,071, filed Sep. 15, 2010, 7 pages.

Final Office Action dated Sep. 10, 2013, for U.S. Appl. No. 12/334,395, filed Dec. 12, 2008, 8 pages.

Final Office Action dated Sep. 17, 2014, for U.S. Appl. No. 12/334,395, filed Dec. 12, 2008, 11 pages.

Final Office Action dated Feb. 12, 2015, for U.S. Appl. No. 13/341,732, filed Dec. 30, 2011, 8 pages.

Final Office Action dated Oct. 20, 2015, for U.S. Appl. No. 12/883,087, filed Sep. 15, 2010, 15 pages.

Final Office Action dated Nov. 25, 2015, for U.S. Appl. No. 12/779,240, filed May 13, 2010, 15 pages.

Final Office Action dated Feb. 8, 2016, for U.S. Appl. No. 12/334,395, filed Dec. 12, 2008, 18 pages.

Final Office Action dated Apr. 7, 2016, for U.S. Appl. No. 14/210,078, filed Mar. 13, 2014, 7 pages.

(56) References Cited

OTHER PUBLICATIONS

Final Office Action dated Jun. 29, 2016, for U.S. Appl. No. 14/327,100, filed Jul. 9, 2014, 17 pages.
Final Office Action dated Sep. 16, 2016, for U.S. Appl. No. 14/081,974, filed Nov. 15, 2013, 12 pages.
Final Office Action dated Sep. 20, 2016, for U.S. Appl. No. 14/550,634, filed Nov. 21, 2014, 11 pages.
Final Office Action dated Jul. 26, 2017, for U.S. Appl. No. 12/779,240, filed May 13, 2010, 13 pages.
Final Office Action dated Sep. 7, 2017, for U.S. Appl. No. 14/210,078, filed Mar. 13, 2014, 9 pages.
Final Office Action dated Nov. 30, 2017, for U.S. Appl. No. 14/081,974, filed Nov. 15, 2013, 11 pages.
Final Office Action dated Dec. 19, 2018, for U.S. Appl. No. 14/210,078, filed Mar. 13, 2014, 7 pages.
Hietala, E-M. et al. (2001). "Biodegradation of the Copolymeric Polylactide Stent," *Journal of Vascular Research* 38:361-369.
Hosemann, W. et al. (Mar. 2003, e-pub. Oct. 10, 2002). "Innovative Frontal Sinus Stent Acting as a Local Drug-Releasing System," *Eur. Arch. Otorhinolarynol.* 260:131-134.
Hughes, J.P. et al. (Apr. 2004). "Use of a Ureteric Pigtail Stent as a Self-Retaining Frontal Sinus Stent," The Journal of Laryngology & Otology 118:299-301.
International Search Report dated Feb. 24, 2006, for PCT Application No. PCT/US04/07828, filed Mar. 12, 2004, 2 pages.
International Search Report dated Sep. 11, 2006, for PCT Patent Application No. PCT/US2006/012484 filed on Apr. 4, 2006, 7 pages.
International Search Report dated Mar. 19, 2008, for PCT Patent Application No. PCT/US2007/015813, filed on Jul. 10, 2007, 3 pages.
International Search Report dated Apr. 16, 2009, for PCT Application No. PCT/US2008/86718, filed on Dec. 12, 2008, 3 pages.
International Search Report dated Sep. 28, 2009, for PCT Application No. PCT/US2009/052287, filed on Jul. 30, 2009, 2 pages.
International Search Report dated Jul. 16, 2010 for PCT Patent Application No. PCT/US2010/034679, filed on May 13, 2010, 2 pages.
International Search Report dated Oct. 9, 2014, for PCT Patent Application No. PCT/US2014/026737, filed on Mar. 13, 2014, 5 pages.
Laaksovirta, S. (Aug. 22, 2003). Biodegradable, Self-Reinforced, Self-Expandable Lactic and Glycolic Acid (SR-PLGA 80/20) Copolymer Spiral Prostatic Stent: Analysis of Mechanical and Biological Properties and Clinical Results, Academic Dissertation, Medical School of the University of Tampere, 79 pages.
Lapchenko, A.S. et al. (Jun. 1996). "Polyphosphazene Prosthesis of the Frontonasal Bypass in Surgical Treatment of Acute and Chronic Inflammation of the Frontal Sinuses," *Vestnik Otorinolarinologii*, 2 pages.
Lavigne, F. et al. (May 2002). "Intrasinus Administration of Topical Budesonide to Allergic Patients With Chronic Rhinosinusitis Following Surgery," *The Laryngoscope* 112, 7 pages.
Min, Y-G. et al. (1995). "Application of Polylactic Acid Polymer in the Treatment of Acute Maxillary Sinusitis in Rabbits," *Acta Otolaryngol.* 115:548-552.
Min, Y-G. et al. (Aug. 1995). "Mucociliary Activity and Histopathology of Sinus Mucosa in Experimental Maxillary Sinusitis: A Comparison of Systemic Administration of Antibiotic and Antibiotic Delivery by Polylactic Acid Polymer," *The Laryngoscope* 105:835-842.
Mirza, S. et al. (Dec. 2000). "A Simple and Effective Frontal Sinus Stent," The Journal of Laryngology & Otology 114:955-956.
Mitty, H. et al. (1988). "Experience with a New Ureteral Stent Made of a Biocompatible Copolymer," Radiology 168:557-559.
Murphy, J.G. et al. (1992). "Percutaneous Polymeric Stents in Porcine Coronary Arteries: Initial Experience With Polyethylene Terephthalate Stents," *Circulation* 86:1596-1604.

Nguyen, K.T. et al. (2004). "Biomaterials and Stent Technology," Chapter 5 in *Tissue Engineering and Novel Delivery Systems*, 24 pages.
Non-Final Office Action dated May 8, 2015, for U.S. Appl. No. 12/334,395, filed Dec. 12, 2008, 11 pages.
Non-Final Office Action dated Apr. 16, 2014, for U.S. Appl. No. 12/334,395, filed Dec. 12, 2008, 9 pages.
Non-Final Office Action dated Dec. 9, 2009, for U.S. Appl. No. 11/775,157, filed Jul. 9, 2007, 12 pages.
Non-Final Office Action dated Feb. 27, 2014, for U.S. Appl. No. 12/270,695, filed Nov. 13, 2008, 7 pages.
Non-Final Office Action dated Jul. 1, 2010, for U.S. Appl. No. 12/479,794, filed Jun. 6, 2009, 5 pages.
Non-Final Office Action dated Jul. 13, 2011, for U.S. Appl. No. 12/334,373, filed Dec. 12, 2008, 8 pages.
Non-Final Office Action dated Jun. 12, 2014, for U.S. Appl. No. 14/082,010, filed Nov. 15, 2013, 6 pages.
Non-Final Office Action dated Jun. 14, 2011, for U.S. Appl. No. 12/437,374, filed May 7, 2009, 8 pages.
Non-Final Office Action dated Jun. 21, 2011, for U.S. Appl. No. 12/270,695, filed Nov. 13, 2008, 24 pages.
Non-Final Office Action dated Jun. 6, 2008, for U.S. Appl. No. 10/800,162, filed Mar. 12, 2004, 5 pages.
Non-Final Office Action dated Jun. 7, 2012, for U.S. Appl. No. 12/334,395, filed Dec. 12, 2008, 7 pages.
Non-Final Office Action dated Mar. 15, 2013, for U.S. Appl. No. 12/512,855, filed Jul. 30, 2009, 10 pages.
Non-Final Office Action dated Mar. 20, 2015, for U.S. Appl. No. 12/883,087, filed Sep. 15, 2010, 11 pages.
Non-Final Office Action dated Mar. 22, 2011, for U.S. Appl. No. 12/883,071, filed Sep. 15, 2010, 8 pages.
Non-Final Office Action dated Mar. 3, 2015, for U.S. Appl. No. 14/210,078, filed Mar. 13, 2014, 6 pages.
Non-Final Office Action dated Aug. 6, 2015, for U.S. Appl. No. 14/327,100, filed Jul. 7, 2014, 6 pages.
Non-Final Office Action dated May 11, 2012, for U.S. Appl. No. 12/883,071, filed Sep. 15, 2010, 7 pages.
Non-Final Office Action dated May 13, 2011, for U.S. Appl. No. 12/883,087, filed Sep. 15, 2010, 7 pages.
Non-Final Office Action dated May 14, 2012, for U.S. Appl. No. 12/779,240, filed May 13, 2010, 9 pages.
Non-Final Office Action dated Nov. 12, 2010, for U.S. Appl. No. 11/398,342, filed Apr. 4, 2006, 8 pages.
Non-Final Office Action dated Nov. 13, 2009, for U.S. Appl. No. 11/398,342, filed Apr. 4, 2006, 9 pages.
Non-Final Office Action dated Nov. 23, 2010, for U.S. Appl. No. 12/258,277, filed Oct. 24, 2008, 9 pages.
Non-Final Office Action dated Nov. 23, 2010, for U.S. Appl. No. 12/258,282, filed Oct. 24, 2008, 7 pages.
Non-Final Office Action dated Nov. 24, 2010, for U.S. Appl. No. 12/883,090, filed Sep. 15, 2010, 7 pages.
Non-Final Office Action dated Nov. 24, 2010, for U.S. Appl. No. 12/883,056, filed Sep. 15, 2010, 7 pages.
Non-Final Office Action dated Nov. 24, 2010, for U.S. Appl. No. 12/883,079, filed Sep. 15, 2010, 8 pages.
Non-Final Office Action dated Nov. 25, 2008, for U.S. Appl. No. 11/398,342, filed Apr. 4, 2006, 10 pages.
Non-Final Office Action dated Oct. 18, 2012, for U.S. Appl. No. 12/541,840, filed Aug. 14, 2009, 10 pages.
Non-Final Office Action dated Sep. 10, 2010, for U.S. Appl. No. 12/437,374, filed May 7, 2009, 8 pages.
Non-Final Office Action dated Sep. 12, 2013 for U.S. Appl. No. 13/341,732, filed Dec. 30, 2011, 5 pages.
Non-Final Office Action dated Sep. 22, 2009, for U.S. Appl. No. 12/419,927, filed Apr. 7, 2009, 4 pages.
Non-Final Office Action dated Sep. 22, 2009, for U.S. Appl. No. 12/419,943, filed Apr. 7, 2009, 5 pages.
Non-Final Office Action dated Sep. 22, 2009, for U.S. Appl. No. 12/419,930, filed Apr. 7, 2007, 4 pages.
Non-Final Office Action dated Sep. 22, 2009, for U.S. Appl. No. 12/419,937, filed Apr. 7, 2009, 4 pages.
Non-Final Office Action dated Sep. 22, 2009, for U.S. Appl. No. 12/419,925, filed Apr. 7, 2009, 4 pages.

(56) References Cited

OTHER PUBLICATIONS

Non-Final Office Action dated Sep. 23, 2013, for U.S. Appl. No. 12/883,087, filed Sep. 15, 2010, 7 pages.
Non-Final Office Action dated Sep. 23, 2014, for U.S. Appl. No. 13/341,732, filed Dec. 30, 2011, 8 pages.
Non-Final Office Action dated Sep. 26, 2011, for U.S. Appl. No. 12/334,382, filed Dec. 12, 2008, 7 pages.
Non-final Office Action dated Sep. 10, 2015, for U.S. Appl. No. 13/341,732, filed Dec. 30, 2011, 6 pages.
Non-final Office Action dated Nov. 12, 2015, for U.S. Appl. No. 14/327,100, filed Jul. 9, 2014, 12 pages.
Non-Final Office Action dated Nov. 18, 2016, for U.S. Appl. No. 12/779,240, filed May 13, 2010, 15 pages.
Non-Final Office Action dated Feb. 5, 2016, for U.S. Appl. No. 12/883,087, filed Sep. 15, 2010, 12 pages.
Non-Final Office Action dated Feb. 5, 2016, for U.S. Appl. No. 14/081,974, filed Nov. 15, 2013, 12 pages.
Non-Final Office Action dated Apr. 28, 2016, for U.S. Appl. No. 14/550,634, filed Nov. 21, 2014, 10 pages.
Non-Final Office Action dated Aug. 11, 2016, for U.S. Appl. No. 12/334,395, filed Dec. 12, 2008, 12 pages.
Non-Final Office Action dated Mar. 20, 2017, for U.S. Appl. No. 14/298,715, filed Jun. 6, 2014, 7 pages.
Non-Final Office Action dated Jan. 6, 2017, for U.S. Appl. No. 14/210,078, filed Mar. 13, 2014, 7 pages.
Non-Final Office Action dated Jun. 29, 2017, for U.S. Appl. No. 14/081,974, filed Nov. 15, 2013, 15 pages.
Non-Final Office Action dated Dec. 13, 2017, for U.S. Appl. No. 15/062,616, filed Mar. 7, 2016, 13 pages.
Non-Final Office Action dated Jul. 25, 2018, for U.S. Appl. No. 12/779,240, filed May 13, 2010, 14 pages.
Notice of Allowance (Corrected) dated May 29, 2014, for U.S. Appl. No. 12/512,855, filed Jul. 30, 2009, 4 pages.
Notice of Allowance dated Apr. 8, 2014, for U.S. Appl. No. 12/541,840, filed Aug. 14, 2009, 8 pages.
Notice of Allowance dated Aug. 20, 2012, for U.S. Appl. No. 12/437,374, filed May 7, 2009, 8 pages.
Notice of Allowance dated Dec. 23, 2009, for U.S. Appl. No. 12/419,943, filed Apr. 7, 2009, 2 pages.
Notice of Allowance dated Dec. 23, 2009, for U.S. Appl. No. 12/419,925, filed Apr. 7, 2009, 2 pages.
Notice of Allowance dated Dec. 24, 2009, for U.S. Appl. No. 12/419,927, filed Apr. 7, 2009, 2 pages.
Notice of Allowance dated Feb. 19, 2014, for U.S. Appl. No. 12/512,855, filed Jul. 30, 2009, 7 pages.
Notice of Allowance dated Feb. 2, 2010, for U.S. Appl. No. 12/419,937, filed Apr. 7, 2009, 2 pages.
Notice of Allowance dated Jan. 19, 2010, for U.S. Appl. No. 12/419,930, filed Apr. 7, 2009, 2 pages.
Notice of Allowance dated Jan. 21, 2014, for U.S. Appl. No. 12/883,071, filed Sep. 15, 2010, 6 pages.
Notice of Allowance dated Jul. 13, 2011, for U.S. Appl. No. 11/398,342, filed Apr. 4, 2006, 7 pages.
Notice of Allowance dated Jul. 15, 2013, for U.S. Appl. No. 12/334,382, filed Dec. 12, 2008, 9 pages.
Notice of Allowance dated Jul. 30, 2013, for U.S. Appl. No. 12/334,373, filed Dec. 12, 2008, 10 pages.
Notice of Allowance dated Jun. 12, 2014, for U.S. Appl. No. 12/270,695, filed Nov. 13, 2008, 7 pages.
Notice of Allowance dated Mar. 18, 2011, for U.S. Appl. No. 12/258,277, filed Oct. 24, 2008, 7 pages.
Notice of Allowance dated Mar. 21, 2011, for U.S. Appl. No. 12/258,282, filed Oct. 24, 2008, 8 pages.
Notice of Allowance dated Mar. 21, 2011, for U.S. Appl. No. 12/883,059, filed Sep. 15, 2010, 10 pages.
Notice of Allowance dated Mar. 23, 2011, for U.S. Appl. No. 12/883,079, filed Sep. 15, 2010, 9 pages.
Notice of Allowance dated Mar. 25, 2011 for U.S. Appl. No. 12/883,090, filed Sep. 15, 2010, 8 pages.
Notice of Allowance dated Mar. 25, 2011, for U.S. Appl. No. 12/883,056, filed Sep. 15, 2010, 8 pages.
Notice of Allowance dated May 22, 2013, for U.S. Appl. No. 11/775,157, filed Jul. 9, 2007, 10 pages.
Notice of Allowance dated Nov. 2, 2012, for U.S. Appl. No. 11/775,157, filed Jul. 9, 2007, 8 pages.
Notice of Allowance dated Nov. 27, 2013, for U.S. Appl. No. 12/512,855, filed Jul. 30, 2009, 9 pages.
Notice of Allowance dated Nov. 9, 2011, for U.S. Appl. No. 12/479,794, filed Jun. 6, 2009, 7 pages.
Notice of Allowance dated Sep. 19, 2013, for U.S. Appl. No. 12/883,071, filed Sep. 15, 2010, 6 pages.
Notice of Allowance dated Nov. 12, 2014, for U.S. Appl. No. 14/082,010, filed Nov. 15, 2013, 5 pages.
Notice of Allowance dated Feb. 17, 2015, for U.S. Appl. No. 14/082,010, filed Nov. 15, 2013, 5 pages.
Notice of Allowance dated Nov. 18, 2016, for U.S. Appl. No. 14/298,715, filed Jun. 6, 2014, 8 pages.
Notice of Allowance dated Jun. 20, 2017, for U.S. Appl. No. 14/298,715, filed Jun. 6, 2014, 5 pages.
Notice of Allowance dated Dec. 20, 2018, for U.S. Appl. No. 15/007,848, filed Jan. 27, 2016, 8 pages.
Notice of Allowance dated Mar. 7, 2019, for U.S. Appl. No. 12/779,240, filed May 13, 2010, 11 pages.
Notice of Allowance dated Mar. 25, 2019, for U.S. Appl. No. 12/779,240, filed May 13, 2010, 6 pages.
Notice of Allowance dated May 13, 2019, for U.S. Appl. No. 14/210,078, filed Mar. 13, 2014, 8 pages.
Nuutinen, J-P. et al. (2002). "Mechanical Properties and in vitro Degradation of Bioresorbable Knitted Stents," *J. Biomater. Sci. Polymer Edn.* 13(12):1313-1323.
Nuutinen, J-P. et al. (2003). "Theoretical and Experimental Evaluation of the Radial Force of Self-Expanding Braided Bioabsorbable Stents," *J. Biomater. Sci. Polymer Edn.* 14(7):677-687.
Partial Supplementary European Search Report dated Oct. 27, 2016, for EP Application No. 14 770 721.0, filed on Mar. 13, 2014, 6 pages.
Parviainen, M. et al. (2000). "A New Biodegradable Stent for the Pancreaticojejunal Anastomosis After Pancreaticoduodenal Resection: In Vitro Examination and Pilot Experiences in Humans," *Pancreas* 21(1): 14-21.
Piskunov, S. et al. (1993). "The Prolongation of Drug Action in the Treatment of Diseases of the Nose and Paranasal Sinuses," *Rhinology* 31:33-36.
Piskunov, S.Z. et al. (May-Jun. 1989). "Application of Drugs Based on Polymers in the Treatment of Acute and Chronic Maxillary Sinusitis," *Vestnik Otorinolaringologii* (3)33-35.
Roumestan, C. et al. (2003). "Fluticasone Propionate and Mometasone Furoate Have Equivalent Transcriptional Potencies," *Clinical and Experimental Allergy* 33:895-901.
Shikani, A.H. (Aug. 1996). "Use of Antibiotics for Expansion of the Merocel® Packing Following Endoscopic Sinus Surgery," *ENT—Ear, Nose & Throat Journal* 75(8):524-528.
St. Croix, B. et al. (Aug. 18, 2000). "Gene Expressed in Human Tumor Endothelium," *Science* 289:1197-1202.
Su, S-H. et al. (2003). "Expandable Bioresorbable Endovascular Stent. I. Fabrication and Properties," *Annals of Biomedical Engineering* 31:667-677.
Supplementary European Search Report and Search Opinion dated Nov. 9, 2010, for European Patent Application No. 04720509.1, filed on Mar. 12, 2004, 3 pages.
Supplementary European Search Report and Search Opinion dated Jun. 26, 2015, for European Patent Application No. 09803604.9, filed on Jul. 30, 2009, 7 pages.
Tamai, H. et al. (1999). "A Biodegradable Ploy-/-lactic Acid Coronary Stent in the Porcine Coronary Artery," *Journal of Interventional Cardiology* 12(6):443-450.
Thierry, B. et al. (Nov./Dec. 2003, e-pub. Oct. 7, 2003). "Bioactive Coatings of Endovascular Stents Based on Polyelectrolyte Multilayers," *Biomacromolecules* 4(6):1564-1571.
Third Party Submission under 37 CFR 1.290 submitted Oct. 11, 2014, against U.S. Appl. No. 14/081,974, filed Nov. 15, 2013, 8 pages.

(56) References Cited

OTHER PUBLICATIONS

Toffel, P.H. (Mar. 2001). "The Balanced Philosophy of Secure Multimodal Endoscopic Sinus Surgery with Adjunct Use of Middle Meatal Stenting and Middle Turbinate Modification," *Operative Techniques in Otolaryngology—Head and Neck Surgery* 12(1):40-45.

Vogt, F. et al. (2004, e-pub. Jul. 20, 2004). "Long-Term Assessment of a Novel Biodegradable Paclitaxel-Eluting Coronary Polylactide Stent," *European Heart Journal* 25:1330-1340.

Written Opinion of the International Searching Authority dated Feb. 24, 2006 for PCT Application No. PCT/US04/07828, filed Mar. 12, 2004, 3 pages.

Written Opinion of the International Searching Authority dated on Nov. 9, 2006, for PCT Patent Application No. PCT/US2006/012484, filed on Apr. 4, 2006, 11 pages.

Written Opinion of the International Searching Authority dated Mar. 19, 2008, for PCT Patent Application No. PCT/US2007/015813, filed on Jul. 10, 2007, 7 pages.

Written Opinion of the International Searching Authority dated Apr. 16, 2009, for PCT Application No. PCT/US2008/86718, filed on Dec. 12, 2008, 13 pages.

Written Opinion of the International Searching Authority dated Sep. 28, 2009, for PCT Application No. PCT/US2009/052287, filed on Jul. 30, 2009, 9 pages.

Written Opinion dated Jul. 16, 2010, for PCT Patent Application No. PCT/US2010/034679, filed on May 13, 2010, 4 pages.

Written Opinion of the International Searching Authority dated Oct. 9, 2014, for PCT Patent Application No. PCT/US2014/026737, filed on Mar. 13, 2014, 5 pages.

\* cited by examiner

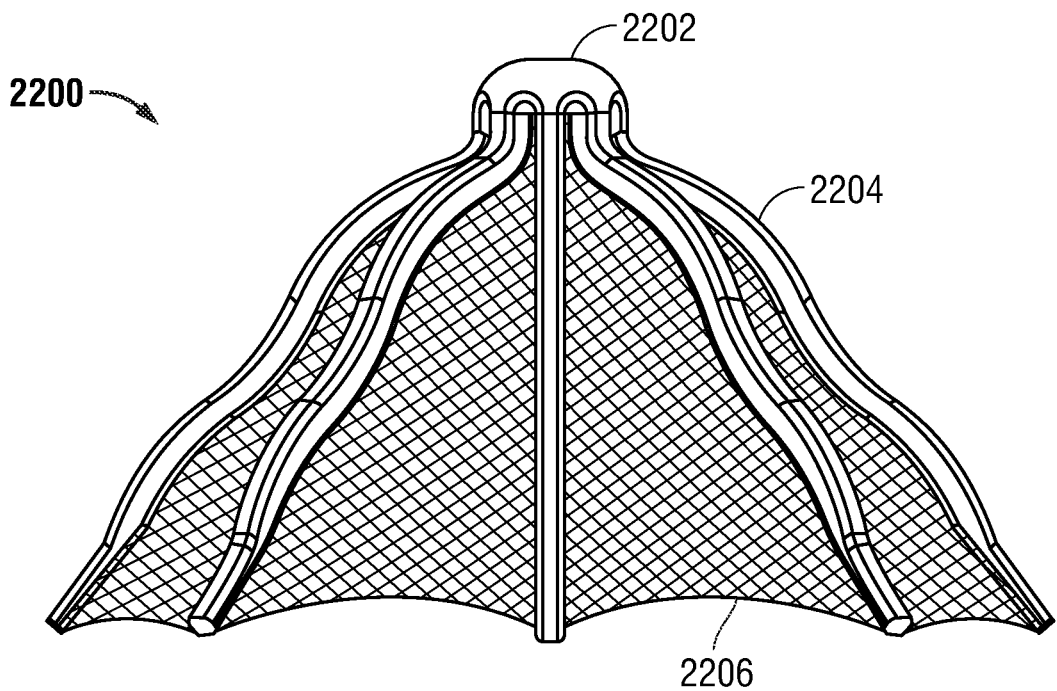
FIG. 22
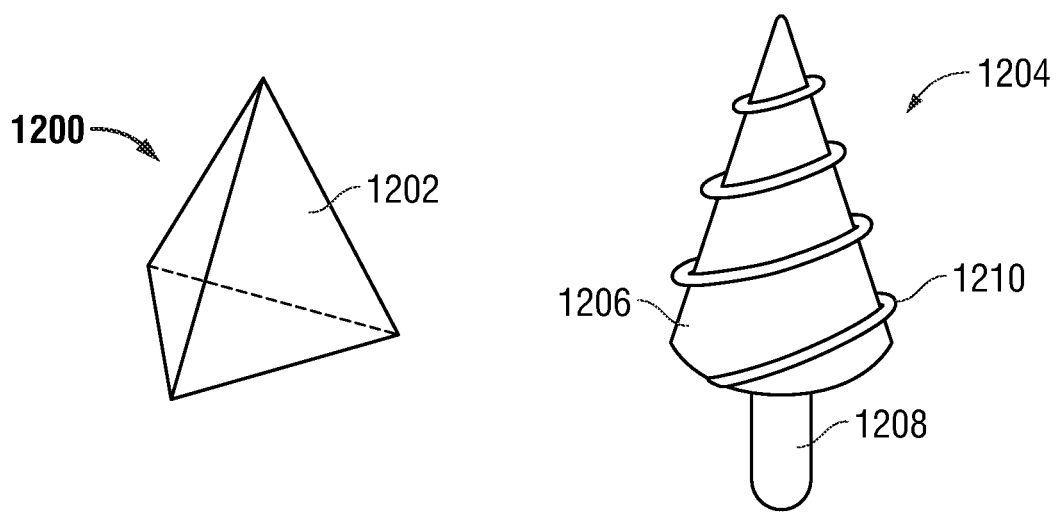
FIG. 12A  FIG. 12B

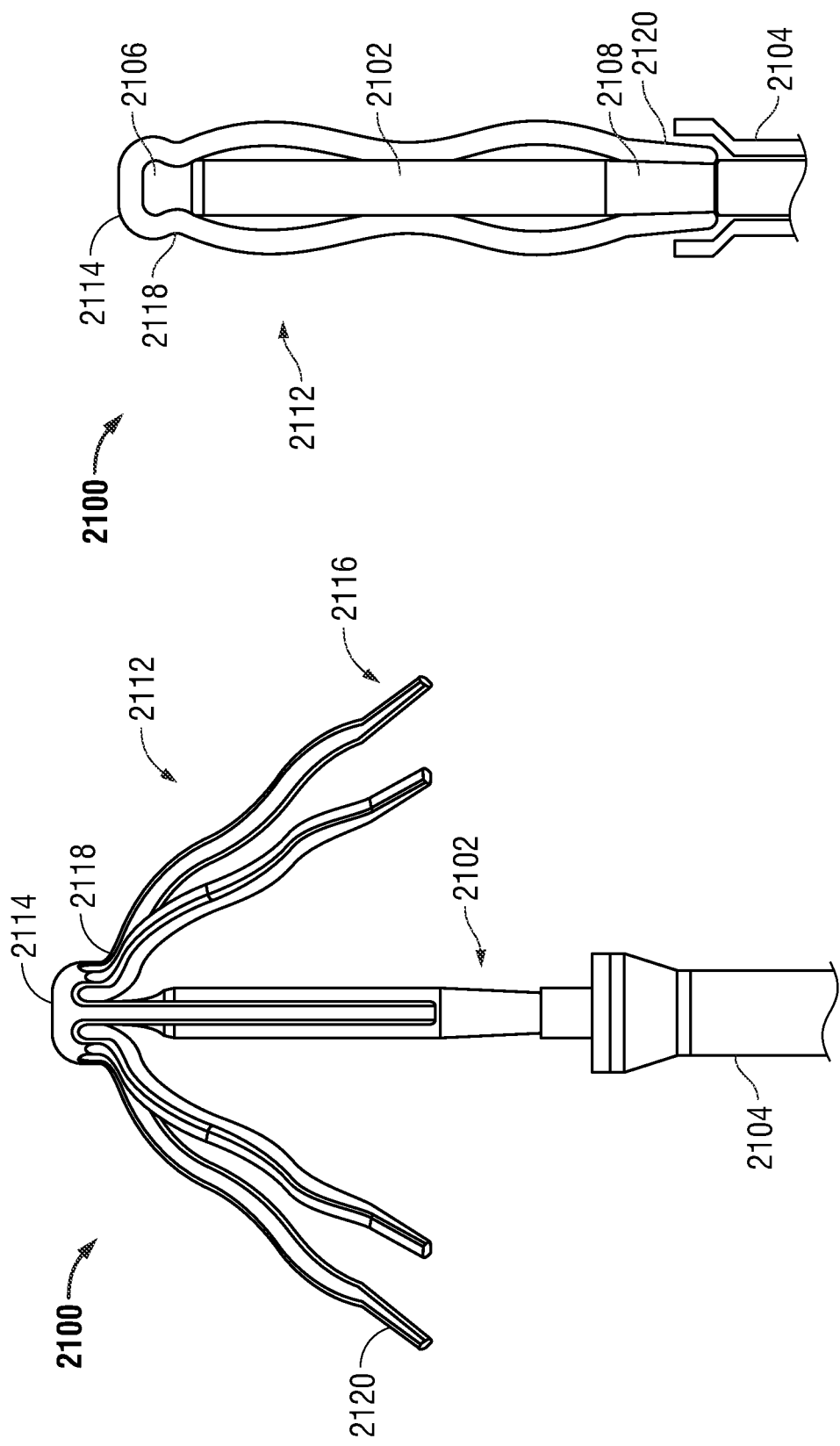

EXPANDABLE DEVICES AND METHODS FOR TREATING A NASAL OR SINUS CONDITION

CROSS-REFERENCE TO RELATED APPLICATIONS

This application is a continuation of U.S. application Ser. No. 12/779,240, filed on May 13, 2010, now issued as U.S. Pat. No. 10,357,640, which claims priority to U.S. Provisional Application Ser. No. 61/178,896, filed on May 15, 2009 and titled "EXPANDABLE DEVICES AND METHODS THEREFOR," each of which is hereby incorporated by reference in its entirety.

FIELD

The present invention relates generally to expandable devices and methods for using them. At least a portion of the devices may be biodegradable and/or configured for drug delivery.

BACKGROUND

Nasal polyposis is a condition where inflammation in the nasal passages or paranasal sinuses leads to the formation of one or more nasal polyps (small, sac-like growths of inflamed nasal mucosa). Nasal polyps may at least partially obstruct the nasal airways and/or one or more sinus ostia, and may be associated with symptoms such as difficulty breathing rhinorrhea, postnasal drip/drainage, nasal crusting, headaches, sneezing, snoring, itchy eyes, pain and general discomfort. The exact mechanism of polyp formation is unknown, but has been associated with other conditions such as chronic inflammation, asthma, hay fever, chronic sinus infections (e.g., chronic sinusitis, allergic rhinitis, allergic fungal sinusitis, etc.), cystic fibrosis, autonomous nervous system dysfunction, aspirin sensitivity and genetic predisposition.

There are a number of treatments currently available for managing nasal polyposis. Orally-administered corticosteroids, intranasal steroid sprays, and intra-polyp steroid injections are administered to reduce the volume of one or more polyps, while polypectomies surgically remove one or more nasal polyps. Each of these treatments, however, has limitations. Specifically, polypectomies may result in one or more symptoms that result from the general stress of surgery and anesthesia, such as pain, discomfort, lethargy and sleeplessness. Intranasal steroid sprays, while useful in shrinking isolated polyps, are largely ineffective for larger or densely packed polyps. Intra-polyp steroid injections have a small chance of causing temporary or permanent vision loss. Orally-administered corticosteroids may only be administered three to four times a year, and have a multitude of symptoms associated with both short-term and long-term use. Symptoms associated with short-term use include sleep disturbance, mood swings, weight gain, and fluid retention, while symptoms associated with long-term use include increased risk infections, osteoporosis, muscle weakness, and cataracts. Additionally, the non-surgical polyp treatments mentioned above do not immediately open a blocked airway or sinus ostium. As such, it may be desirable to find new and effective ways of treating nasal polyposis.

BRIEF SUMMARY

Described here are expandable devices and methods of using them. The devices may be useful in a variety of locations within the body for a number of different applications. In some variations, the devices have a low-profile configuration enabling low-profile delivery and an expanded configuration for apposition against tissue, and comprise a hub and a plurality of legs extending therefrom. Generally, the devices described here may comprise a hub and a plurality of legs. In some variations, the device may be formed as a single piece. In some of these variations, the device is formed from an injection-molded polymer or other injection-molded materials. In other variations, different portions of the device may be formed separately, and then joined into an assembled device.

The hub may have any suitable size and configuration. In some variations, the hub comprises one or more domed surfaces. In some of these variations the hub may comprise a domed surface and a flat top. In other variations, the hub may comprise a fully-domed portion. In still other variations, the hub may comprise one or more tapered portions, and/or one or more extension portions. The hub may have uniform or non-uniform thickness. Additionally, the hub may have any suitable cross-sectional shape, such as, for example, circular, oval, triangular, square, rectangular, or the like. In some variations, the hub comprises one or more slots, channels, or passageways therethrough.

Additionally, the devices described here may comprise any number of legs, and each leg may or may not have the same shape or configuration. In some variations, one or more of the plurality of legs comprises one or more inwardly-curved segments, one or more outwardly-curved segments, one or more laterally curved segments, one or more straight segments, or a combination thereof. For example, in some variations a leg may comprise a first straight segment and a second straight segment extending therefrom. In other variations, the legs may comprise a first straight segment and a first curved segment. In still other variations, the legs may comprise two or more straight segments and two or more curved segments. In some variations, one or more legs may comprise one or more bifurcated or trifurcated portions. The legs may have any suitable cross-sectional shape or shapes, such as, for example, a rectangle, square, trapezoid, or the like.

In some variations, at least a portion of these devices comprise a polymer. In some variations, the polymer is a biodegradable polymer. In instances where a biodegradable polymer is used, the device (or a portion thereof) is typically capable of biodegrading over a predetermined period of time (e.g., at least 3 weeks, at least 4 weeks, at least 5 weeks, at least 8 weeks, between about two weeks and about four weeks, between about 3 weeks and about 5 weeks, between about 4 weeks and about 6 weeks, between about 5 weeks and about 8 weeks, between about 7 weeks and about 10 weeks, between about 9 weeks and about 12 weeks, between about 11 weeks and about 14 weeks, and the like). In other variations, at least a portion of the devices comprises a metal or metal alloy.

In some variations, the devices are suitable for drug delivery. In some of these variations, the device (or a portion thereof) may comprise one or more drugs, one or more drug-releasing layers, one or more drug depots, reservoirs, or boluses, or a combination thereof. Each drug may be configured to be released from the device over a period or periods of time. Any suitable drug or agent may be used, and in some variations more than one drug or agent is used.

The devices may be sized and configured for implantation into one or more sinus or nasal regions, e.g., an ethmoid sinus cavity, a maxillary sinus cavity, a sphenoid sinus cavity, the osteomeatal complex, the nasal passage, or combinations thereof. In some variations, the device may be configured to treat nasal polyposis. As described in more detail below, the devices may be useful within any hollow-body organ, cavity, or vascular system.

Methods of treatment are also described here. In some variations, the method comprises advancing a device in a low-profile configuration to a target tissue area (e.g., a sinus cavity, nasal passage, or the like), and delivering the device to a target tissue. Any of the devices described herein-throughout may be delivered in this manner, and the devices may be used to treat one or more conditions (e.g., nasal polyposis, sinusitis, or the like). Additionally, at some variations the methods further comprise delivering the device in an expanded configuration. In some of these methods, the device self-expands from a low-profile configuration to an expanded configuration. In other methods, the device is manually expanded to an expanded configuration.

BRIEF DESCRIPTION OF THE DRAWINGS

FIGS. 12A and 12B depict two variations of hub extensions that may be used with the devices described here.

FIGS. 21A-21D show a variation of a delivery device for delivering the devices described here.

FIG. 22 depicts a variation of the devices described here.

DETAILED DESCRIPTION

Described here are expandable devices for placement in one or more portions of the body. Methods for treating various conditions or diseases are also described. The devices may provide support to one or more tissues, and may optionally deliver one or more drugs thereto. These devices may have utility in any area of the body that may benefit from any of the functions that the devices may provide. In some instances, the devices may be sized and configured for use in one or more nasal cavities (e.g., to compress, separate, dilate, stabilize, support and/or deliver one or more drugs to one or more nasal polyps, and/or move, hold, and/or bias the middle turbinate away from the lateral nasal wall). In other instances the devices may be sized and configured for use in one or more sinus cavities, either before or after a functional endoscopic sinus surgery. In still other variations the devices may be sized and configured for use in one or more hollow-body organs (e.g., the vasculature, ureters, urethra, bladder, and the like). Additionally described here are delivery devices and methods for using them to deliver the expandable devices described here.

Expandable Devices

The devices described here are expandable devices comprising a hub and a plurality of legs attached thereto. These expandable devices generally have at least a low-profile configuration and an expanded configuration, and may change between these configurations in any suitable manner as described below. The devices may be made out of any suitable material or materials, and may or may not be configured for drug delivery. The devices may or may not also comprise one or more biodegradable materials and thus may or may not be configured to degrade or erode over time. Indeed, the devices may be removed from the body if necessary.

Figure 1A:
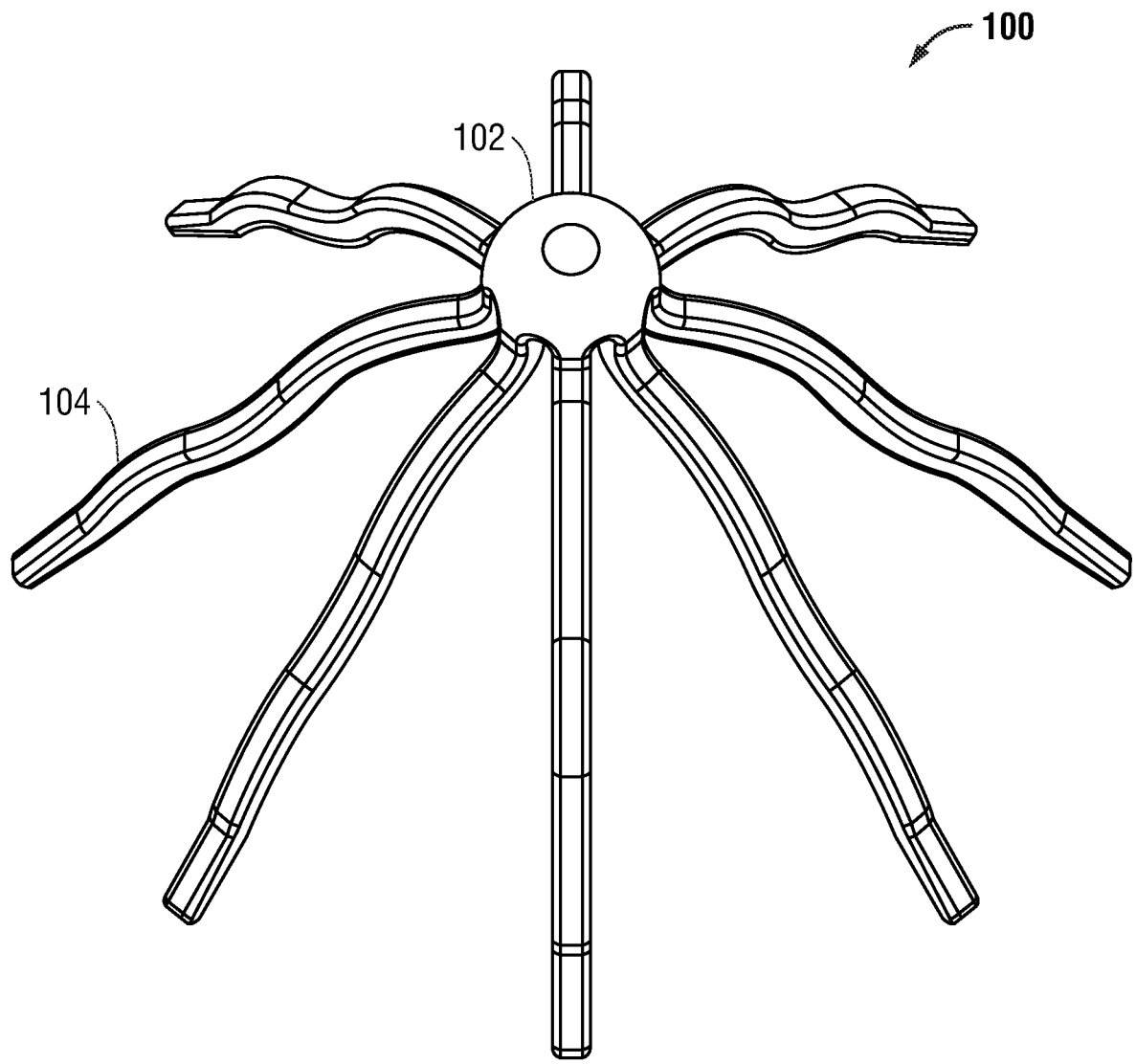
FIG. 1A is a perspective view of one variation of the devices described here.
Figure 1B:
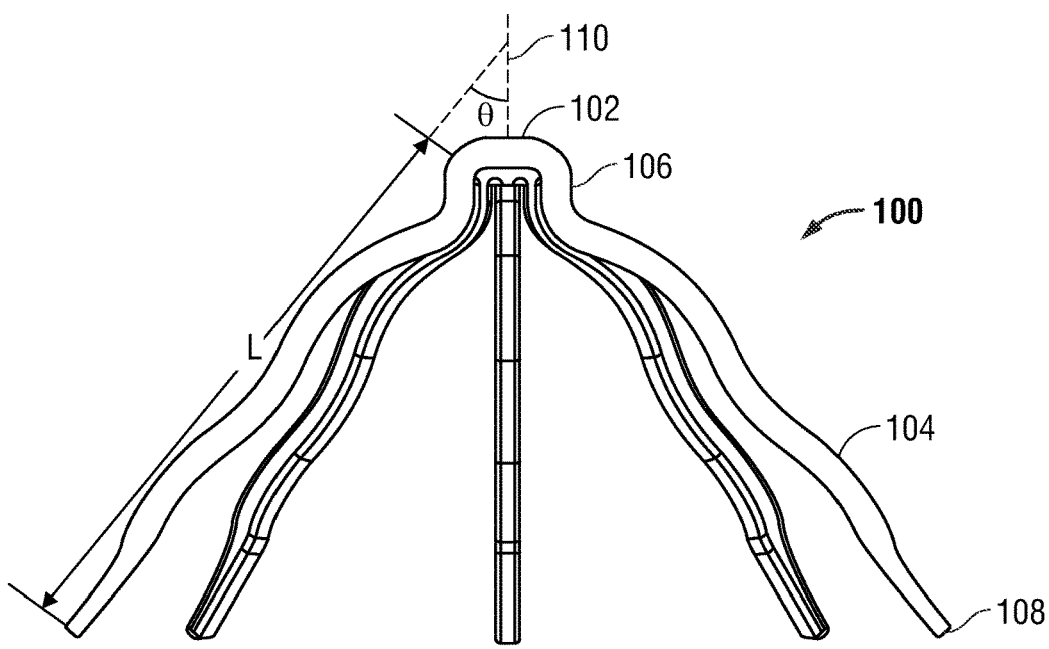
FIGS. 1B and 1D are a cross-sectional side view and a top view, respectively, of the device of FIG. 1A, shown in an expanded configuration.
Figure 1C:
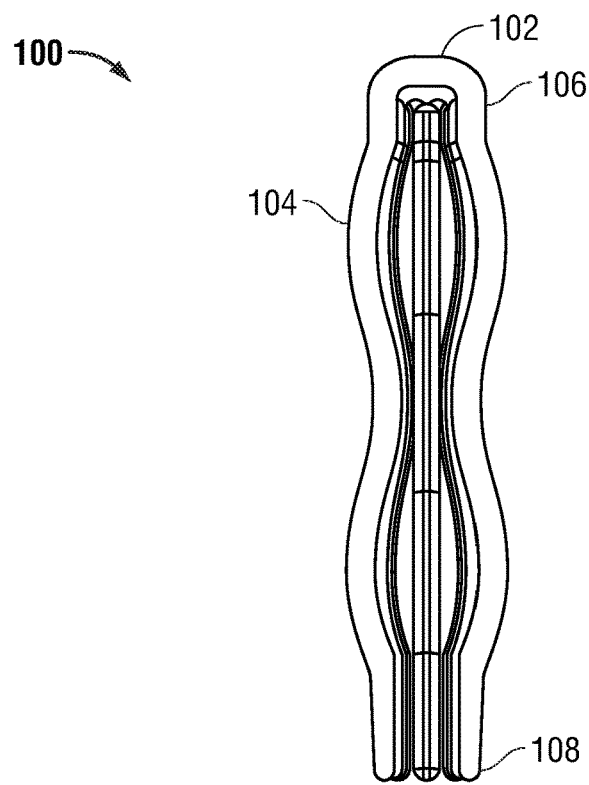
FIGS. 1C and 1E are a cross-sectional side view and a top view, respectively, of the device of FIG. 1A, shown in a low-profile configuration.
Figure 1E:
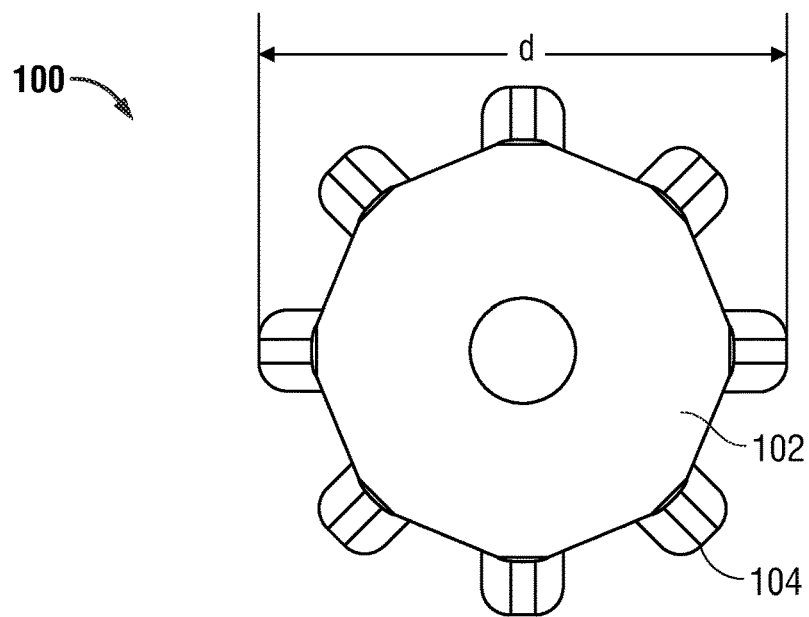
Figure 1D:
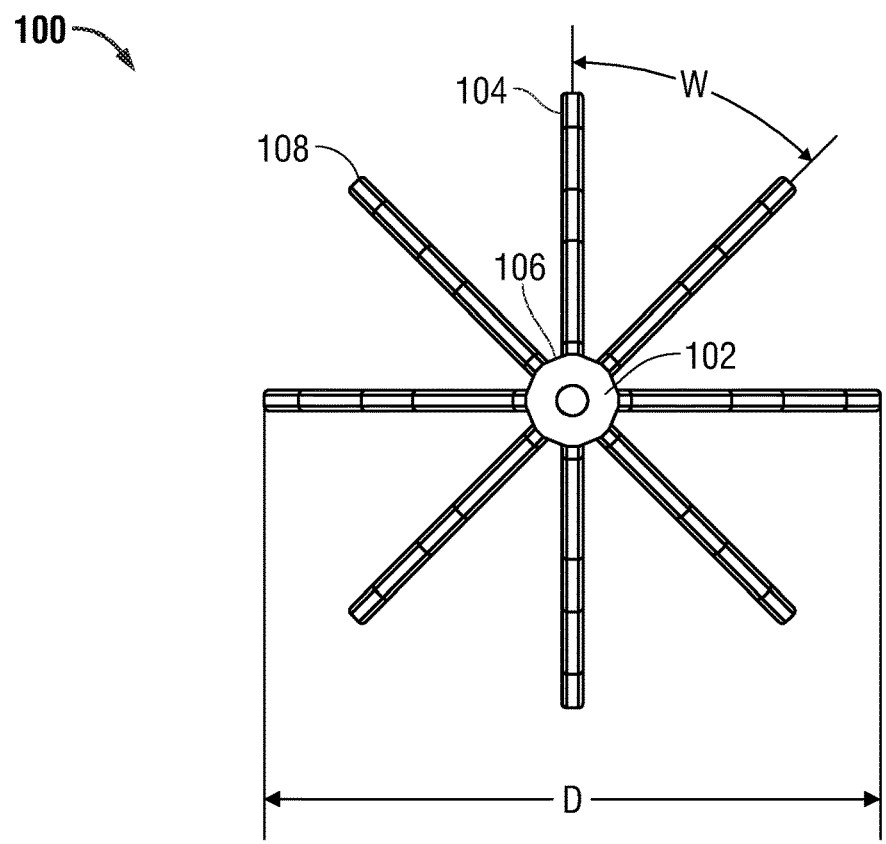

FIGS. 1A-1E illustrate a suitable variation of an expandable device (100) having an expanded configuration and a low-profile configuration. FIG. 1A shows a perspective view of device (100) in an expanded configuration. Shown there is hub (102) and a plurality of legs (104) attached to hub (102). Hub (102) and legs (104) may have any suitable size, shape, and configuration of elements, as will be described in more detail below. FIGS. 1B and 1D depict a cross-sectional side view and a top view, respectively, of device (100) in an expanded configuration. Similarly, FIGS. 1C and 1E depict a cross-sectional side view and a top view, respectively, of device (100) in a low-profile configuration.

To change device (100) between low-profile and expanded configurations (or vice-versa), one or more portions of one or more legs (104) may bend, flex, deform, or otherwise rotate relative to hub (102). A device's low-profile configuration, as depicted in FIG. 1C, may facilitate advancement of the device (100) to a target location in the body. Specifically, placing device (100) in a low-profile configuration reduces the overall transverse cross-sectional profile of the device (100), as illustrated in FIG. 1E. With this reduced profile, the device (100) may encounter less resistance from surrounding tissue as the device (100) is advanced to a target location in the body. Similarly, the reduced profile may make it easier for device (100) to move between or through two or more adjacent or touching tissue surfaces.

Conversely, when device (100) is in an expanded configuration, one or more portions of the device (100) may be configured for apposition against one or more tissues, and one or more portions of the device (100) may or may not at least partially conform to surrounding tissue or tissues. As legs (104) bend, flex, or rotate away from hub (102) to expand device (100) to an expanded configuration, each leg (104) may apply one or more forces to surrounding tissue or tissues. These forces may move, compress, dilate, or otherwise alter the shape of one or more tissues. Indeed, in some variations the legs may be configured to apply between about 0.5 Newtons and about 15 Newtons of force to surrounding tissue. In other variations, the legs may be configured to apply between about 3 Newtons and about 8

Newtons of force. It should be appreciated however, that the device may be configured such that the force or forces applied by the device is not sufficient to cause tissue damage.

It should be appreciated that the devices described here may have multiple expanded configurations. Specifically, a device may have one configuration when expanded outside of the body, and one or more different configurations when expanded inside of the body. When a device is expanded outside of the body and is free of any external forces or stimuli, the device will take on an unconstrained expanded configuration. This unconstrained expanded configuration may dependent in part upon the ambient conditions (e.g., temperature or humidity) and in part upon the device's inherent characteristics (e.g., its size, strength, glass transition temperature in devices comprising one or more polymers, etc.). When the device is expanded within the body, however, one or more tissues or other bodily structures may apply one or more forces or stimuli to the device. In some instances, these forces or stimuli do not prevent the device from expanding to its unconstrained expanded configuration. In other instances, these forces or stimuli may limit the device's ability to expand to its unconstrained expanded configuration. In these instances, the device may take on a constrained expanded configuration. The shape and dimensions of this constrained configuration may depend in part upon the device's inherent characteristics (e.g., its size, strength, glass transition temperature in devices comprising one or more polymers, etc.) and in part upon the characteristics of the surrounding tissue (e.g., tissue density, rigidity, ambient temperature, humidity etc.). A device's constrained expanded configuration may also change after delivery. In some instances, the device may shift or reposition itself within the body. In other instances, the surrounding tissue may move or change shape over time. For example, when placed in proximity to one or more nasal polyps, a device's expanded configuration may change as the nasal polyps shrink.

As mentioned above, the devices may change between low-profile and expanded configurations in any suitable manner. In some variations, the devices are self-expandable. In these variations, the devices may be crimped from an expanded configuration to a low-profile configuration, and may be advanced to a target location while held in a low-profile configuration. The device may be released at target location, at which point it may self-expand to an expanded configuration. One or more inflatable balloons or other expandable structures may or may not be expanded to help aid the expansion of a self-expandable device.

In other variations, the device may be expandable from a low-profile configuration in response to one or more forces or stimuli. In these variations, the device may be formed in a low-profile configuration, or may be crimped from an expanded configuration such that the device is plastically deformed into a low-profile configuration. The device may be advanced in a low profile configuration to a target location, at which point the device may be at least partially expanded. When the device is expanded, one or more portions may plastically deform to hold the device in an expanded configuration. In some variations, one or more forces may expand the device. These forces may or may not be provided by one or more expandable devices (e.g., a balloon, expandable cage, or the like). In other variations, the device may expand in response to one or more stimuli (e.g., heat, light, changes in pH, energy, and the like). These stimuli may or may not be produced by the body.

Each device may have any suitable dimensions. FIGS. 1B-1E illustrate some of the relevant dimensions of device (100). For example, each leg (104) may have any suitable length (L). All of the legs (104) of a particular device (100) may have the same length (L), or different legs (104) may have different lengths. Examples of suitable lengths (L) include, but are not limited to, about 20 mm, about 25 mm, about 30 mm, about 35 mm, between about 5 mm and about 35 mm, between about 10 mm and about 35 mm, between about 15 and about 35 mm, between about 20 mm and about 35 mm, between about 25 mm and about 35 mm, between about 30 mm and about 35 mm, between about 5 mm and about 30 mm, between about 10 mm and about 30 mm, between about 15 and about 30 mm, between about 20 mm and about 30 mm, between about 25 mm and about 30 mm, between about 5 mm and about 25 mm, between about 10 and about 25 mm, between about 15 mm and about 25 mm, between about 20 mm and about 25 mm, between about 5 mm and about 20 mm, between about 10 mm and about 20 mm, between about 15 and about 20 mm, between about 5 mm, and about 15 mm, between about 10 and about 15 mm, between about 5 mm and about 10 mm, between about 30 mm and about 60 mm, between about 40 mm and about 60 mm, and between about 50 mm and about 60 mm. In some variations, the choice of length (L) for one or more legs (104) may be determined, in part, by the intended delivery site for the device (100). For example, in variations where the device is placed between a lateral nasal wall and middle turbinate of a patient, the length (L) of one or more legs may be configured to be approximately the length of the middle turbinate. As shown in FIG. 1B, length (L) is measured in a straight line from the point of attachment (106) between leg (104) and hub (102) to the distal end (108) of leg (104). In variations where a leg (104) comprises one or more bends or curved segments, as described in more detail below, leg (104) may actually be longer than length (L). It should be appreciated that any of the legs described in more detail below may have any of the lengths described immediately above. Additionally, each leg may have any suitable thickness. For example, in variations where the leg comprises a polygonal cross-sectional shape (e.g., a square, rectangle, trapezoid, or the like), each side of the leg may have any suitable dimension, such as, for example, between about 0.5 mm and about 2 mm, between about 0.8 and about 1.5 mm, about 0.9 mm, about 1 mm, about 1.1 mm about 1.2, and the like. In variations where the device comprises one or more circular or oval legs, the diameter and/or the major and minor axes may have any suitable dimension, such as those immediately described above.

Furthermore, each leg (104) of the devices described here may project at an angle (θ) from the longitudinal axis (110) of device (100). This angle (θ) may change when device (100) moves between an expanded configuration, as shown in FIG. 1B, and a low-profile configuration, as shown in FIG. 1C. Angle (θ) is not shown in FIG. 1C, because this angle is approximately zero when device (100) is in its low-profile configuration. Angle (θ) is depicted in FIG. 1B, and is measured as the angle (θ) between the longitudinal axis (110) of device (100) and line used to measure length (L), as described immediately above. It is important to note that when the device (100) comprises one or more bends or curved segments, as described in more detail below, different portions of the leg (104) may actually project away from the longitudinal axis (110) at different angles. Additionally, different legs (104) may project away from the longitudinal axis (110) at different angles (θ). When device (100) is in an unconstrained expanded configuration, angle (θ) may be any suitable angle. For example, the angle (θ) may be about 15 degrees, about 20 degrees, about 25 degrees, 30 degrees, about 35 degrees, about 40 degrees, about 45 degrees, about 50 degrees, about 55 degrees, about 60 degrees, about 65 degrees, about 70 degrees, about 75 degrees, about 80 degrees, about 85 degrees, or about 90 degrees. It should be appreciated that when device (100) is delivered to the body, it may not be able to fully expand to its unconstrained expanded configuration, and thus may take on a constrained expanded configuration. In these instances, the angle (θ) for one or more legs (104) may or may not be reduced. When the device (100) is in a low-profile configuration, angle (θ) may be any suitable angle. For example, the angle (θ) may be about 0 degrees, about 5 degrees, about 15 degrees, about 20 degrees, about 25 degrees, about 30 degrees, about 35 degrees, about 40 degrees, about 45 degrees, about 50 degrees, about 55 degrees, or about 60 degrees.

Additionally, an angle (ω) may separate two neighboring legs. Although shown in FIG. 1D as being evenly spaced around the circumference of hub (102), legs (104) need not be. Indeed, different angles (ω) may separate different pairs of neighboring legs (104), although generally the sum of all of these angles will add up to 360 degrees. Any suitable angle (ω) may separate two neighboring legs (104). In the variation shown in FIG. 1D, each pair of legs is separated by a 45 degree angle. Examples of other suitable angles (ω) include, but are not limited to less than about 10 degrees, about 10 degrees, about 20 degrees, about 30 degrees, about 40 degrees, about 50 degrees, about 60 degrees, about 70 degrees, about 80 degrees, about 90 degrees, about 100 degrees, about 110 degrees, about 120 degrees, about 130 degrees, about 140 degrees, about 150 degrees, about 160 degrees, about 170 degrees, about 180 degrees, about 190 degree, about 200 degrees, about 210 degrees, about 220 degrees, about 230 degrees, about 240 degrees, about 250 degrees, about 260 degrees, about 270 degrees, about 280 degrees, about 290 degrees, about 300 degrees, about 310 degrees, about 320 degrees, and greater than 330 degrees.

The devices described here may further define a transverse profile (i.e., the profile seen when looking at the top of a device along its longitudinal axis). For example, in the variation shown in FIGS. 1D and 1E, device (100) defines an approximately circular transverse profile. It should be appreciated, however, that devices described here may have a transverse profile having any suitable shape (e.g., an oval, triangle, rectangle, polygon, a shape having irregular geometry, and the like). Additionally, this transverse profile may have any suitable size, which may change depending on whether the device is in an expanded configuration or a low-profile configuration. For example, in variations where the device has a circular transverse profile, such as device (100) shown in FIGS. 1D and 1E, this circular profile may have an expanded diameter (D) when device (100) is in an expanded configuration and a low-profile diameter (d) when device (100) is in a low-profile configuration. The ratio of the expanded diameter (D) to the low-profile diameter (d), or D:d, may be representative of how effectively the device may be crimped. This may be any suitable ratio, such as, for example, about 10:1, from about 2:1 to about 20:1, from about 2:1 to about 15:1, from about 2:1 to about 12:1, from about 2:1 to about 8:1, from about 2:1 to about 5:1, from about 5:1 to about 20:1, from about 5:1 to about 15:1, from about 5:1 to about 12:1, from about 5:1 to about 8:1, from about 5:1 to about 20:1, from about 8:1 to about 20:1, from about 8:1 to about 12:1, from about 8:1 to about 15:1, from about 8:1 to about 12:1, from about 12:1 to about 20:1, from about 12:1 to about 15:1, from about 15:1 to about 20:1, and the like. The actual values of the expanded (D) diameter will typically depend on the target site for deployment, so that appropriate tissue apposition may be effected. For example, this expanded diameter (D) may be about 30 mm, between about 15 mm and about 40 mm, between about 20 mm and about 40 mm, between about 25 mm and about 40 mm, between about 30 mm and about 40 mm, between about 35 mm and about 40 mm, between about 15 mm and about 35 mm, between about 20 mm and about 35 mm, between about 25 mm and about 35 mm, between about 30 mm and about 35 mm, between about 15 mm and about 30 mm, between about 20 mm and about 30 mm, between about 25 mm and about 30 mm, between about 15 mm and about 25 mm, between about 20 mm and about 25 mm, or between about 15 mm and about 20 mm. Conversely, the low-profile diameter (d) may be any value suitable for low-profile delivery. For example, the low-profile diameter (d) of the device in the compressed configuration may be about 6 mm, from about 2 mm to about 10 mm, from about 4 mm to about 10 mm, from about 6 mm to about 10 mm, from about 8 mm to about 10 mm, from about 2 mm to about 8 mm, from about 4 mm to about 8 mm, from about 6 mm to about 8 mm, from about 2 mm to about 6 mm, from about 4 mm to about 6 mm, from about 2 mm to about 4 mm, greater than 10 mm, and the like. It should also be understood that while the device may provide support for a given area, the device need only be in physical contact with a fraction of that area. Additionally, it should be appreciated the devices having non-circular cross-sectional profiles (such as those described above) may have similar dimensions, and may have similar ratios between expanded and low-profile configurations.

Hub

Each of the devices described here comprises a hub. In addition to acting as a junction for connecting the plurality of legs, the hub may serve a number of useful functions. In some instances, the hub's configuration may affect the distribution of stresses throughout the device when one or more forces are applied thereto, which may affect subsequent deformation of the device, as will be described in more detail below. In other variations, the hub may be configured to pierce, puncture, or penetrate one or more tissues, and may or may not be configured to at least partially anchor the device in one or more tissues. In still other instances, the hub may help facilitate advancement of the device through tissues. Specifically, when the device is advanced to a target location in the body, the hub may act to separate adjoining or touching tissues. In some instances, the hub may act to support one or more portions of the surrounding anatomy (e.g., a sinus ostium).

Figure 2A:
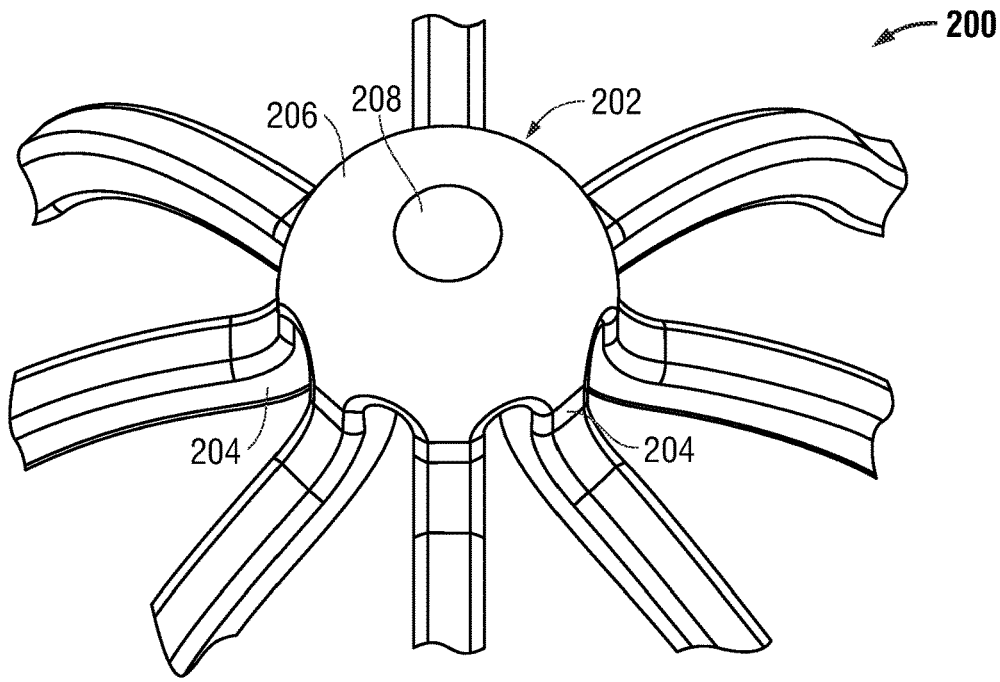
FIG. 2A is a perspective view of one suitable hub configuration that may be useful with the devices described here.
Figure 2B:
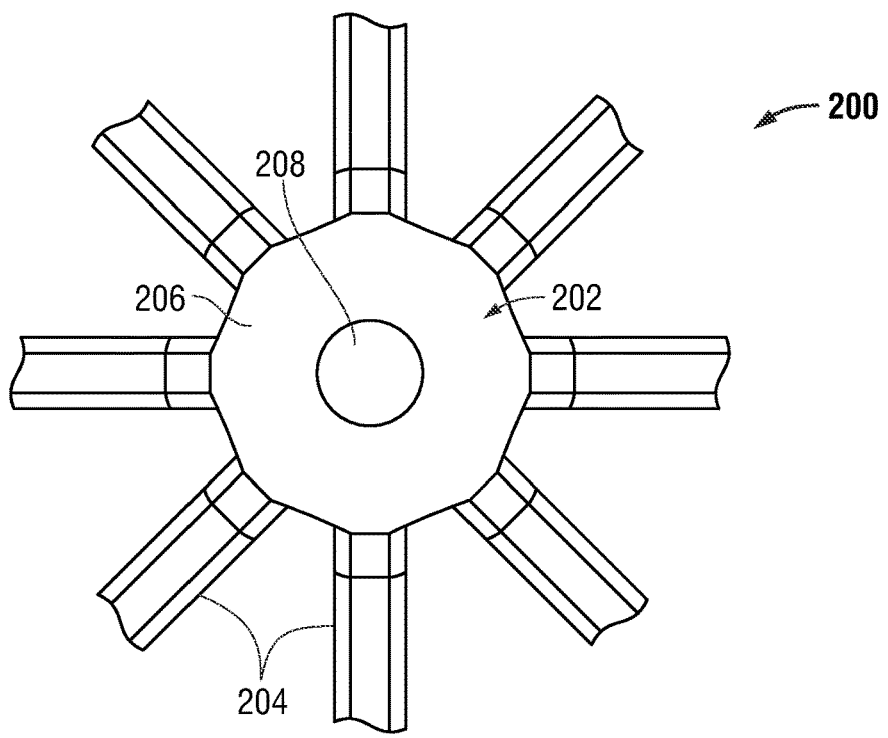
FIGS. 2B and 2C are a top view and a cross-sectional side view, respectively, of the hub of FIG. 2A.
Figure 2C:
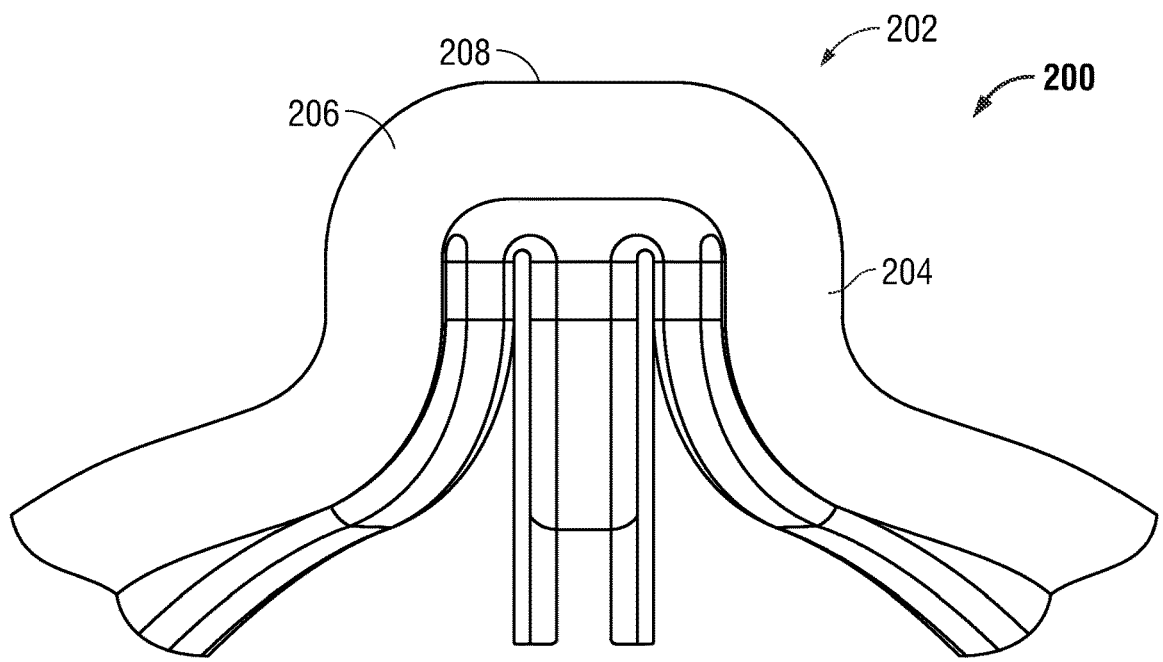

The hub may have any suitable structure with any suitable size, shape, and configuration of elements. For example, in some variations the hub may comprise or more domed surfaces, one or more cylindrical portions, one or more tapered surfaces, combinations thereof, and the like. Additionally, the hub may or may not have a uniform or substantially uniform thickness. For example, FIGS. 2A-2C illustrate a perspective view, a top view, and a cross-sectional side view, respectively, of one variation of device (200) comprising hub (202) and a number of legs (204) attached thereto. As shown there, hub (202) may comprise a domed portion (206) having a flat top (208).

While shown in FIG. 2C as having substantially uniform thickness throughout hub (202), device (200) need not comprise a hub (202) having substantially uniform thickness. In variations where the hub (202) has substantially uniform thickness, the hub (202) may act to distribute stresses evenly throughout the hub (202) when one or more forces move legs (204) between an expanded configuration and a low-profile configuration, or vice versa. Even distribution may help to reduce plastic deformation as device (200) moves between its expanded and low-profile configurations. As such, substantially uniform hub thickness may provide particular utility in instances where plastic deformation is undesirable, such as when the device (200) is configured to be self-expandable. Additionally, when the hub (202) is configured to biodegrade or erode over time, uniform hub thickness may help to provide even degradation throughout the hub.

Having non-uniform hub thickness, on the other hand, may concentrate stresses in one or more portions of the device (200). For example, in variations where the hub (202) comprises a domed portion (206) attached to legs (204) and having a flat top (208), the thickness of the flat top (208) may be less than that of the rounded portion (206). In these variations stresses may be concentrated in the flat top (208) when the device (200) moves between expanded and low-profile configurations, which may result in plastic deformation of the flat top (208). Conversely, the thickness of the domed portion (206) may be thinner toward legs (204) than at the flat top (208), and thus stresses may be concentrated near legs (204). In these variations, plastic deformation may be more likely to occur near legs (204) when the device (200) changes between expanded and low-profile configurations. This may provide particular utility in instances where the device is plastically deformed from a low-profile configuration to an expanded configuration, or vice versa.

Figure 3:
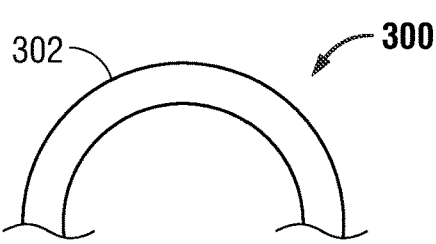
FIGS. 3, 4A and 4B depict various hub configurations that may be useful with the devices described here.
Figure 4A:
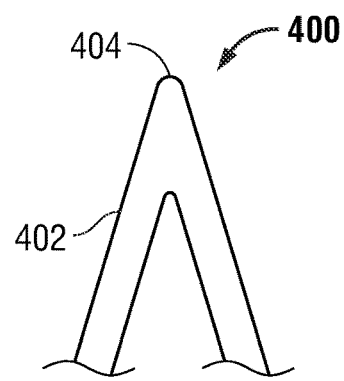

The hubs described here may have any suitable outer profile. The profile of the hub, along with the hub's thickness, may affect the distribution of stresses within the hub, which may thereby affect the flexibility and strength of the device. In some variations, a hub may comprise a domed portion attached to the legs and having a flat top, as described immediately above. In these variations, the hub's rounded surface may prevent the hub from causing damage to one or more tissues as the device is advanced through the body. In other variations, the hub has a domed portion without a flat top. FIG. 3 shows a cross-sectional side view of one such variation of hub (300) comprising a fully-domed portion (302). In other variations, the hub does not comprise a domed portion. FIG. 4A shows a cross-sectional side view of one such variation of hub (400). Shown there is hub (400) comprising a tapered portion (402). In these variations, the reduced profile near the tip (404) of hub (400) may help the hub (404) to maneuver through adjoining or touching tissues (not shown). In variations where the tip (404) is pointed, the tip (404) may help the hub (400) pierce, puncture or otherwise penetrate one or more tissues.

Figure 4B:
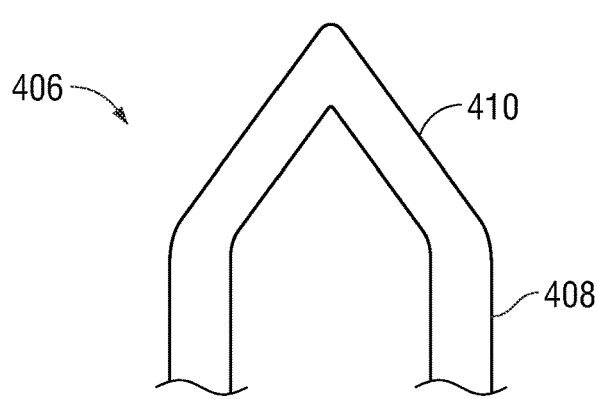

In other variations, a hub may comprise one or more extension portions. Generally, an extension portion may be a portion of hub having, a generally constant transverse cross-sectional area (i.e., the cross-sectional area seen when looking at the top of the device along its longitudinal axis), and which may increase the overall length of a hub. FIG. 4B shows one such variation of hub (406) having an extension portion (408) and a tapered portion (410). Extension portion (408) need not have a circular transverse cross-sectional shape, and may have any suitable cross-sectional shape as described in more detail below. Additionally, while shown in FIG. 4B as having a tapered portion (410) attached to the end of extension portion (408), hub (406) need not have a tapered portion (410) at all. In some variations, the extension portion defines a channel (not shown) therethrough, as described in more detail below. In other variations, an extension portion (408) may have a domed portion (not shown) attached thereto. In still other variations, an extension portion (408) may have a flat top. In yet other variations, the extension portion (408) may have an additional portion attached thereto, wherein that additional portion has a profile having irregular geometry.

As mentioned just above, a hub may have any suitable transverse cross-sectional shape (i.e., the cross-sectional shape seen from the top of the device along its longitudinal axis). In the variation shown in FIG. 2B, hub (202) has a circular transverse cross-section. The hubs described here, however, may have any suitable transverse cross-sectional shape, such as, for example, a circle, oval, triangle, square, rectangle, other polygon, shape having irregular geometries, and the like. Additionally, the hub may have any suitable dimensions. For example, in variations where the hub has a circular cross-section shape, the cross-sectional diameter may be any suitable length, such as, for example, between about 1 mm and about 7 mm, between about 2 mm and about 6 mm, between about 3 mm and about 5 mm, about 2 mm, about 3 mm, about 4 mm, about 5 mm, and the like. In some variations, this shape may change along the length of the hub. The transverse cross-sectional shape of the hub, as well as the positioning of legs on the hub, may at least partially determine the direction or directions that the legs will project away from the hub, which may affect the support provided by the device. Specifically, each leg of the devices described here generally extends away from hub in a particular direction, and that leg may push against one or more tissues in that direction. For example, the legs (204) of the variation shown in FIG. 2B are evenly spaced around hub (202), and thus may be capable of applying forces radially away from hub (202). These variations may provide particular utility where it is desirable to apply forces in all directions relative to the longitudinal axis of the device.

Figure 5:
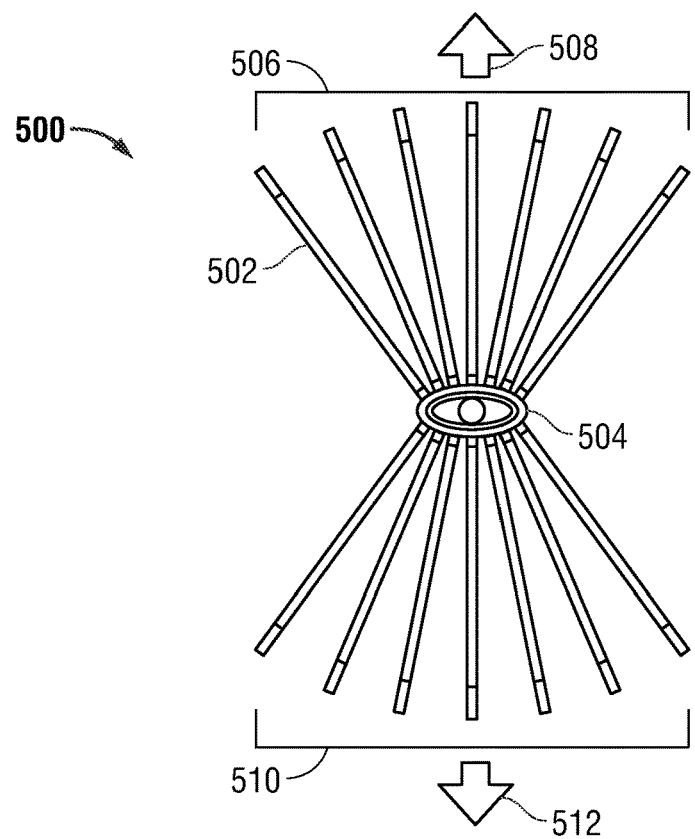
FIGS. 5 and 6 illustrate two variations of the devices described here.

FIG. 5 shows a top view of another variation of device (500) comprising a plurality of legs (502) and a hub (504) that has an oval transverse cross-sectional shape. In this variation, legs (502) are positioned such that a first set (506) of legs (502) generally projects away from hub (504) in a first direction (508) and a second set (510) of legs (502) generally projects away from hub (502) in an second direction (512). As such, the legs (502) will apply forces mainly in the first (508) and second (512) directions. Such a variation of device (500) may find particular utility in instances where it is desirable to separate two opposing tissues (e.g., when it is desirable to move and/or hold the middle turbinate away from the nasal wall, as will be described in more detail below).

Figure 6:
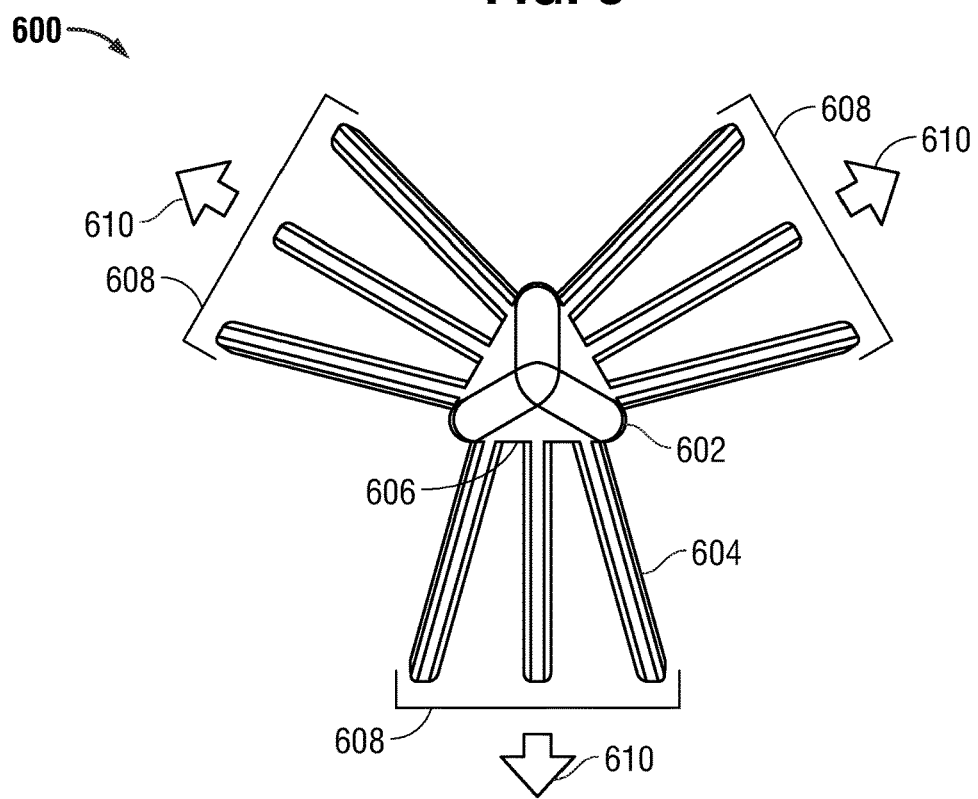

Similarly, devices described here may be configured to contact or displace one or more tissues in any suitable number of directions (e.g., three, four, or five or more). For example, a hub having a triangular transverse cross-section may be configured to direct legs in three different directions. FIG. 6 shows a top view of one such variation of device (600) having a hub (602) with a triangular transverse cross-section and a plurality of legs (604) attached thereto. Each side (606) of hub (602) may have a set (608) of legs (604) attached thereto. Each set (608) of legs (604) may be oriented in a particular direction (610), and thus device (600) may be configured to contact or displace tissue mainly in three different directions. A hub with a rectangular cross-section may similarly be configured to touch or displace tissue mainly in four directions, a hub with a pentagonal cross-section may be configured to touch or displace tissue mainly in five directions, and the like. It is important to note that is these variations a set of legs need not be attached to every side of a polygonal hub. For example, in variations where the hub has a rectangular transverse cross-section, only two or three sides may have a set of legs, and thus the hub may be configured to touch or displace tissue mainly in two directions or three directions, respectively.

In some variations, a hub may have one or more spaces (e.g., a channel, slot, a passageway and the like) extending at least partially through one or more surfaces of the hub. These spaces may serve a number of useful functions. In some variations, one or more drug-releasing substances may be placed in the one or more spaces, thereby turning the one or more spaces into drug-releasing depots. In other variations, at least a portion of one or more additional elements (e.g., the delivery devices and hub extensions described below) may be permanently or temporarily placed in the one or more spaces. In variations where the space or spaces extends entirely through one or more surfaces of the hub, the space may allow for fluid flow or drainage therethrough. In variations where the hub is biodegradable, degradable, or otherwise erodible, the spaces may affect the degradation of the hub, as will be described in more detail below.

Figure 7A:
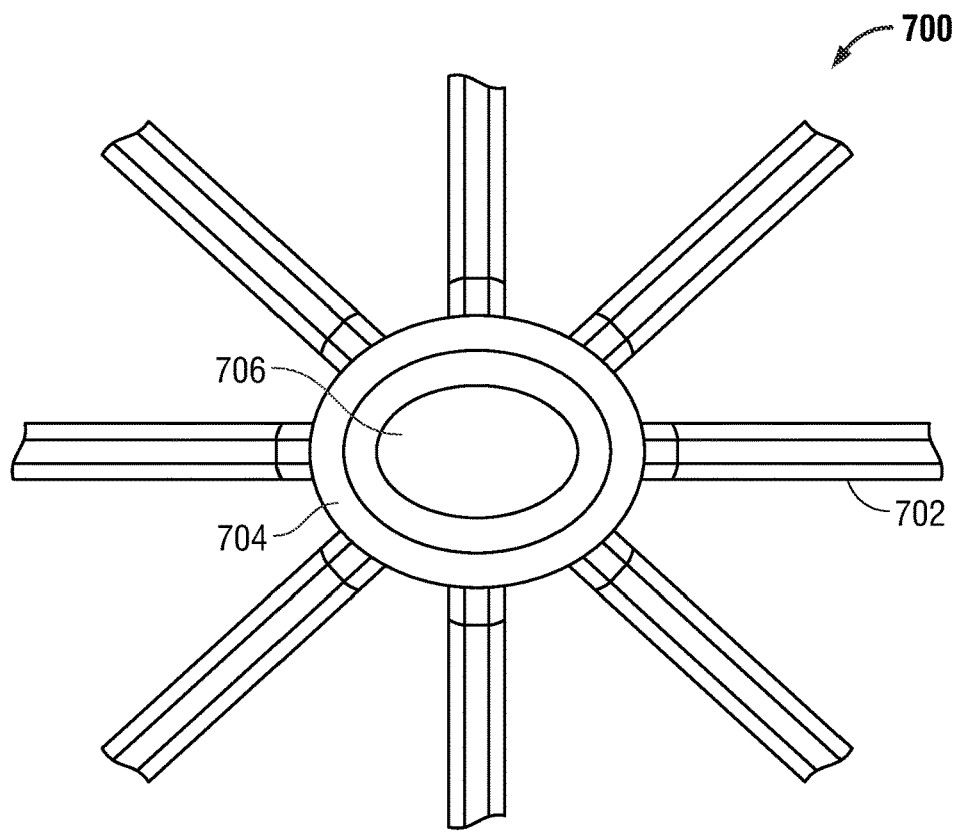
FIGS. 7A and 7B illustrate two variations of hub configurations that may be useful with the devices described here.
Figure 7B:
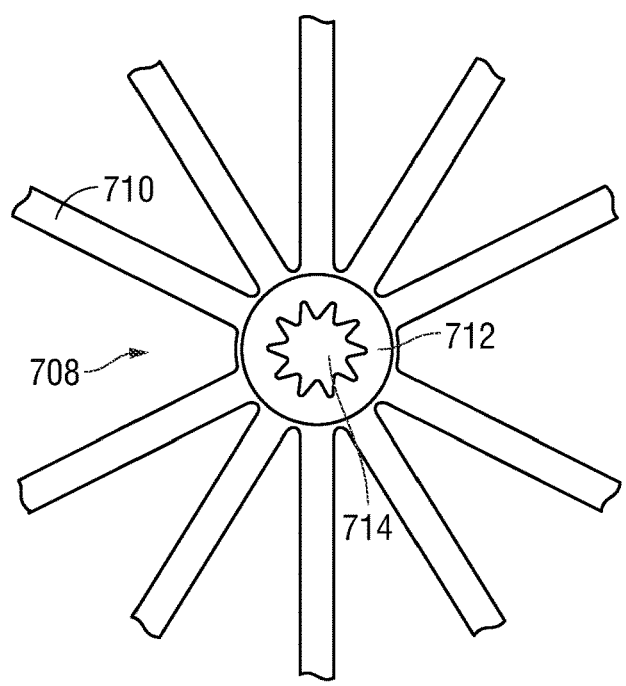

FIG. 7A shows a top view of one such variation of device (700) comprising a plurality of legs (702) and a hub (704) that has a channel (706) passing therethrough. While shown in FIG. 7A as being oval, channel (706) may have any suitable shape. Indeed, a channel (706) may be a circle, an oval, a triangle, a rectangle, a polygon, a star, a shape with irregular geometry, or the like. Additionally, the shape of the channel (706) may be the same as the transverse cross-sectional shape of hub (704), but need not. FIG. 7B illustrates one such variation of device (708) comprising a plurality of legs (710) and a hub (712) that has a circular transverse-cross section. Also shown there is a star-shaped channel (714) passing through hub (712).

Legs

The expandable devices described here also comprise a plurality of legs. A given device may comprise any number of legs. Indeed, in some variations the device may comprise two, three, four, five, six, seven, eight, nine, ten, eleven, or twelve or more legs. The device's legs may have any suitable size, shape, and configuration of elements, as described in more detail below. Each individual leg need not, however, have the same size, shape, and configuration of elements. Indeed, different legs on an expandable device may have different sizes, different shapes, and/or different configurations of elements. Additionally, a leg may be attached to any portion or surface (e.g., top, side, bottom or the like) of a hub or other leg.

Figure 8A:
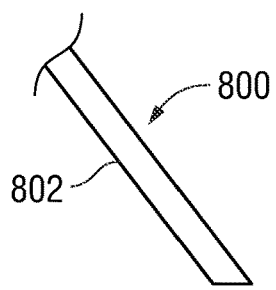
FIGS. 8A-8I depict various leg configurations suitable for use with the devices described here.
Figure 8B:
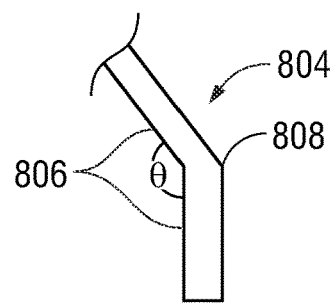

Each leg generally comprises some combination of straight segments, curved segments, and/or bends. FIGS. 8A-8I illustrate several variations of legs suitable for use with the expandable devices described here. In some variations the leg comprises only straight segments. FIG. 8A illustrates one such variation of leg (800) comprising straight segment (802). Leg (800) may comprise any number of straight segments (e.g., zero, one, two, three, or four or more straight segments). FIG. 8B shows one such variation of leg (804) comprising two straight segments (806) connected at bend (808). Straight segments (806) may be connected at any suitable angle (θ). Examples of suitable angles include, but are not limited to, at least about 170 degrees, about 160 degrees, about 150 degrees, about 140 degrees, about 130 degrees, about 120 degrees, about 110 degrees, about 100 degrees, about 90 degrees, about 80 degrees, about 70 degrees, about 60 degrees, about 50 degrees, about 40 degrees, about 30 degrees, about 20 degrees, and less than about 10 degrees. While shown in FIG. 8B as connected by a bend (808), straight segments (806) may be connected by one or more curved segments, as will be described in more detail below.

Figure 8C:
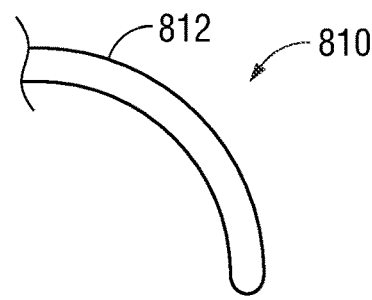
Figure 8D:
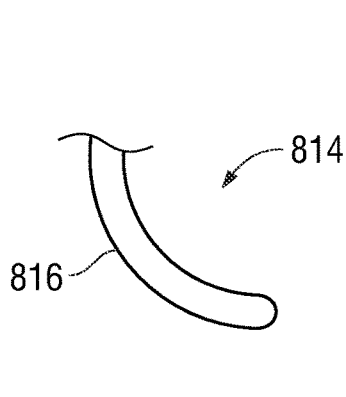

In other variations, the legs may comprise one or more curved segments. In some of these variations, the leg may comprise one or more inwardly-curved segments. FIG. 8C illustrates one such variation of leg (810) comprising an inwardly-curved segment (812). In other variations, the leg may comprise one or more outwardly-curved segments. FIG. 8D shows one such variation of leg (814) comprising an outwardly-curved segment (816). It yet other variations the legs may comprise one or more lateral curves (e.g., sections that curves in a lateral direction relative to the leg). It should be appreciated, however, that inwardly-curved and outwardly-curved segments may also at least partially curve in a lateral direction.

Figure 8E:
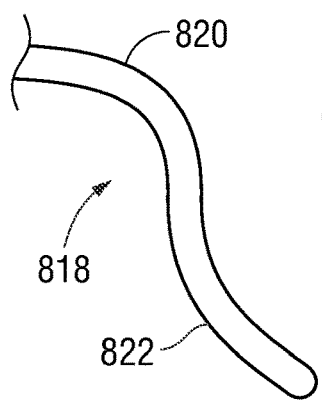

In some variations, the leg may comprise two or more curved segments. FIG. 8E shows one such variation of leg (818) comprising an inwardly-curved segment (820) and an outwardly-curved segment (822). While shown in FIG. 8E as having two curved segments, leg (818) may comprise any number of curved segments (e.g., one, two, three, four, or five or more curved segments), and each curved segment may be curved either inwardly, outwardly, or laterally. Additionally, each curved segment may have any suitable radius of curvature. Different curved segments may or may not have the same radius of curvature.

Figure 8F:
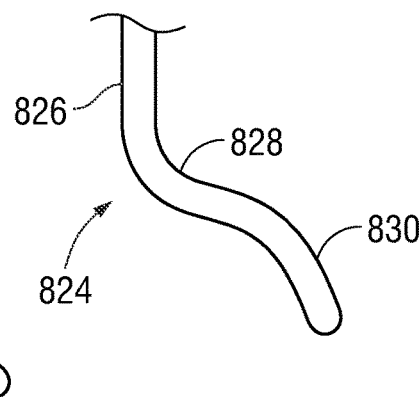

In still other variations, a leg may comprise both straight and curved segments. In these variations, as leg may comprise any number of straight segments (e.g., one, two, three, four, or five or more straight segments) and any number of curved segments (e.g., one, two, three, four, or five or more curved segments). The curved segments may be inwardly-curved segments, outwardly-curved segments, laterally-curved segments or a combination thereof. Additionally, the straight and curved segments may be connected in any suitable order. FIG. 8F shows one such variation of leg (824) comprising a straight segment (826) attached to a hub (not shown), an outwardly-curved segment (828) attached to the straight segment (826), and an inwardly-curved segment (830) attached to the outwardly-curved segment (828). Having a straight segment (826) attached to a hub may increase the flexibility of legs (824) when the legs (824) are moved from an expanded configuration to a low-profile configuration. More specifically, the straight segment (826) may act as a moment arm for forces applied to the leg (824). When a force is applied to the leg (824) of a device, a torque (i.e., a rotational force) may be applied at the junction between leg (824) and hub (not shown). This torque is proportional to the distance between the force and the junction (i.e., the moment arm). Thus increasing the length of straight segment (826) may increase the amount of rotational force placed on the junction, which may increase the tendency of leg (824) to rotate relative to the hub.

Figure 8G:
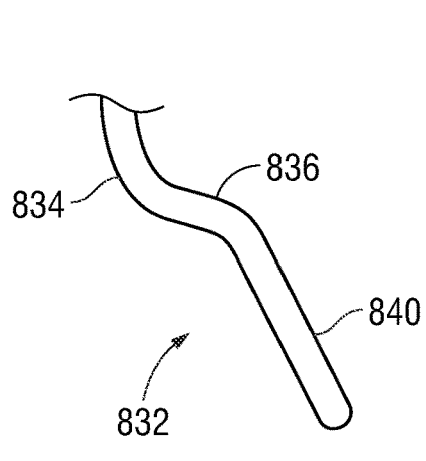
Figures 8H, 8I:
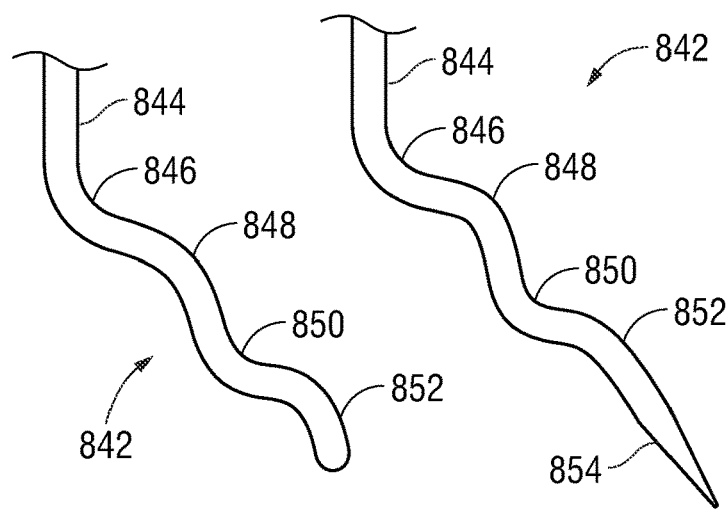

FIG. 8G shows another variation of leg (832) comprising an outwardly-curved segment (834) attached to a hub (not shown), an inwardly-curved segment (836) attached to the outwardly-curved segment (834), and a straight segment (840) attached to the inwardly-curved segment (836). FIG. 8H illustrates yet another variation of leg (842). Shown there is a first straight segment (844) attached to a hub (not shown), a first outwardly-curved segment (846) attached to the first straight segment (844), a first inwardly-curved segment (848) attached to the first outwardly-curved segment (846), a second outwardly-curved segment (850) attached to the first inwardly-curved segment (848), and a second inwardly-curved segment (852) attached to the second outwardly-curved segment (850). FIG. 8I shows the leg (842) of FIG. 8H additionally comprising a second straight segment (854) attached to the second inwardly-curved segment (852). Generally, the selection and ordering of straight and curved segments, as well as the size of each segment, may determine the overall profile defined by a leg, which may in turn affect the transverse profile of the entire device (in both expanded and low-profile configurations).

Figure 9A:
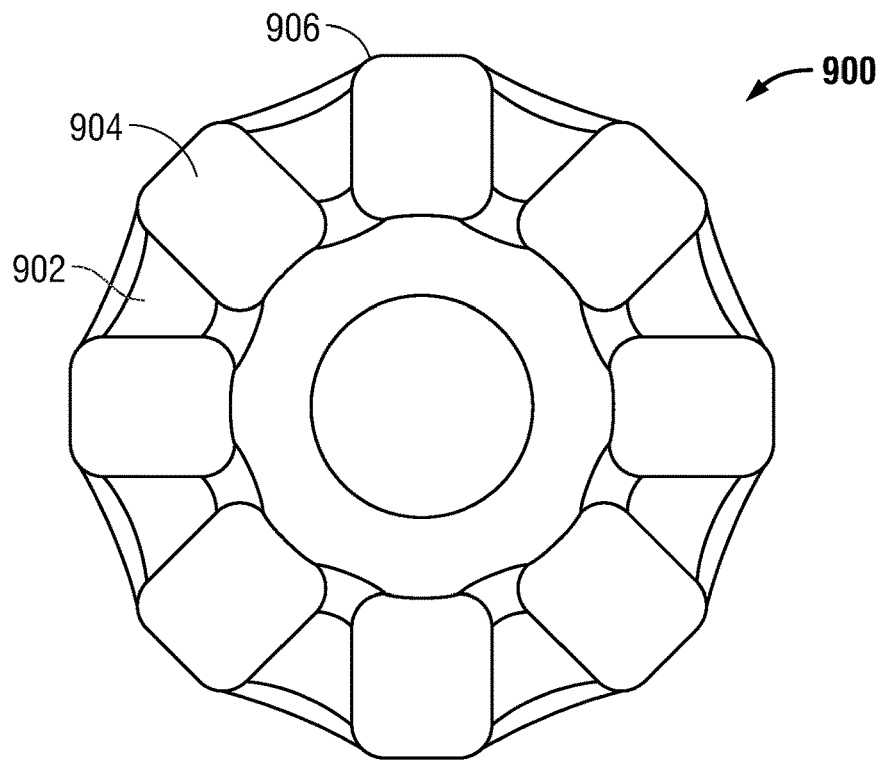
FIGS. 9A and 9B are cross-sectional bottom views of two variations of the devices described here.
Figure 9B:
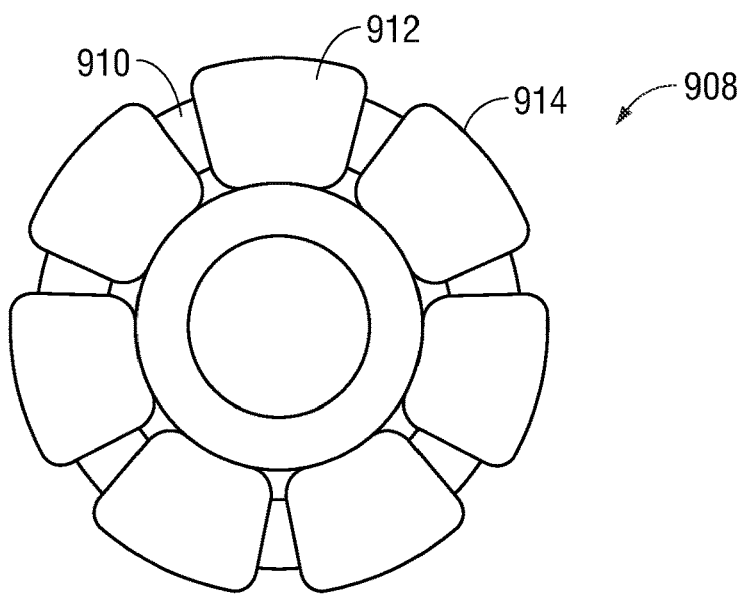

Each leg may have any suitable cross-sectional shape. For example, FIG. 9A shows a cross-sectional bottom view of one variation of device (900) comprising hub (902) and legs (904). The view in FIG. 9A cuts through legs (904) to reveal their cross-sectional shape. While shown there as having a square cross-sectional shape, legs (904) may have any suitable cross-sectional shape (e.g., a circle, oval, triangle, square, rectangle, trapezoid, rhomboid, polygon, a shape with irregular geometry, or the like). In variations where one or more legs have a polygonal cross-section shape, the cross-sectional shape may or may not have rounded edges, such as rounded edges (906) of leg shown in FIG. 9A. FIG. 9B shows a cross-sectional bottom view of another variation of device (908) comprising hub (910) and a plurality of legs (912), each having a trapezoidal cross-sectional shape.

The cross-sectional shape of the legs may affect the flexibility of the leg, as well as the deformability of the legs. Specifically, wider portions of a leg may be more resistant to movement and less likely to deform upon movement of the leg. For example, the trapezoidal legs (912) shown in FIG. 9B are narrower toward the longitudinal axis of device (908) and wider toward the outer surface (914) of legs (912). In these variations, the wider portion of the legs may resist expansion of the legs (912) to an expanded configuration. As such, it may be easier to crimp device (908) to a low-profile configuration than its to expand device (908) to an expanded configuration. Additionally, legs (912) may be more likely to plastically deform when they are crimped as opposed to when they are expanded. Conversely, because the width of legs (904) shown in FIG. 9A are constant throughout the leg (904), the legs (904) may provide the same resistance to crimping and expansion.

While shown in FIGS. 9A and 9B as having the same cross-sectional shape for every leg, a device may have legs with different cross-sectional shapes. For example, a device may have a number of legs (e.g., one, two, three, of four or more) having a rectangular cross-sectional shape and a number of legs (e.g., one, two, three, or four or more) having a trapezoidal cross-sectional shape. Furthermore, for a given leg, the cross-sectional shape of that leg may change along its length. For example, in some variations a leg may have a one or more segments having a trapezoidal cross-sectional shape, and one or more portions having a rectangular cross-sectional shape. Similarly the cross-sectional area of a leg may vary along its length. For example, in some variations the thickness or width of a leg decreases from one end of the leg to the other. When at least a portion of a leg is biodegradable, this may help to provide directional degradation of that leg. Specifically, the thinner portions of a leg may degrade faster than the thicker/wider portions. In some of these variations, a leg may be thinner at its distal end and thicker at its union with a hub. In these variations, the directional degradation from the distal end to the junction may help to prevent the legs from prematurely breaking off from the hub.

Figure 10:
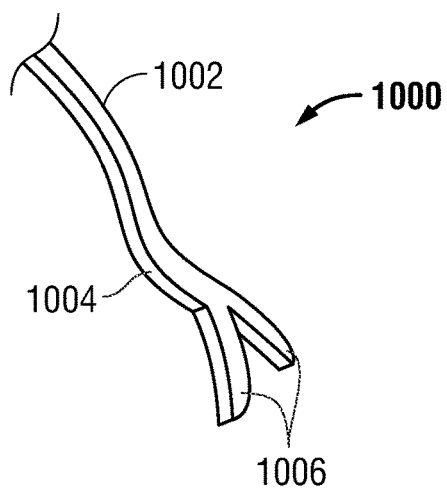
FIG. 10 depicts a variation of a leg comprising a bifurcated portion.
Figure 11A:
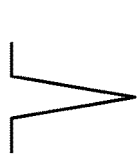
FIGS. 11A-11L depict various anchoring features for use with the devices described here.
Figure 11B:
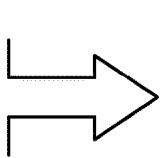
Figure 11C:
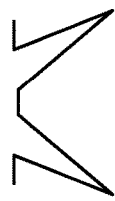
Figure 11D:
Figure 11E:
Figure 11F:
Figure 11G:
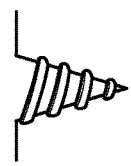
Figure 11H:
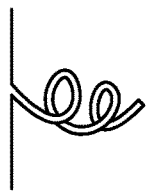
Figure 11I:
Figure 11J:
Figure 11K:
Figure 11L:
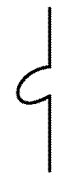

In some variations, a leg may comprise a bifurcated portion. FIG. 10 shows one such variation of a bifurcated leg (1000) comprising an inwardly-curved segment (1002) attached to a hub (not shown), an outwardly-curved segment (1004) attached to inwardly-curved segment (1002), and two straight prongs (1006) attached to outwardly-curved segment (1004). Although shown in FIG. 10 as having two prongs (1006), leg (1000) may comprise any number of prongs (e.g., two, three, four, or five or more prongs). Additionally, while shown in FIG. 10 as being straight, prongs (1006) may be curved (e.g., inwardly-curved, outwardly-curved, laterally-curved, combinations thereof). In some variations, prongs (1006) may comprise some combination of inwardly-curved, outwardly-curved, laterally-curved and straight segments, as described in more detail above. Furthermore, one or more prongs (1006) may or may not be angled away from the rest of leg (1000). When angled away from the rest of leg (1000), the prongs (1006) may push into surrounding tissue when the device (not shown) is in an expanded configuration, which may help keep the device in place at a target location. Generally, bifurcating, trifurcating or otherwise splitting a leg (1000) may increase the tissue-surface contact area.

Additional Features

The devices described here may include one or more additional features. In some variations, the devices described here comprise one or more anchoring components. The devices need not include one or more anchoring components, as the profile of the legs themselves may help to anchor the device in place. In variations that do include one or more anchoring components, these anchoring components may be any suitable structures. Indeed, FIGS. 16A-16L illustrate several suitable anchoring components, including one or more spikes (11A), arrows (11B), opposed spikes (11C), barbs (11D), hooks (11E), triangular ridges (11F), screws (11G), springs (11H) and the like. In variations that include ridges, the ridges may be formed to be round (11I), square (11J), directionally oriented or deployed ((11K) which can be inserted as a flat ridge and deploys directionally upon pulling the device backwards or proximally against the direction of insertion), concave (as in (11L), but also including other concave variations of the aforementioned convex and protruding shapes which may provide active anchoring attributes by encouraging tissue ingrowth). Furthermore, combinations of any number or all of the aforementioned anchoring features may also be used in the expandable devices. Any portion of the device (e.g., the hub, one or more legs, a combination thereof, etc.) may include one or more anchoring features. In some variations, the distal ends of one or more legs comprise one or more anchoring components attached thereto.

In other variations, the devices may comprise one or more hub extensions. Generally, a hub extension is a structure that may be at least temporarily or permanently attached to a hub to change the outer profile of the hub. A hub extension may be attached to a hub in any suitable manner. For example, a hub extension may be joined to a hub using welding (e.g., heat welding, ultrasonic welding, tacking, staking, and the like), adhesives (glues, adhesive polymers, and the like), polymers (e.g., low melting-temperature polymers and the like), sutures, clamps, clips, other mechanical fasteners, chemical bonding, or some combination thereof. In some variations, one or more portions of the hub extension may be configured to fit at least partially around an outer surface of the hub. In variations where the hub comprises one or more slots, channels or passageways, hub extension may comprise one or more structures configured to at least partially fit within one or more of the hub's slots, channels, or passageways.

FIG. 12A illustrates one such variation of hub extension (1200) comprising a pyramidal cap (1202). Such a hub extension (1200) may give a device (not shown) a tapered profile, but may do so without affecting the distribution of stresses within the device or without otherwise affecting the strength of the device. In some variations, the hub extension (1200) may help the device to pierce, puncture, or otherwise penetrate one or more tissues. In other variations, a hub extension (1200) may help to anchor a device to one or more tissues. FIG. 12B illustrates one such variation of hub extension (1204), comprising a cone-shaped portion (1206), an attachment portion (1208), and threading (1210). The cone-shaped portion may be useful in navigating through narrow tissue spaces or may aid in piercing, puncturing, or otherwise penetrating tissues. Threading (1210) may allow the hub extension (1204) to be "screwed" into tissue such that the threading (1210) engages tissue. This engagement between the threading (1210) and tissue may help to prevent the hub extension (1204), and with it, the device, from being pulled out of the tissue. While shown in FIG. 12B as having threading (1210), hub extension may comprise any suitable anchoring feature, such as those described above. Additionally, while shown in FIG. 12B as having an attachment portion (1208), hub extension (1204) need not. In variations that do have an attachment portion (1208), attachment portion may be any suitable structure capable of fitting within one or more channels, slots, or passageways in the hub (not shown).

In some variations, a hub extension may be an expandable structure, such as, for example, a balloon. In variations where the hub extension comprises a balloon, the balloon may be inflated prior to delivery of the device, and may act similarly to the hub extensions described above. In other variations, the balloon may be inflated during delivery of the device. In these variations, the balloon may be inflated to dilate, expand, move or otherwise reconfigure one or more tissues. Once the device has been delivered to the body, the balloon may or may not be deflated. In some variations, the balloon may be filled with one or more drug-containing solutions, and the one or more drug-containing solutions may elute from the balloon over time.

In other variations of the devices described here, the devices comprise one or more membranes, meshes, or films. In these variations, the membrane, mesh, or film may span at least a portion of the space between two or more legs. FIG. 22A shows a side view of one such variation of device (2200). Shown there is hub (2202) with a plurality of legs (2204) and a mesh (2206) attached to legs (2204). Mesh (2206) may be attached to legs (2204) and/or hub (2202) in any suitable manner, such as by using welding (e.g., heat welding, ultrasonic welding, tacking, staking, and the like), adhesives (glues, adhesive polymers, and the like), polymers (e.g., low melting-temperature polymers and the like), sutures, clamps, clips, other mechanical fasteners, chemical bonding, or some combination thereof. In other variations, the legs (2204) may pass through one or more pores in the mesh (2206). In other variations, the mesh (2206) comprises one or more pockets (not shown) into which one or more legs (2204) may be placed.

While shown in FIG. 22A as being attached to the interior surfaces (not shown) of legs (2204), mesh (2206) may be attached to any surface or surfaces of the device (2200). Additionally, while shown in FIG. 22A as being one continuous piece of mesh (2206), any number of mesh pieces may be connected to device (2200). For example, in some variations, a different piece of mesh (2206) may be used to connect each neighboring pair of legs. The mesh (2206) may be made from any suitable material, and may or may not be configured to biodegrade or erode over time. The mesh (2206) may or may not be stretchable or expandable, and may or may not be configured to release one or more drugs therefrom. Additionally, in some variations, the mesh may be configured for tissue ingrowth.

Furthermore, while shown in FIG. 22A as being a mesh (2206), and suitable element may connect two or more legs (2204). Examples of suitable elements include, but are not limited to, sutures, threads, cords, and fibers. In variations where a fiber (not shown) connects two or more legs (2204), the fiber may help to expand device (2200) from a low-profile to an expanded configuration. Additionally, a fiber may help to hold device (2200) in an expanded configuration.

In variations where the device comprises one or more membranes, meshes, films or other element connecting two or more legs, these structures may provide one or more useful functions. In variations where these structures are configured to release one or more drugs therefrom, the structures may increase the surface area of tissue to which one or more drugs are delivered. In other variations, the structures may apply one or more forces to surrounding tissue when the device is placed in the body. For example, when a device is placed in a nasal cavity, a mesh between two legs may act as a net to catch and move one or more nasal polyps located between the legs.

Figure 23A:
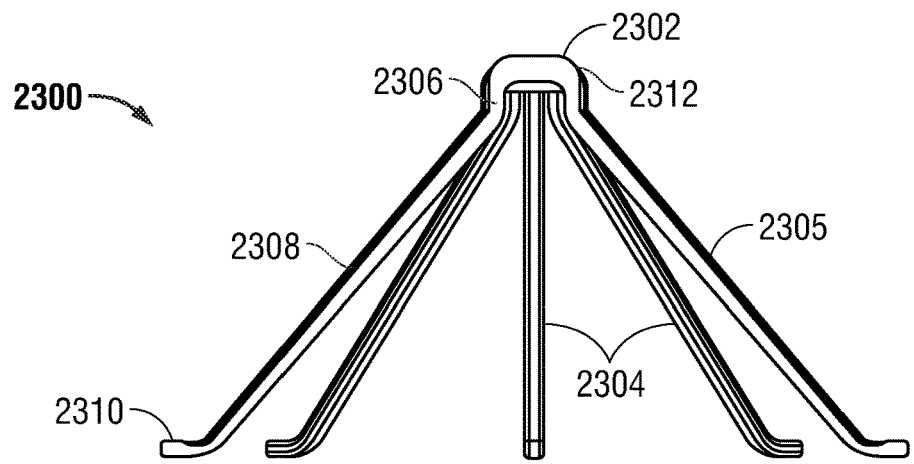
FIGS. 23A-23C, 24A and 24B depict two variations of the devices described here.
Figure 23B:
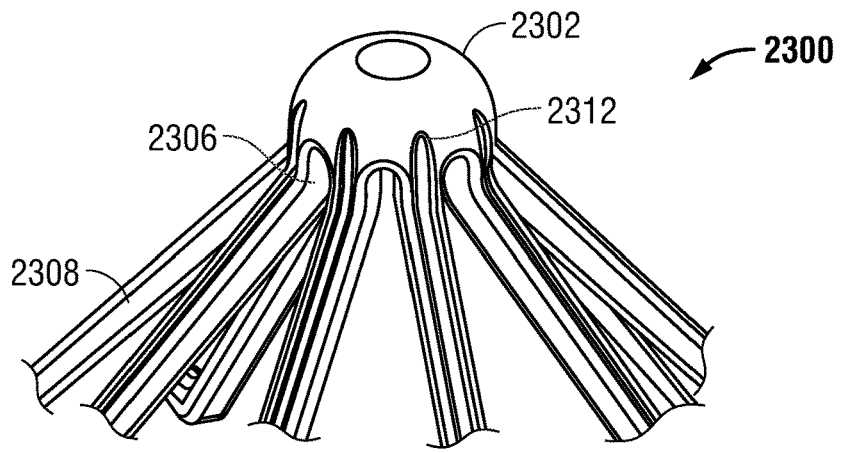
Figure 23C:
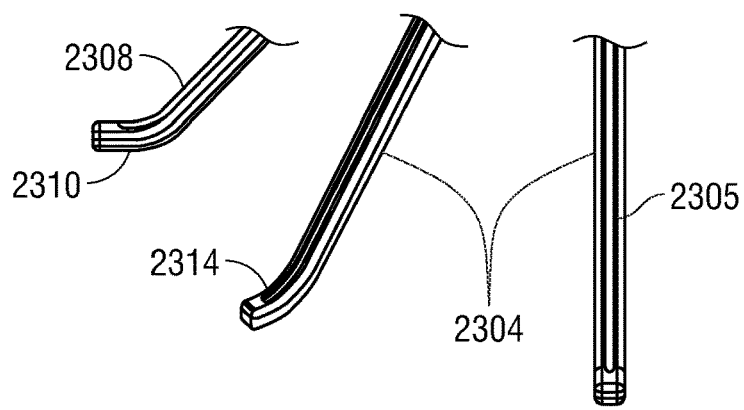

As mentioned briefly above, in some variations of the devices described here the devices may comprise one or more holes, channels, slots, passageways, impressions or other spaces extending at least partially through a surface thereof. Any portion or portions of the device (e.g., the hub an or one or more legs) may have one or more of these spaces. For example, in some variations, one or more of the legs may comprise a channel along a length thereof. For example, FIGS. 23A-23C illustrate one such variation of device (2300). FIG. 23A shows a cross-sectional side view of device (2300), comprising hub (2302), legs (2304), and longitudinal channels (2305) along a portion of legs (2304) and hub (2302). Similarly, FIG. 23B shows a partial perspective view of device (2300), while FIG. 23C shows another partial perspective view of a portion of the legs (2304) of device. Although shown in FIGS. 23A-23C as having legs (2304) each having a first curved segment (2306), first straight segment (2308), second curved segment (2309), and a second straight segment (2310), it should be appreciated that device (2300) may comprise any legs or combinations of legs described hereinthroughout. Additionally, while shown in FIGS. 23A-23C as having a hub (2302) with a domed portion (2304), device (2300) may comprise any suitable hub (2302), such as those described hereinthroughout. The longitudinal channels (2305) may have any suitable cross-sectional shape (e.g., rectangular, square, semi-circular, semi-oval, triangularly-cut, or the like) and may serve one or more useful functions. By reducing the overall cross-sectional area of legs (2304) and hub (2302), longitudinal channels (2305) may speed up or otherwise alter the degradation time of these portions of device (2300), and may do so without substantially altering the strength of the legs (2304) Additionally, the longitudinal channels (2305) may increase the overall surface area of device, which may provide for altered drug-delivery in variations where device (2300) comprises one or more drug-releasing coating layers or is otherwise configured to release one or more drugs therefrom. Indeed, in some variations, the longitudinal channels (2305) may act as a reservoir in which one or more drug-releasing substances may deposited.

Figure 24B:
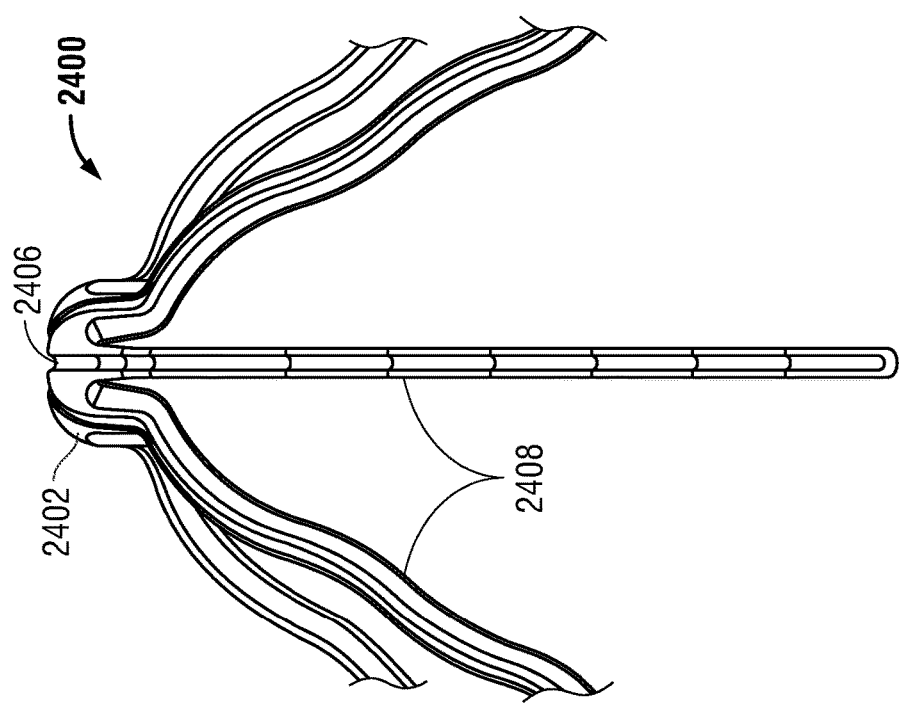
Figure 24A:
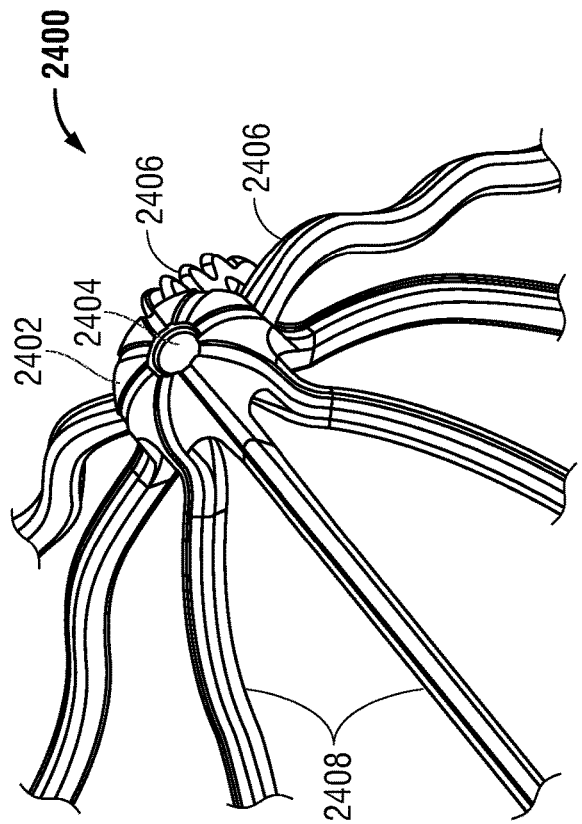

In variations that comprise channels, the channels may be disposed in any suitable surface of the device. In some variations, one or more channels may extend along a portion of the hub and one or more legs. For example, in the variation of device (2300) shown in FIGS. 23A-23C, each longitudinal channel (2305) extends between a first end (2312) in hub (2302) and a second end (2314) in second straight segment (2310) of leg (2304). In other variations, one or more longitudinal channel may span the entire length of the device. For example, FIGS. 24A and 24B show a partial perspective view and a partial side-view, respectively, of one such variation of device (400). Shown there is hub (2402) with a circular channel (2404) and a plurality of longitudinal channels (2406) extending therefrom. In this variation, each longitudinal channel (2406) may extend from circular channel (2404) along the entire length of one of the legs (2408), as shown in FIG. 24B. In yet other variations, a channel may extend along only a portion of one or more legs, or along only a portion of the hub.

In some variations, a leg may comprise two or more separate channels. In these variations, the channels may extend along any surface or surfaces of the legs. For example, in variations where a leg has a polygonal cross-sectional shape (e.g., rectangular, trapezoidal, or the like), channels may extend along different sides of the leg. For example, in some variations two channels extend along opposite sides of a leg. In variations where the leg is rectangular and the two channels have a rectangular cross-section, the leg may take on an "I-beam" type configuration. Additionally or alternatively, two or more channels extend along the same side of the leg. The two or more channels may extend in a side-by-side configuration along the leg, may extend sequentially along the leg, or combinations thereof. It should be appreciated in these variations that each leg need not comprise a channel or the same configuration of channels. For example, in some variations some legs of the device may comprise one or more channels while other legs do not.

Additionally, although shown in FIGS. 23A-23C, 24A and 24B as extending along the longitudinal length of the devices, the channels may extend in any suitable directions or directions. For example, the channels may be angled relative to the longitudinal length of the device. Indeed, in some variations one or more channels may be substantially transverse to the longitudinal length of the device. For example, in some variations, the hub of the device may comprise one or more channels that at least partially circumscribes the hub.

Similarly, other spaces (slots, holes, impressions) or thinned regions may serve one or more of the functions described above. For example, these spaces or thinned regions may alter the rate of degradation in devices that are configured to biodegrade, bioerode, or otherwise break down. Additionally, in variations where the device is configured to deliver one or more drugs to surrounding tissue, these spaces may act to hold one or more materials that act as a drug-delivery depot, as described in more detail below.

Drug Delivery

Any of the devices described here may be used to deliver one or more drugs. Each device described here may be configured to release any suitable number of drugs over any suitable period or periods of time. The selection of drugs, the timing of delivery, and the overall amount of drug or drugs released may be determined by the intended treatment plan, and may be further fine-tuned to the meet the specific needs of an individual patient. Each drug delivered should be released at a rate that provides a patient with a healthy, safe, and effective dosage and should be administered at an overall dosage that is also healthy, safe, and effective.

The devices described here may deliver one or more drugs in any number of ways. In some variations, at least a portion of the device itself incorporates one or more drugs. In some instances, the drug may diffuse out of or may otherwise be released from the device over time. In other instances, the device may comprise one or more cavities, channels, pockets or other space from which a drug or drug-containing material may be released. In still other variations, the device may comprise one or more drug-eluting layers, boluses or reservoirs disposed on one or more surfaces of the device.

Any suitable portions or portions of the device may be configured to release one or more drugs. In some variations, one or more drugs may be incorporated into one or more portions of the hub. In other variations, one or more drugs may be incorporated into one or more portions of one or more legs and/or hub extensions. In some instances, the one or more drugs may diffuse out of the device body. In variations where one or more portions of the device is biodegradable, bioerodible, or otherwise configured to break down, the one or more drugs may be released as these portions degrade or erode.

In other variations, the body of the device may comprise one or more cavities, channels, pores, pockets or other spaces that may hold one or more drugs or drug-containing materials. The spaces may hold one or more drugs, one or more drug-containing solutions, foams, powders, solids, gels, or a combination thereof. The spaces may be pre-loaded, or may be loaded by a physician prior to delivery of the device. In some variations, one or more drugs may diffuse out of the spaces through the device body. In other variations, the drugs or drug-containing materials may exit the device via one or more pores or passageways in the body of the device. In variations where one or more portions of the device is biodegradable, bioerodible, or otherwise configured to break down, one or more of the spaces may become exposed to tissue as these portions degrade or erode. In these instances, one or more drugs or drug-containing materials may be released from the device when the space becomes exposed to tissue.

In still other variations, one or more surfaces of a device may comprise one or more drug-releasing layers or boluses disposed thereon. The drug-releasing layers or boluses may be made of any suitable biocompatible material that is capable of releasing a drug over a period of time, and may be configured in any suitable way. Each device may comprise any number of drug-releasing layers or boluses (e.g., zero, one, two, three, four or more). Each drug-releasing layer may coat or cover the entire surface of the device, or may only cover one or more selected portions of the device. Additionally, one drug-releasing layer may be at least partially disposed over one or more additional drug-releasing layers.

Overall, the device may be configured to release one or more drugs over a predetermined period of time. This period of time may be on the order of hours, on the order of days, on the order of weeks, or on the order of months. This period of drug delivery will be determined with consideration of the nature and amount of the drug or drugs to be released as well as the intended treatment regimen. For example, when the device is used to treat nasal polyposis, the period may be between about 1 week and about 5 weeks, between about 1 week and about 4 weeks, between about 1 week and about 3 weeks, between about 1 week and about 2 weeks, between about 2 weeks and about 5 weeks, between about 2 weeks and about 4 weeks, between about 2 weeks and about 3 weeks, between about 3 weeks and about 5 weeks, between about 3 weeks and about 4 weeks, between about 2 weeks and about 3 weeks, between about 1 month and about 4 months, between about 1 month and about 3 months, between about 1 months and about 2 months, between about 2 months about 4 months, between about 2 months and about 3 months, between about 3 months and about 4 months, about 5 months, about 6 months, or greater than 6 months. In variations where the device is biodegradable, this period may match the degradation period, such as the illustrative degradation periods described above. As will be described in more detail below, this period may not begin immediately upon implantation or administration of the device. Additionally, in some variations, the device may be replaced after a given period of time. For example, in some variations one device is configured to release one or more drugs for a first period of time (e.g., about 4 months), and then is replaced by a second device configured to release one or more drugs for a second period of time (e.g., about 2 months).

Drugs may be released at a constant rate from the device, but need not be. Indeed, the devices may be configured with any suitable release rate profile. In some variations, the daily amount of drug released may decrease over time. For example, a device may release a certain amount of drug for a first period of time (e.g., one week), then may release a second amount of drug for a second period of time. Similarly, the amount of drug delivered may change any number of times during a span of time. The amount of drug released may decrease over time, or may increase over time, or may increase over one span of time and decrease over a different span of time. Furthermore, in some variations a device may comprise multiple drug eluting layers, and each layer may be configured to have a different and specific release profile. Of course, it should be understood that each layer may comprise, contain, include, or be configured to release one or more drug or agent therefrom. Each layer may comprise, contain, include, or be configured to release the same or a different drug or agent therefrom. Similarly, the device body may additionally comprise a drug, and the device body may provide a different release profile from those of one or more drug eluting layers.

In still further variations, the device may comprise one or more barrier layers. These layers may or may not release one or more drugs, and may delay the release of one or more drugs from one or more drug releasing layers or from the device itself. The barrier layer may or may not be a bulk eroding polymer, or may or may not be a surface-eroding polymer. In some variations, the barrier layer may prevent the passage of drug therethrough. In these variations, the barrier layer may provide a time during which no drug is released from at least a portion of a drug releasing layer or from at least a portion of the device. Once the barrier layer has sufficiently degraded or otherwise eroded, drug release may begin or resume. In other variations, the barrier layer may allow some amount drug to pass therethrough. In some of these variations, the amount of drug that passes through barrier layer may be less than that which would be released from the drug releasing layer in the absence of the barrier layer. The barrier layer thus may provide a period during which a smaller amount of drug is released from at least a portion of the drug releasing layer. Once the barrier layer has sufficiently degraded or otherwise eroded, the amount of drug released from the device may increase.

These aforementioned drug-delivery variations, and combinations thereof, may allow the device to provide a variable drug release profile, or provide bursts, either initial or delayed, in addition to the device's baseline release profile. Additionally, these variations may allow the device to provide different drug release profiles that are separated in time. For example, the device may comprise two drug releasing layers separated by a barrier layer. The outer drug releasing layer may release an initial amount of drug over an initial period of time, and may follow any suitable drug release profile. The barrier layer may then degrade or erode over a certain period of time, during which some or no drug is released from a second drug releasing layer. Once this degradation has substantially finished, the second drug releasing layer may then release a second amount of drug over a second period of time, and this release may also follow any suitable drug release profile. Each drug releasing layer may release any suitable amount of any suitable drug over any suitable amount of time, as described above.

Additionally, one or more release rate modifiers may also be used. The release rate modifier may be any suitable biocompatible material that serves to alter the rate at which a drug is released from the device. In some variations, the release rate modifier may include a hydrophilic agent. In some variations, the release rate modifier is a polyethylene glycol, e.g., a polyethylene glycol with a molecular weight of between about 3000 to about 13000, between about 3000 to about 11000, between about 3000 to about 9000, between about 3000 to about 7000, between about 3000 to about 5000, between about 5000 to about 13000, between about 5000 to about 11000, between about 5000 to about 9000, between about 5000 to about 7000, between about 7000 to about 13000, between about 7000 to about 11000, between about 7000 to about 9000, between about 9000 to about 13000, between about 9000 to about 11000, between about 11000 to about 13000, and the like. In some variations, the release rate modifier is a polyethylene glycol with a molecular weight of about 6000.

As mentioned herein throughout, the device may be configured to deliver multiple drugs. In some variations, multiple types of drug particles are contained within a single drug eluting layer or within the device body. In other variations, a device comprises a drug eluting layer that is discontinuous, having different segments containing different drugs. In these variations, the different segments may have different compositions, and thus may also provide differing release rates. In still other variations, multiple drug eluting layers may be used, where each layer contains a different drug or combination of drugs. Drug-releasing boluses, as described above, may also hold different drugs therein or may collectively release different drugs than those released by the drug eluting layer. In still other variations, the device itself may release a different drug or combination of drugs than those drugs released by a drug eluting layer or layers. Any combination of these variations may also be used to achieve the desired drug delivery profiles.

Illustrative Agents

The device may comprise any suitable drug or agent, and the agent selected will largely be determined by the desired use of the device. The device may comprise one or more diagnostic agents and may also comprise one or more therapeutic agents. Diagnostic agents may be used, for example, in diagnosing the presence, nature, and/or extent of a disease or medical condition in a subject. Conversely, a therapeutic agent may be used to treat or affect one or more diseases, conditions, sensations, or symptoms.

Diagnostic agents include, for example, contrast agents for use in connection with ultrasound imaging, magnetic resonance imaging (MRI), nuclear magnetic resonance (NMR), computed tomography (CT), electron spin resonance (ESR), nuclear medical imaging, optical imaging, elastography, fluorescence imaging, positron emission tomography (PET), radiofrequency (RF) and microwave laser. Diagnostic agents may also include any other agent useful in facilitating diagnosis of is disease or other condition in a patient, whether or not imaging methodology is employed.

Examples of specific diagnostic agents include radioopaque materials such as iodine or iodine-derivatives, for example, iohexal and iopamidol. Other diagnostic agents such as, for example, radioisotopes, are detectable by tracing radioactive emission. Examples of agents detectable by MRI are generally paramagnetic agents including, but not limited to, gadolinium chelated compounds. An example of an agent detectable by ultrasound includes, but is not limited to, perflexane. An example of a fluorescence agent includes, but is not limited to, indocyanine green. Examples of agents used in diagnostic PET include, but are not limited to, fluorodeoxyglucose, sodium fluoride, methionine, choline, deoxyglucose, butanol, raclopride, spiperone, bromospiperone, carfentanil, and flumazenil.

The device may also comprise any suitable therapeutic agent. Suitable classes of therapeutic agents include, for example, anti-inflammatory agents, anti-allergens, anti-cholinergic agents, antihistamines, anti-infectives, anti-platelet agents, anti-coagulants, anti-thrombic agents, anti-scarring agents, anti-proliferative agents, chemotherapeutic agents, anti-neoplastic agents, decongestants, healing promoting agents and vitamins (for example, retinoic acid, vitamin A, depaxanthenol, vitamin B and their derivatives), hypersomolar agents, immunomodulators, immunosuppressive agents, and combinations and mixtures thereof. In some variations, one or more these therapeutic agents may be a phytopharmaceutical. Generally, a phytopharmaceutical is a pharmaceutical of plant origin. In some instances, the phytopharmaceutical may be an anti-inflammatory. Examples of suitable anti-inflammatory phytopharmaceuticals include, but are not limited to, commiphora mukul, cimicifuga, ginger, corydalis, evodia, turmeric, psoralea gladulosa, rumex patientia, baccharis, arnica, soy isoflavone, boswellia, tithonia, qiang huo, prickly pear, and S-Adenosylmethionine. In other instances, a phytopharmaceutical may be an analgesic, such as, for example, capsaicin, clove, eucomis, stephaia, and celastrus. In still other instances, the phytopharmaceutical may be a vasodilator (e.g., cinnamon), an anti-bacterial agent (e.g., copis, ogon), a migraine-treating agent (e.g., feverfew), an anti-oxidant (e.g., vitis, solidago canadensis), or a combination thereof.

Anti-infective agents generally include antibacterial agents, antifungal agents, antiparasitic agents, and antiviral agents, and antiseptics. Anti-inflammatory agents generally include steroidal and nonsteroidal anti-inflammatory agents.

Examples of antiallergic agents that may suitable for use with the described methods and devices include, but are not limited to, pemirolast potassium (ALAMAST®, Santen, Inc.), and any prodrugs, metabolites, analogs, homologues, congeners, derivatives, salts and combinations thereof. Examples of antiproliferative agents include, but are not limited to, actinomycin D, actinomycin IV, actinomycin $I_1$, actinomycin $X_1$, actinomycin $C_1$, and dactinomycin (COSMEGEN®, Merck & Co., Inc.). Examples of antiplatelet, anticoagulant, antifibrin, and antithrombin agents include, but are not limited to, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibodies, recombinant hirudin, and thrombin inhibitors (ANGIOMAX®, Biogen, Inc.), and any prodrugs, metabolites, analogs, homologues, congeners, derivatives, salts and combinations thereof. Examples of pro-healing agents include, but are not limited to, sirolimus, everolimus, temsiolimus, and vitamin A.

Examples of cytostatic or antiproliferative agents that may be suitable for uses with the described methods and devices include, but are not limited to, angiopeptin, angiotensin converting enzyme inhibitors such as captopril (CAPOTEN® and CAPOZIDE®, Bristol-Myers Squibb Co.), cilazapril or lisinopril (PRINIVIL® and PRINZIDE®, Merck & Co., Inc.); calcium channel blockers such as nifedipine; colchicines; fibroblast growth factor (FGF) antagonists, fish oil (omega 3-fatty acid); histamine antagonists; lovastatin (MEVACOR®, Merck & Co., Inc.); monoclonal antibodies including, but not limited to, antibodies specific for Platelet-Derived Growth Factor (PDGF) receptors; nitroprusside; phosphodiesterase inhibitors; prostaglandin inhibitors; suramin; serotonin blockers; steroids; thioprotease inhibitors; PDGF antagonists including, but not limited to, triazolopyrimidine; and nitric oxide, and any prodrugs, metabolites, analogs, homologues, congeners, derivatives, salts and combinations thereof.

Examples of antibacterial agents that may be suitable for use with the described methods and devices include, but are not limited to, aminoglycosides, amphenicols, ansamycins, β-lactams such as penicillins, lincosamides, macrolides, nitrofurans, quinolones, sulfonamides, sulfones, tetracyclines, vancomycin, and any of their derivatives, or combinations thereof. Examples of penicillins that may be suitable for use with the described methods and devices include, but are not limited to, amdinocillin, amdinocillin pivoxil, amoxicillin, ampicillin, apalcillin, aspoxicillin, axidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin G benethamine, penicillin G benzathine, penicillin G benzhydrylamine, penicillin G calcium, penicillin G hydrabamine, G potassium, penicillin G procaine, penicillin N, penicillin O, penicillin V, penicillin V benzathine, penicillin V hydrabamine, penimepicycline, phenethicillin potassium, piperacillin, pivampicillin, propicillin, quinacillin, sulbenicillin, sultamicillin, talampicillin, temocillin, and ticarcillin.

Examples of antifungal agents suitable for use with the described methods and devices include, but are not limited to, allylamines, imidazoles, polyenes, thiocarbamates, triazoles, and any of their derivatives. Antiparasitic agents that may be employed include, but are not limited to, atovaquone, clindamycin, dapsone, iodoquinol, metronidazole, pentamidine, primaquine, pyrimethamine, sulfadiazine, trimethoprim/sulfamethoxazole, trimetrexate, and combinations thereof.

Examples of antiviral agents suitable for use with the described methods and devices include, but are not limited to, acyclovir, famciclovir, valacyclovir, edoxudine, ganciclovir, foscarnet, cidovir (vistide), vitrasert, formivirsen, HPMPA (9-(3-hydroxy-2-phosphonomethoxypropyl)adenine), PMEA (9-(2-phosphonomethoxyethyl)adenine), HPMPG (9-(3-Hydroxy-2-(Phosphonomethoxy)propyl) guanine), PMEG (9-[2-(phosphonomethoxy)ethyl]guanine), HPMPC (1-(2-phosphonomethoxy-3-hydroxypropyl)-cytosine), ribavirin, EICAR (5-ethynyl-1-beta-D-ribofuranosylimidazole-4-carboxamine), pyrazofurin (3-[beta-D-ribofuranosyl]-4-hydroxypyrazole-5-carboxamine), 3-Deazaguanine, GR-92938X (1-beta-D-ribofuranosylpyrazole-3,4-dicarboxamide-de), LY253963 (1,3,4-thiadiazol-2-yl-cyanamide), RD3-0028 (1,4-dihydro-2,3-Benzodithiin), CL387626 (4,4'-bis[4,6-d][3-aminophenyl-N-,N-bis(2-carbamoylethyl)-sulfonilimino]-1,3,5-trazin-2-ylamino-biphenyl-2-,2'-disulfonic acid disodium salt), BABIM (Bis[5-Amidino-2-benzimidazolyl-1]-methane), NIH351, and combinations thereof.

Examples of antiseptic agents suitable for use with the described methods and devices include, but are not limited to, alcohol, chlorhexidrine, iodine, triclosan, hexachlorophene, and silver-based agents, for example, silver chloride, silver oxide, and silver nanoparticles.

Anti-inflammatory agents may include steroidal and nonsteroidal anti-inflammatory agents. Examples of suitable steroidal anti-inflammatory agents include, but are not limited to, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramothasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, any of their derivatives and combinations thereof.

Examples of suitable nonsteroidal anti-inflammatory agents include, but are not limited to, COX inhibitors. These COX inhibitors may include COX-1 or COX nonspecific inhibitors such as, for example, salicylic acid derivatives, aspirin, sodium salicylate, choline magnesium trisalicylate, salsalate, diflunisal, sulfasalazine and olsalazine; para-aminophenol derivatives such as acetaminophen; indole and indene acetic acids such as indomethacin and sulindac; heteroaryl acetic acids such as tolmetin, dicofenac and ketorolac; arylpropionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam) and alkanones such as nabumetone. The COX inhibitors may also include selective COX-2 inhibitors such as, for example, diaryl-substituted furanones such as rofecoxib; diaryl-substituted pyrazoles such as celecoxib; indole acetic acids such as etodolac and sulfonanilides such as nimesulide).

Examples of chemotherapeutic/antineoplastic agents that may be used in the devices described here include, but are not limited to antitumor agents (e.g., cancer chemotherapeutic agents, biological response modifiers, vascularization inhibitors, hormone receptor blockers, cryotherapeutic agents or other agents that destroy or inhibit neoplasia or tumorigenesis) such as alkylating agents or other agents which directly kill cancer cells by attacking their DNA (e.g., cyclophosphamide, isophosphamide), nitrosoureas or other agents which kill cancer cells by inhibiting changes necessary for cellular DNA repair (e.g., carmustine (BCNU) and lomustine (CCNU)), antimetabolites or other agents that block cancer cell growth by interfering with certain cell functions, usually DNA synthesis (e.g., 6-mercaptopurine and 5-fluorouracil (5FU), antitumor antibiotics and other compounds that act by binding or intercalating DNA and preventing RNA synthesis (e.g., doxorubicin, daunorubicin, epirubicin, idarubicin, mitomycin-C and bleomycin), plant (vinca) alkaloids and other anti-tumor agents derived from plants (e.g., vincristine and vinblastine), steroid hormones, hormone inhibitors, hormone receptor antagonists and other agents which affect the growth of hormone-responsive cancers (e.g., tamoxifen, herceptin, aromatase inhibitors such as aminoglutethamide and formestane, triazole inhibitors such as letrozole and anastrazole, steroidal inhibitors such as exemestane), antiangiogenic proteins, small molecules, gene therapies and/or other agents that inhibit angiogenesis or vascularization of tumors (e.g., meth-1, meth-2, thalidomide), bevacizumab (Avastin), squalamine, endostatin, angiostatin, Angiozyme, AE-941 (Neovastat), CC-5013 (Revimid), medi-522 (Vitaxin), 2-methoxyestradiol (2ME2, Panzem), carboxyamidotriazole (CAI), combretastatin A4 prodrug (CA4P), SU6668, SU11248, BMS-275295, COL-3, EMD 121974, IMC-1C11, IM862, TNP-470, celecoxib (Celebrex), rofecoxib (Vioxx), interferon alpha, interleukin-12 (IL-12) or any of the compounds identified in Science Vol. 289, Pages 1197-1201 (Aug. 17, 2000), which is expressly incorporated herein by reference, biological response modifiers (e.g., interferon, bacillus calmette-guerin (BCG), monoclonal antibodies, interleukin 2, granulocyte colony stimulating factor (GCSF), etc.), PGDF receptor antagonist, herceptin, asparaginase, busulphan, carboplatin, cisplatin, carmustine, cchlorambucil, cytarabine, dacarbazine, etoposide flucarbazine, flurouracil, gemcitabine, hydroxyurea, ifosphamide, irinotecan, lomustine, melphalan, mercaptopurine, methotrexate, thioguanine, thiotepa, tomudex, topotecan, treosulfan, vinblastine, vincristine, mitoazitrone, oxaliplatin, procarbazine, streptocin, taxol or paclitaxel, taxotere, azathioprine, docetaxel analogs/congeners derivatives of such compounds, and combinations thereof.

Examples of decongestants that may be used in the devices and methods described here include, but are not limited to, epinephrine, pseudoephedrine, oxymetazoline, phenylephrine, tetrahydrozolidine, and xylometazoline. Examples of mucolytics that may be used in the devices and methods described here include, but are not limited to, acetylcysteine, dornase alpha, and guaifenesin. Anti-histamines such as azelastine, diphenhydramine, and loratidine may also be used in the methods and devices described here.

Suitable hyperosmolar agents that may be used in the devices described here include, but are not limited to, furosemide, sodium chloride gel, and other salt preparations that draw water from tissue or substances that directly or indirectly change the osmolarity of the mucous layer.

Other bioactive agents useful in the present invention include, but are not limited to, free radical scavengers; nitric oxide donors; rapamycin; methyl rapamycin; everolimus; tacrolimus; 40-O-(3-hydroxy)propyl-rapamycin; 40-O-[2-(2-hydroxy)ethoxy]ethyl-rapamycin; tetrazole containing rapamycin analogs such as those described in U.S. Pat. No. 6,329,386; estradiol; clobetasol; idoxifen; tazarotene; alpha-interferon; host cells including, but not limited to prokaryotes and eukaryotes such as, for example, epithelial cells and genetically engineered epithelial cells; dexamethasone; and, any prodrugs, metabolites, analogs, homologues, congeners, derivatives, salts and combinations thereof.

Examples of free radical scavengers include, but are not limited to, 2,2',6,6'-tetramethyl-1-piperinyloxy, free radical (TEMPO); 4-amino-2,2',6,6'-tetramethyl-1-piperinyloxy, free radical (4-amino-TEMPO); 4-hydroxy-2,2',6,6'-tetrametyl-piperidene-1-oxy, free radical (TEMPOL), 2,2',3,4,5,5'- hexamethyl-3-imidazolinium-1-yloxy methyl sulfate, free radical; 16-doxyl-stearic acid, free radical; superoxide dismutase mimic (SODm) and any analogs, homologues, congeners, derivatives, salts and combinations thereof. Nitric oxide donors include, but are not limited to, S-nitrosothiols, nitrites, N-oxo-N-nitrosamines, substrates of nitric oxide synthase, diazenium diolates such as spermine diazenium diolate, and any analogs, homologues, congeners, derivatives, salts and combinations thereof.

Materials

The devices described here may be made of any suitable material or combinations of material. In some variations, one or more of the materials may biodegradable, bioerodable, or otherwise erodable. In these variations, the rate of biodegradation of the degradable portions of the device may be affected by a number of factors including, but not limited to, the type of material from which the portion is formed, the size and shape of the device, and the deployment conditions. The devices described here may be made from a single material, or may be made from a combination of materials. In some variations, the material or materials may be shape-memory materials.

One or more portions of the device may comprise one or more polymers. A polymer may be biodegradable, but need not be. Examples of biodegradable polymers that may be suitable for use with the methods and devices describe here include, but are not limited to, aliginate, cellulose and ester, dextran, elastin, fibrin, hyaluronic acid, polyacetals, polyarylates (L-tyrosine-derived or free acid), poly($\alpha$-hydroxy-esters), poly($\beta$-hydroxy-esters), polyamides, poly(amino acid), polyalkanotes, polyalkylene alkylates, polyalkylene oxylates, polyalkylene succinates, polyanhydrides, polyhydride esters, polyaspartimic acid, polybutylene diglycolate, poly(caprolactone), poly(caprolactone)/poly(ethylene glycol) copolymers, poly(carbonate), L-tyrosine-derived polycarbonates, polycyanoacrylates, polydihidropyrans, poly(dioxanone), poly-p-dioxanone, poly(epsilon-caprolactone), poly(epsilon-caprolactone-dimethyltrimethylene carbonate), poly(esteramide), poly(esters), aliphatic polyesters, poly(etherester), poly(ethylene glycol)(poly(orthoester) copolymers, poly(glutarunic acid), poly(glycolic acid), poly(glycolide), poly(glycolide)/poly(ethylene glycol) copolymers, poly(glycolide-trimethylene carbonate), poly(hydroxyalkanoates), poly(hydroxybutyrate), poly(hydroxybutyrate-co-valerate), poly(imino carbonates), polyketals, poly(lactic acid-co-glycolic acid), poly(lactic acid-co-glycolic acid)/poly(ethylene glycol) copolymers, poly(lactide), poly(lactide-co-caprolactone), poly(DL-lactide-co-glycolide), poly(lactide-co-glycolide)/poly(ethylene glycol) copolymers, poly(lactide)/poly(ethylene glycol) copolymers, poly(lactide)/poly(glycolide) copolymers, polyorthoesters, poly(oxyethylene)/poly(oxypropylene) copolymers, polypeptides, polyphosphazenes, polyphosphoesters, polyphosphoester urethanes, poly(propylene fumarate-co-ethylene glycol), poly(trimethylene carbonate), polytyrosine carbonate, polyurethane, PorLastin or silk-ealastin polymers, spider silk, tephaflex, terpolymer (copolymers of glycolide, lactide or dimethyltrimethylene carbonate), and combinations, mixtures or copolymers thereof. Examples of nonbiodegradable polymers suitable for use with the methods and devices described herein include, but are not limited to poly(ethylene vinyl acetate), poly(vinyl acetate), silicone polymers, polyurethanes, polysaccarides such as a cellulosic polymer, and cellulose derivatives, acyl substituted cellulose acetates and derivatives thereof, copolymers of poly(ethylene glycol) and poly(butylene terephthalate), polystyrenes, polyvinyl chloride, polyvinyl fluoride, poly(vinyl imidazole), chlorosulphonated polyolefins, polyethylene oxide, and copolymers and blends thereof. In variations where the device comprises poly(lactic-co-glycolic acid), the molar percent of lactide or the molar percent of glycolide may be any suitable amount, for example, between about 0% and about 100%, between about 30% and about 100%, between about 50% and about 100%, between about 70% and about 100%, between about 0% and about 70%, between about 30% and about 70%, between about 50% and about 70%, between about 0% and about 50%, between about 30% and about 50%, between about 0% and about 50% and the like. In some variations, the molar ratio of lactide to glycolide is about 10:90, about 85:15, about 15:85, or the like. In variations where the device comprises a poly(lactic-co-glycolic acid)/poly(ethylene glycol) copolymer, the copolymer may include any suitable amounts of poly(lactic-co-glycolic acid) and poly(ethylene glycol). For example, in some variations the copolymer may comprise, about 90% poly(lactic-co-glycolic acid) and about 10% poly(ethylene glycol). It should be further appreciated that the poly(lactic-co-glycolic acid) may have any suitable molar percentages of lactide and glycolide, as described above.

In other variations, one or more portions of the device comprise one or more metals, metallic materials, or metal alloys. Examples of suitable metals include, but are not limited to zinc, magnesium, cobalt, chromium, nickel, platinum, stainless steel, titanium, tantalum, and iron, combinations thereof and the like. Examples of suitable metal alloys include, but are not limited to, magnesium, nickel-cobalt alloys, nickel-titanium alloys, copper-aluminum-nickel alloys, copper-zinc-aluminum-nickel alloys, combinations thereof and the like. In still other variations, one or more portions of the device may comprise an elastomeric material.

In some variations, one or more portions of the device comprise a mucoadhesive material. For example, some devices comprise one or more mucoadhesive hydrogels, e.g., PLG polymers, polyacrylic acids, carageenan, alginate, xantham gum, carboxymethylcellulose, hydroxypropyl cellulose, chitins, hyaluronic acids, lectins, their derivatives, combinations thereof, and the like.

In some variations, the device may be formed as a single component from a single material or combination of materials. For example, in some variations the device may be formed as a single body. In other variations, different components of the device (e.g., the hub and/or one or more legs) may be formed separately and joined (e.g., via one or more adhesives, mechanical connections, fusing, chemical bonding, or the like) to form the device. In some variations, the entire device or one or more components thereof may be formed by fiber spinning, injection-molding, extrusion, blow-molding, vacuum-formation, casting, and the like. In variations where the device comprises a polymer, the polymer may synthesized by one or more microorganisms. In some variations, one or more portions of the device (e.g., one or more legs, the hub, combinations thereof) may be strained to alter the strength of those portions. When the device comprises one or more polymers, this straining may allow for orientation of polymer chains and formation of polymer crystals, which may increase the rigidity and strength of the device. In some variations, the device or specific device components may be heated during straining, and the straining may or may not occur under a constant rate of strain (e.g., the strain rate may remain constant, may decrease over time, or may increase over time). Additionally, one or more curved or straight segments may be removed from or formed in legs during straining. In some variations, once the device (or specific components thereof) has been strained, the strained portions may be annealed. Annealing may help solidify or otherwise set the oriented polymer chains and crystals in place. Additionally, in some variations the strained devices may be quenched following straining. In variations where the device or components thereof are also annealed, the device or components may be quenched following annealing, which in turn may help prevent relaxation of polymer chains.

Illustrative Variations

As mentioned above, the devices described here may comprise any combination of the aforementioned hubs, legs, and additional features. Also included here are several illustrative variations of expandable devices suitable for use in the body. These variations are provided for the purposes of clarity and understanding, and it should be understood that certain changes and modifications may be practiced. For example, it should be appreciated that any of the illustrative variations described below may be made from any suitable material (e.g., from one or more polymers), may be formed in any suitable manner, may be configured to deliver one or more drugs, may be configured to biodegrade, bioerode, or otherwise break, and combinations thereof, as described in more detail hereinthroughout.

Variation 1

Figure 13A:
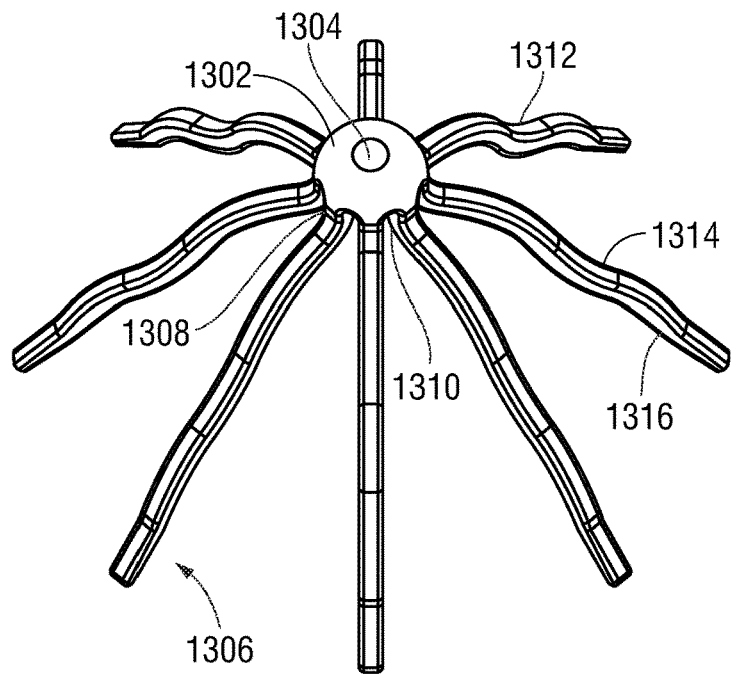
FIGS. 13A, 13B, 14-17, 18A, 18B, 19 and 20 depict several illustrative variations of the devices described here.
Figure 13B:
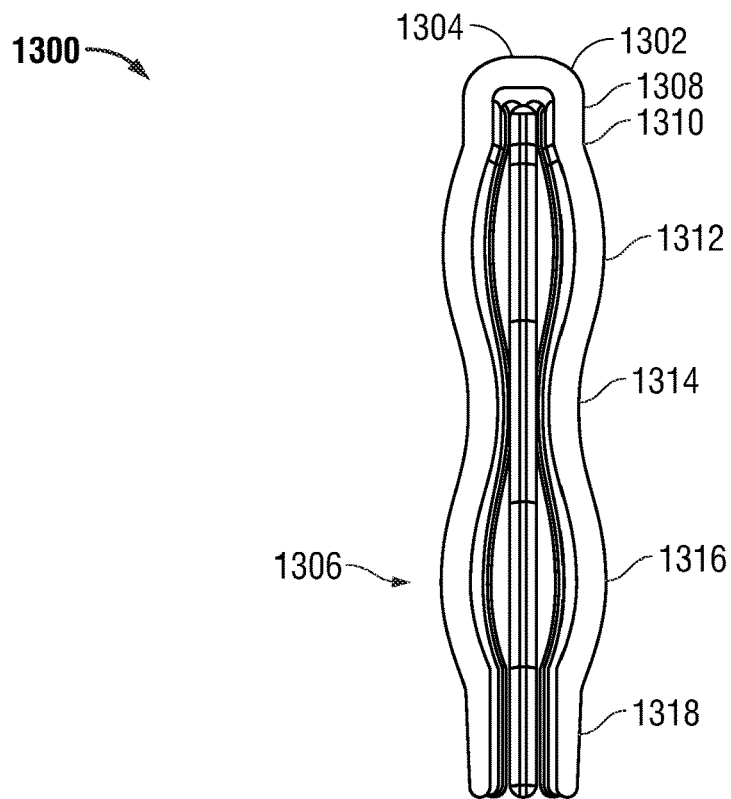

FIGS. 13A and 13B illustrate a perspective view and a cross-sectional side view, respectively, of one variation of device (1300). Shown there is a dome-shaped hub (1302) having a flat top (1304) and eight legs (1306) attached to hub (1302). In this variation, legs (1306) may comprise a first straight segment (1308) attached to hub (1302), a first outwardly-curved segment (1310) attached to first straight segment (1308), a first inwardly-curved segment (1312) attached to first outwardly-curved segment (1310), a second outwardly-curved segment (1314) attached to first inwardly-curved segment (1312), a second inwardly-curved segment (1316) attached to second outwardly-curved segment (1314), and a second straight segment (1318) attached to the second inwardly-curved segment (1316).

In this particular variation, each leg (1306) may be configured such that the second straight segment (1318) is substantially parallel to the longitudinal axis of the device (1300) when the device (1300) is in a low-profile configuration, as shown in FIG. 13B. This may help aid attachment of device (1300) to a delivery device (not shown) having a sheath, as will be described in more detail below. Additionally, the second straight segment (1318) may be angled outward when the device (1300) is in its expanded configuration. Thus, when device (1300) is placed in the body, legs (1306) may press the ends of one or more of these second straight segments (1318) into surrounding tissue, which may help keep the device in place at a target location. Additionally, the second straight segments (1318) are shown in FIGS. 13A and 13B as having a tapered thickness. By reducing the thickness of the distal ends of the second straight segments (1318), the distal ends of straight segments (1318) may apply greater pressure on surrounding tissues because force applied by the leg is distributed over a smaller point.

Additionally, the first (1312) and second (1314) inwardly-curved segments may help to hold device (1300) in place when delivered to one or more tissues. More specifically, when device (1300) is placed in tissue, the device may have a tendency to "spring" forward when surrounding tissue resists the expansion of legs (1306). The inwardly-curved segments may provide additional surfaces that may engage one more surrounding tissues to help prevent this forward movement.

Variation 2

Figure 14:
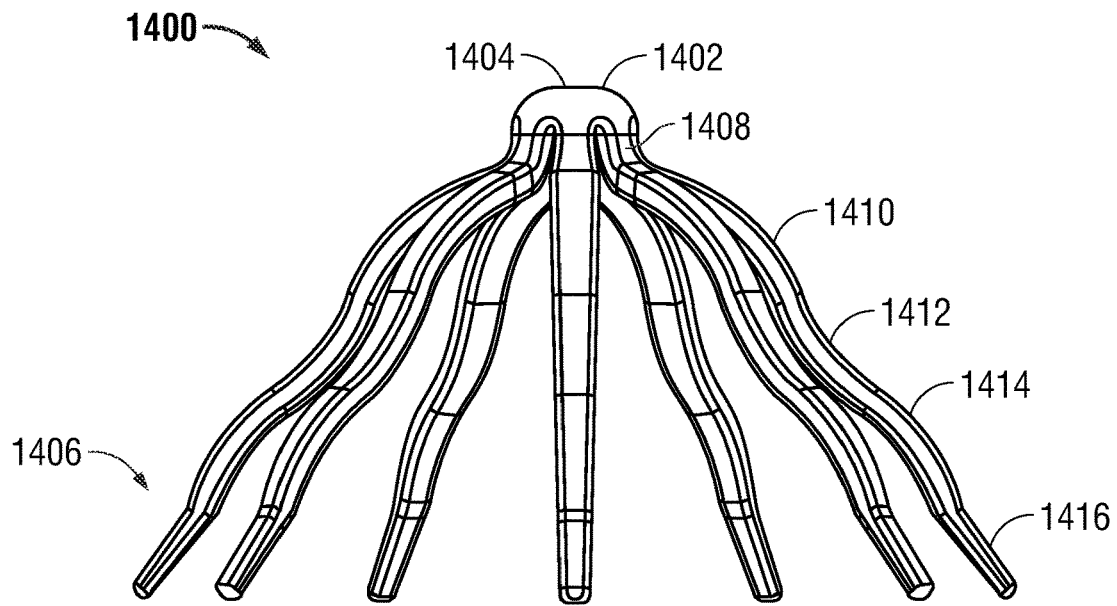

FIG. 14 shows a side view of another variation of expandable device (1400). Shown there is a dome-shaped hub (1402) having a flat top (1404) and seven legs (1406) attached thereto. Each leg may comprise a first outwardly-curved segment (1408) attached to hub (1402), a first inwardly-curved segment (1410) attached to first outwardly-curved segment (1408), a second outwardly-curved segment (1412) attached to first inwardly-curved segment (1410), a second inwardly-curved segment (1414) attached to second outwardly-curved segment (1412), and a straight segment (1416) attached to the second inwardly-curved segment (1414). As shown in FIG. 14, the width first outwardly-curved segment (1408) may be tapered between its point of attachment to hub (1402) and its point of attachment to first inwardly-curved segment (1410). The narrower width at the connection with hub (1402) may increase the flexibility of leg (1406), while the wider portion of first outwardly-curved segment (1408) may help provide strength to that segment. Additionally, the width of leg (1406) may be tapered from the first inwardly-curved segment (1410) to the end of the leg (1406).

Variation 3

Figure 15:
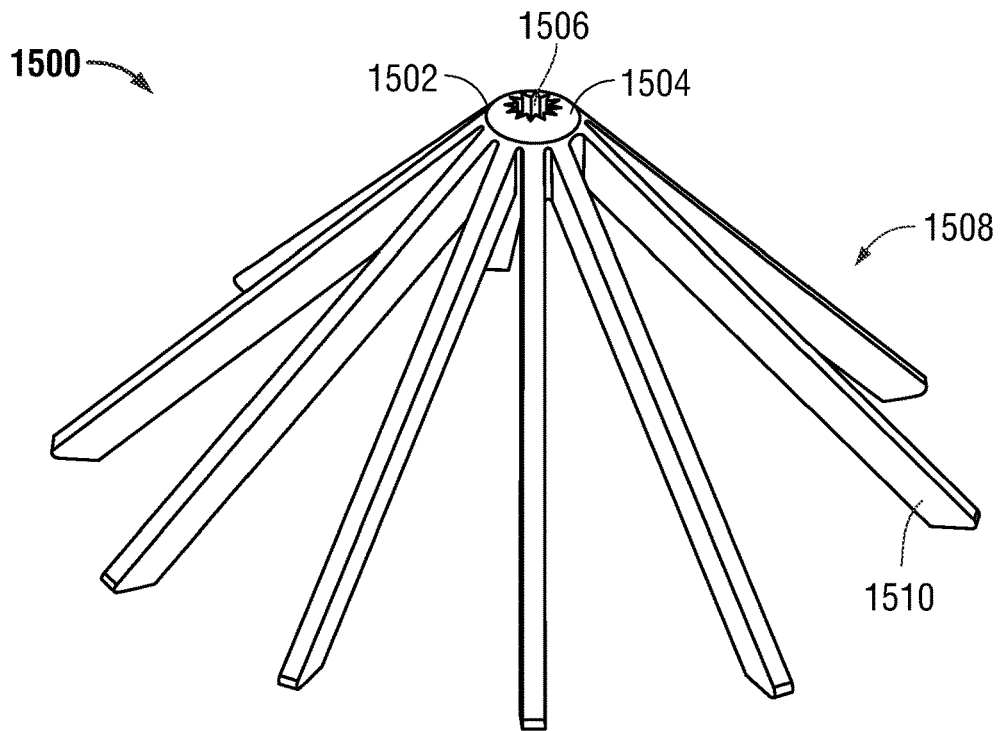

FIG. 15A illustrates another variation of device (1500). Shown there is cylindrical hub (1502) having a domed top (1504) and a star-shaped channel (1506) therethrough. Also shown there are a plurality of legs (1508) attached to the side of hub (1502), each leg (1508) comprising a straight segment (1510).

Variation 4

Figure 16:
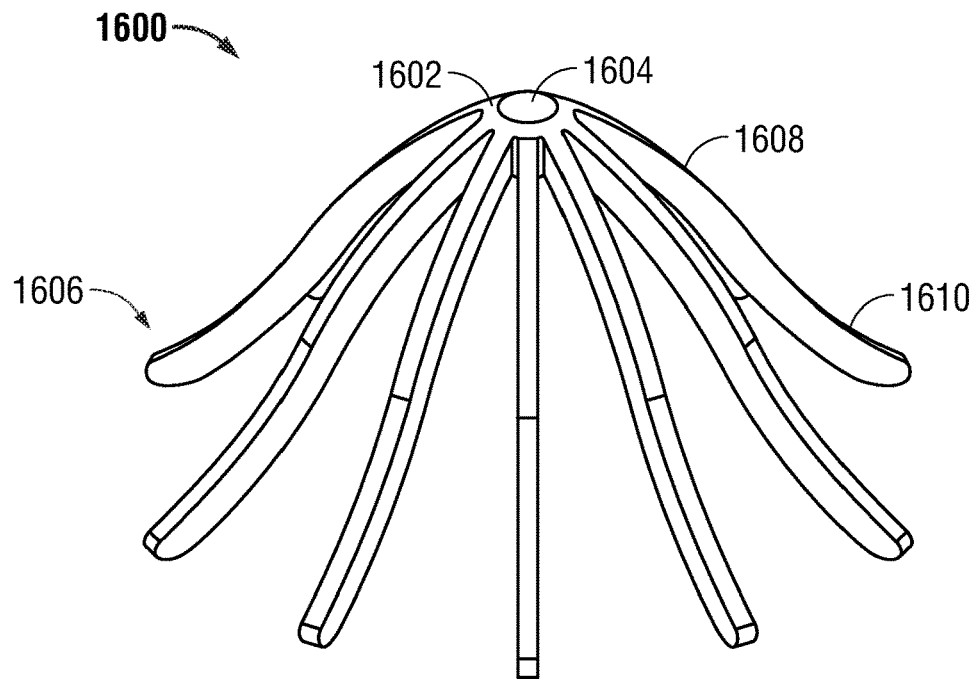

FIG. 16 depicts a perspective view of a variation of device (1600). Shown there is cylindrical hub (1602) having a circular channel (1604) therethrough. Also shown there are legs (1606), each leg (1606) comprising an inwardly curved segment (1608) attached to a side of hub (1602) and an outwardly-curved segment (1610) attached to the inwardly-curved segment (1608).

Variation 5

Figure 17:
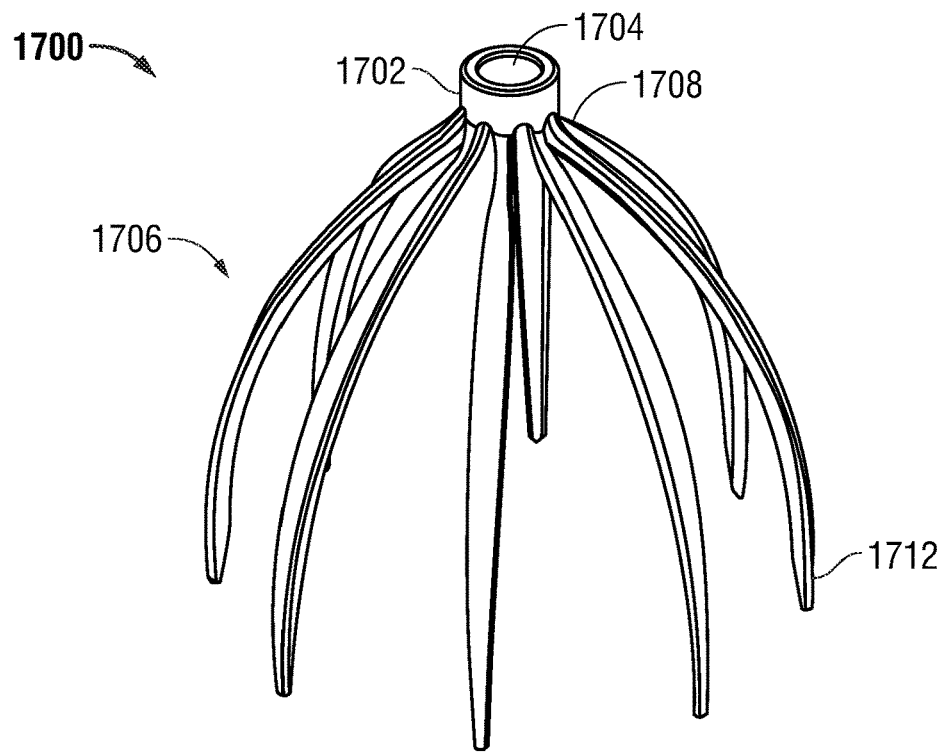

FIG. 17 shows a perspective view of another variation of device (1700). Shown there is a cylindrical hub (1702) having a circular passageway (1704) therethrough. Also shown there are legs (1706) attached to the bottom of hub (1702). Each leg (1706) may comprise an outwardly curved segment (1708) attached to the hub (1702), an inwardly-curved segment (1710) attached to the outwardly curved segment (1708), and a straight segment (1712) attached to the inwardly-curved segment (1710). As shown in FIG. 17, the width of the inwardly-curved segments (1710) may be largest at the center of the inwardly-curved segment (1710), and may taper down in either direction. This may provide flexibility at either end of an inwardly-curved segment (1710) while providing strength in the middle of the inwardly-curved segment (1710).

Variation 6

Figure 18A:
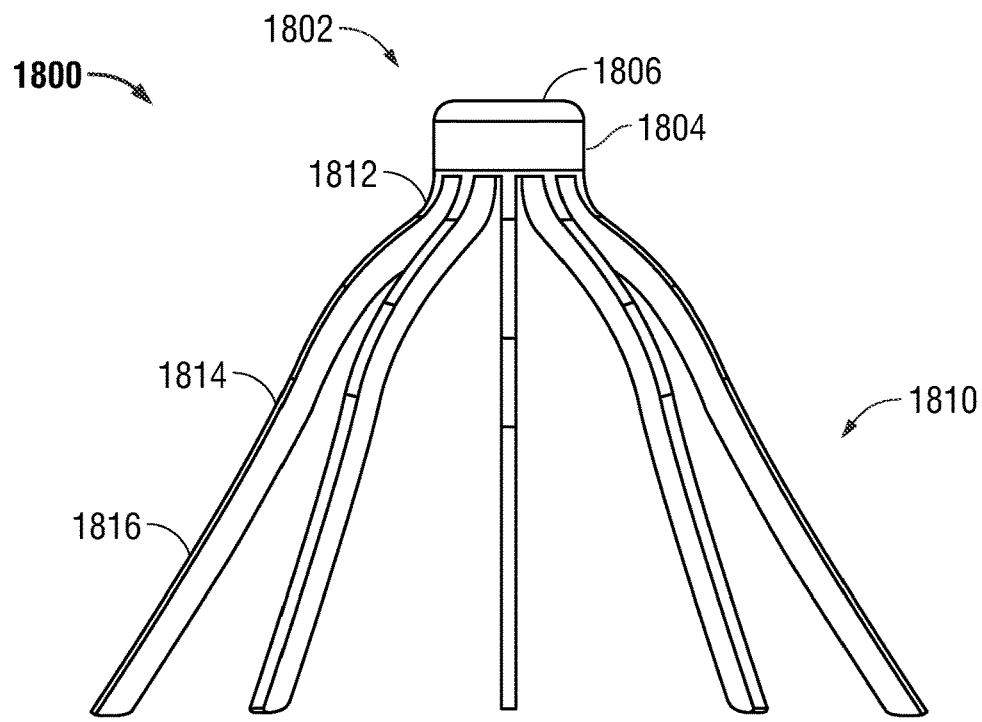
Figure 18B:
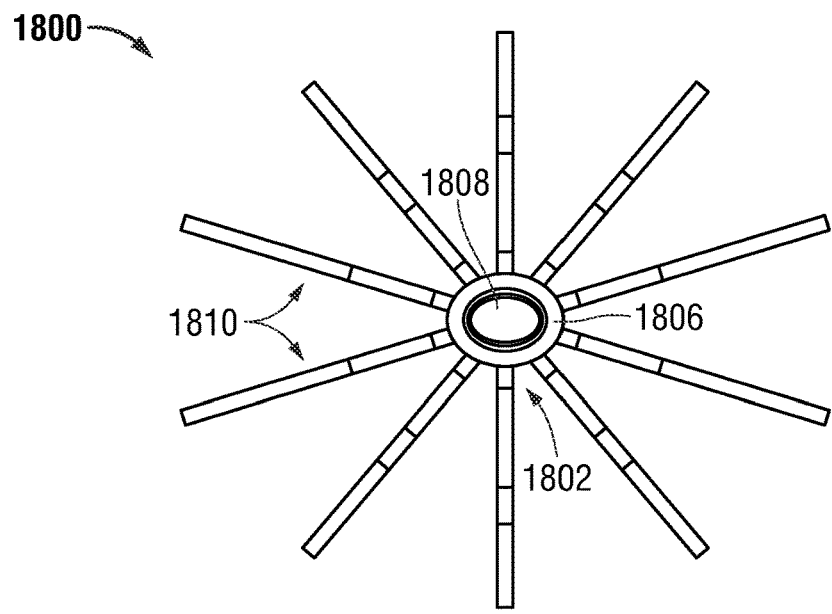

FIGS. 18A and 18B show a side view and a top view, respectively, of another variation of device (1800). Shown there is a hub (1802) with an oval transverse cross-section. In this variation, hub (1802) may comprise an extension portion (1804) with a domed tip (1806) attached thereto. Hub (1802) may also comprise an oval-shaped channel (1808) through a surface of hub (1802). Attached to hub (1802) are legs (1810), and each leg (1810) may comprise an outwardly-curved segment (1812) attached to hub (1802), an inwardly-curved segment (1814) attached to the outwardly-curved segment (1812), and a straight segment (1816) attached to the inwardly-curved segment (1814). As can be seen from FIG. 18B, legs (1810) may define an oval transverse profile when device (1800) is in an expanded configuration.

Variation 7

Figure 19:
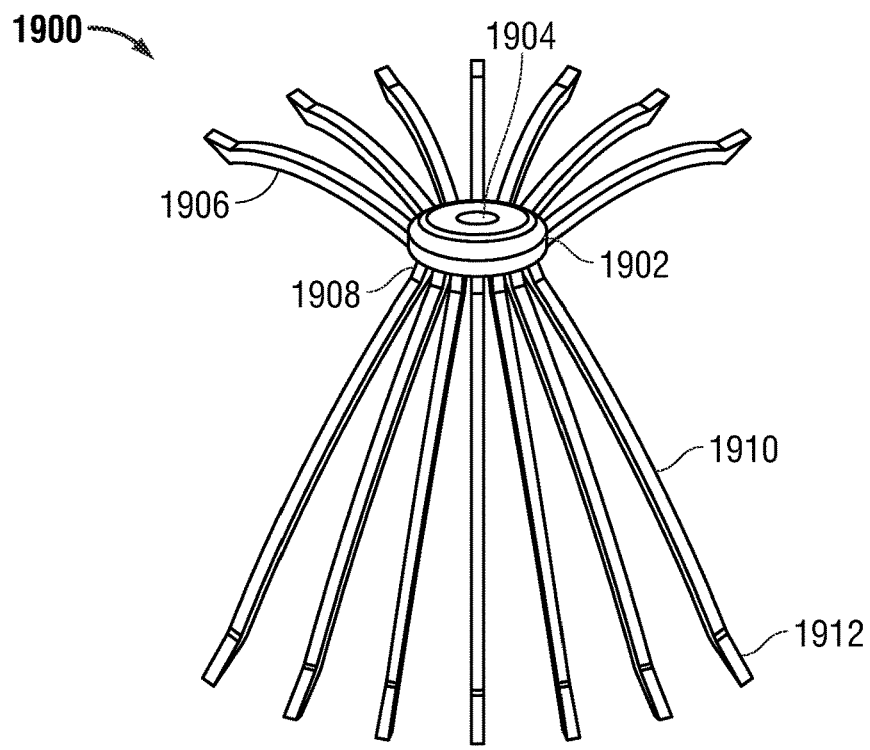

FIG. 19 shows another variation of device (1900). Shown there is a hub (1902) having an oval transverse cross-sectional shape and a circular channel (1904) therethrough. Also shown there are legs (1906), each of which may comprise an outwardly-curved segment (1908) attached to hub (1902), an inwardly-curved segment (1910) attached to the outwardly-curved segment (1908), and a straight segment (1912) attached to the inwardly-curved segment (1914). As shown in FIG. 19, legs (1906) may be unevenly spaced around the circumference of hub (1902). In this variation, legs (1906) may concentrated on either side of the hub (1902), which may provide particular utility in instances where it is desirable to separate two opposing tissue surfaces.

Variation 8

Figure 20:
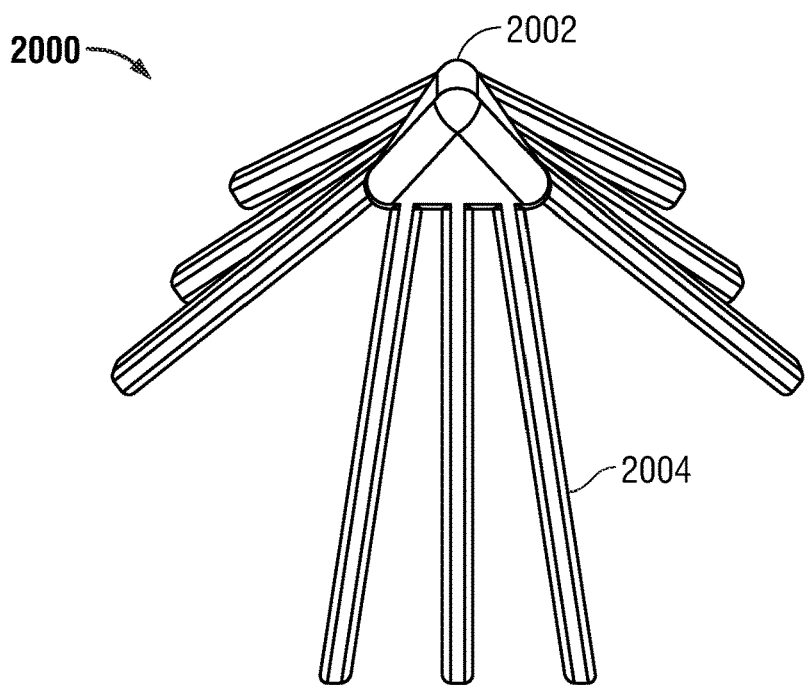

FIG. 20 depicts yet another variation of device (2000). Shown there is a pyramid-shaped hub (2002) and a plurality of straight legs (2004) attached thereto. In this variation, pyramid-shaped hub (2002) may have a triangular base, and legs (1904) may be positioned on each side of the triangular base. This variation may provide particular utility in instances where it is desirable to apply forces to tissue in three different directions.

Variation 9

Figure 25:
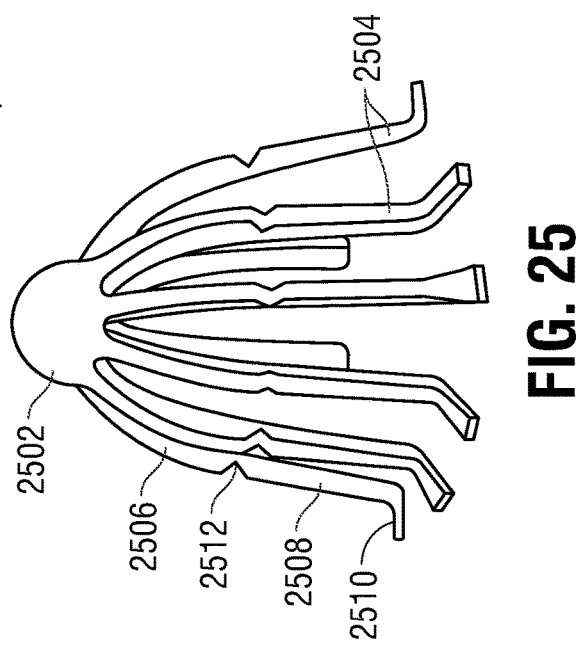
FIG. 25 depicts an illustrative variation of the devices described here.

FIG. 25 depicts yet another variation of device (2500). Shown there is a dome-shaped hub (2502) having a plurality of legs (2504). In this variation, legs may comprise an inwardly-curved segment (2506), a first straight segment (2508) attached to inwardly-curved segment (2506), and a second straight segment (2510) that is angled relative to first straight segment (2508). As shown in FIG. 25, the cross-section area of leg (2504) may be thinned at the junction (2512) between inwardly-curved segment (2506) and first straight segment (2508), but need not. In variations where device (2500) is configured to be biodegradable, bioerodable, or otherwise configured to break down, the thinned junction (2512) may facilitate degradation of legs (2504) at junction (2512). In this way, device (2500) may be configured to help reduce the likelihood that an entire leg (2504) will separate from hub (2502) during degradation. Additionally, second straight segment (2508) may engage tissue when device (2500) is placed in the body in an expanded configuration, which may help hold the device in place within the body.

Delivery Devices

Also described here are delivery devices which may be used to deliver one or more of the expandable devices described above. The devices described above may be delivered by any suitable delivery device to any suitable portion or portions of the anatomy. In some variations, the device may be delivered by a delivery device comprising a cannula, such as one or more of the delivery devices described in U.S. patent application Ser. No. 12/344,395, filed on Dec. 12, 2008 and titled "DELIVERY DEVICES AND METHODS," which is hereby incorporated by reference in its entirety. In these instances, a device may be placed at least partially in a lumen, aperture, or other opening in the cannula while the device is in a low-profile configuration. The cannula may then be advanced to a target location, and the device may be ejected from the cannula in any suitable manner (e.g., via a pusher or one or more gases or fluids). In variations where the device is self-expandable, the device may self-expand upon release from the cannula. In variations where the device is not self-expandable, one or more additional elements (e.g., a balloon or other expandable structure) may help to expand the device. One or more of these additional elements may also be used to help expand a self-expandable device.

Figure 21A:
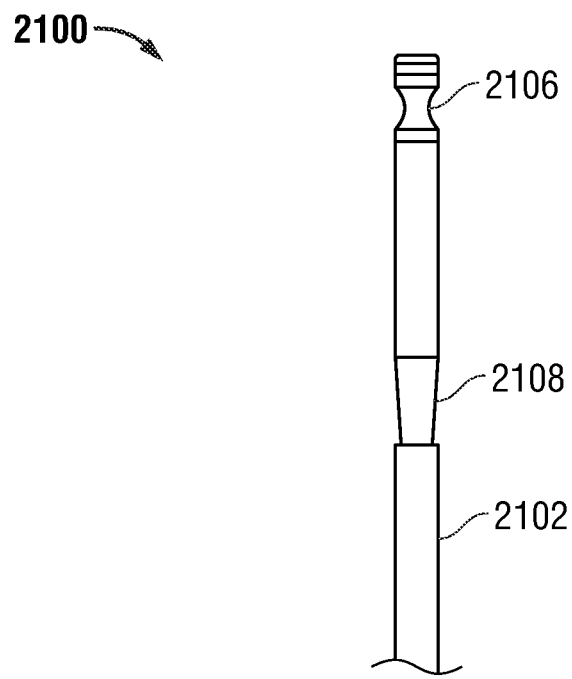
Figure 21B:
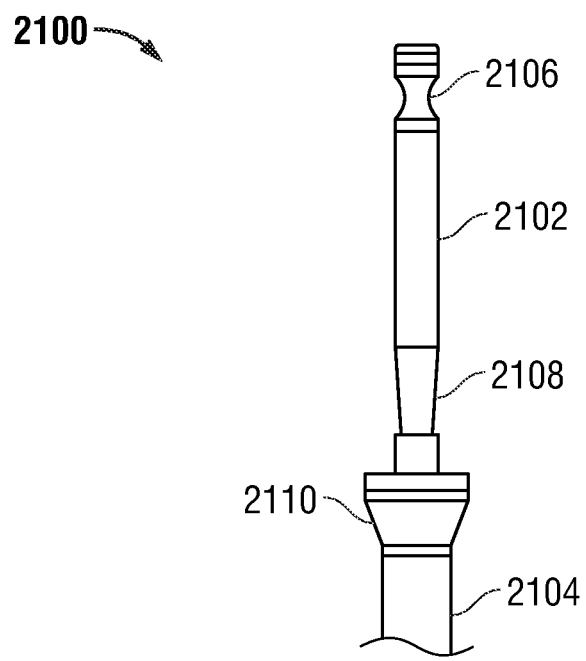

In other variations, the delivery device may comprise a shaft onto which the expandable device may be temporarily mounted. FIGS. 21A-21D illustrate one such variation of delivery device (2100) comprising shaft (2102) and sheath (2104). FIG. 21A shows a side view of shaft (2102). In some variations, the shaft (2102) may comprise one or more tapered segments. In the variation shown in FIG. 21A, shaft (2102) comprises a first to portion (2106) and a second tapered portion (2108). Shaft (2102) may comprise any number of tapered portions (e.g., zero, one, two, or three or more), and these tapered portions may be located at any point or points along the length of shaft (2102). In some of these variations, the tapered portions may be sized, shaped, and positioned to match the profile of one or more legs of a device. A tapered portion may be useful in helping to hold an expandable device on shaft (2102), as will be explained in more detail below. FIG. 21B shows a side view of shaft (2102) with sheath (2104) at least partially disposed over shaft (2104). While shown in FIG. 21B as having a flared end (2110), sheath (2104) need not have a flared end (2110).

To mount an expandable device (2112) onto delivery device (2100), the hub (2114) of expandable device (2112) may be placed on the distal tip of shaft (2104), as shown in FIG. 21C. In variations where the hub (2114) comprises one or more channels, slots, or passageways extending at least partially through the hub (2114), a portion of shaft (2102) may be configured to at least partially extend into one or more of the channels, slots, or passageways, but need not. Next, the legs (2116) of expandable device (2112) may be crimped to a low-profile configuration, as shown in FIG. 21D. In some variations, one or more portions of legs (2116) may be configured to fit at least partially within one or more tapered portions of the shaft (2102). For example, in the variation shown in FIG. 21D, each leg (2116) comprises a curved portion (2118) that may fit within the first tapered portion (2106) when the expandable device (2112) is crimped into a low-profile configuration. As long as the expandable device (2112) remains in a low-profile configuration, the engagement between curved portion (2118) and first tapered portion (2106) may prevent expandable device (2112) from moving off of shaft (2102). In other words, the legs (2116) may wrap around the distal end of shaft (2102) to prevent the expandable device (2112) from moving along the length of shaft (2102). Similarly, each leg (2116) may comprise a straight segment (2120) at the distal end thereof, which may engage the second tapered portion (2108) of shaft (2104).

To temporarily constrain the expandable device (2112) in a low-profile configuration, sheath (2104) may be advanced to cover at least a portion of one or more legs (2116), as shown in FIG. 21D. When sheath (2104) engages a portion of a leg (2116), it may prevent the leg (2116) from expanding or otherwise rotating away from shaft (2102). In this way, the expandable device (2112) may be "locked" onto delivery device (2100). Essentially, the engagement between sheath (2104) and legs (2116) may prevent the expandable device (2112) from expanding, while the engagement between legs (2116) and first (2106) and second (2108) tapered portions may prevent the expandable device (2112) from moving along the length of the shaft (2102). While shown in FIG. 21D as only covering the straight segments (2120) of legs (2116), sheath (2104) may cover any suitable portion or portions of legs (2116). In variations where the distal ends of the legs (2116) are substantially parallel to longitudinal axis of the shaft (2102), as shown in FIG. 21D, a thinner sheath (2104) may be used to cover the distal ends of the legs (2116).

To deliver the expandable device (2112), sheath (2104) may be retracted to release legs (2116). In variations where the device is self-expandable, the expandable device may self-expand and thereby release itself from shaft (2102). In some variations, one or more expandable structures (e.g., a balloon) may be expanded to expand the device and release it from the shaft (2102). In some of these variations, one or more balloons (not shown) may be attached to an outer surface of shaft (2102). When the balloon or balloons are inflated, they may push the legs (2116) apart, thereby expanding the device (2112) to an expanded configuration.

While shown in FIGS. 21A-D as having a sheath (2104), delivery device (2100) need not. Indeed, the expandable device (2112) may be held in a low-profile configure in any suitable manner. In some variations, one or more ties, sutures, or chords may be used to bind one or more legs (2116) in a low-profile configuration. In other variations, one or more adhesives or other materials may be used to temporarily bind legs (2116) to delivery device (2100). In some of these variations, a water-soluble polymer may be used to hold legs (2116) against shaft (2102). To release legs (2116), water may be applied (e.g., sprayed) on the legs (2116) to dissolve the polymer.

Methods

Both the self-expanding devices and delivery devices described here may be useful in a variety of locations within the body, for a number of different purposes. For example, the expandable devices may help provide support to, apply one or more forces to, and/or dilate tissue, or may be useful in treating various conditions or diseases. The expandable devices may indeed by used in any area of the body that may benefit from their structural and functional features.

For example, the devices may be delivered to one or more tonsils, nasal passages, sinus cavities, arteries, veins, one or more openings or cavities, e.g., the middle ear or tympanic cavity, hollow-body organs such as the ureters, fallopian tubes, biliary ducts; pulmonary organs such as tracheas, bronchi and bronchioles; and gastrointestinal organs such as the esophagus, stomach, intestines, and colon; and the like. In the case of nasal passages and sinus cavities, the devices may be delivered before, during, or after surgery. When placed in the nasal passage, the device may push against, move, or otherwise reconfigure one or more tissues (e.g., the middle turbinate, the inferior turbinate) in the nasal passage. For example, in some variations, a device may move or hold the middle turbinate away from the lateral nasal wall. Additionally, when placed in the sinuses or nasal passage, the device may act to hold, move, or otherwise reposition one or more polyps. This may in turn increase air flow through the nose and/or sinuses, which may be beneficial in treating one or more sinus conditions, such as those described immediately below.

The devices may further be used to treat and/or ameliorate one or more symptoms of a variety of diseases that include, but are not limited to, nasal polyposis, urinary incontinence, atherosclerosis, benign prostatic hypertrophy, recoiling lesions after percutaneous transluminal angioplasty and in dissections, chronic occlusions, anastamotic hyperplasia in vein grafts and synthetic vascular grafts, vulnerable plaque, aneurysms of the aorta and large arteries, arteriovenous fistulae and traumatic leaks, malignant stenosis of the gastrointestinal tract, acute ileus in colorectal cancer, biliary closure from cholangiocarcinoma or other hepatic cancers, benign compression of the trachea and malignant tracheobronchial obstructions, one or more diseases or conditions of the sinuses, and the like.

The devices may be delivered and deployed in any suitable manner. In some variations, the devices are deployed in an open surgical fashion. In other variations, the devices are deployed in a less invasive fashion (for example, laproscopically, endoscopically, or intravascularly through the use of catheters). In instances where the devices are delivered in a generally minimally invasive fashion, the devices may be delivered in their low-profile configurations. The devices may be preloaded in or on a delivery device, but need not be. For example, in instances where the device has a limited ability to fully expand after remaining in its compressed state for extended periods of time (i.e., relaxation of the device may occur over time, resulting in a loss of shape memory, for example), it may be more desirable to crimp and load the device into or onto a delivery device just prior to delivery and deployment. The device may be crimped straight into or onto a delivery device, as described in more detail above. Any suitable structure or device may be used to crimp the expandable devices described here, such as those devices described in U.S. Provisional Application Ser. No. 61/085,795, filed on Aug. 1, 2008 and entitled "Methods and Devices for Crimping Self-Expandable Devices," which is hereby incorporated in its entirety.

Any of the delivery devices described above may be used to deploy the expandable devices described here. Generally, at least a portion of a delivery device is introduced into the body. In some variations, the delivery device may be introduced into a natural opening in the body, such as an ear canal or a nostril. In other variations, the delivery device may be introduced into an artificially-created opening in the body. In some of these variations, the artificially-created opening may be pre-formed using one or more tools that are separate from the delivery device. In variations one or more portions of the delivery device may be used to create the opening. In still other variations, one or more portions of the expandable device may be used to create the opening.

Once the delivery device is introduced into the body, at least a portion of the delivery device may then be advanced to a target location. In some variations, this advancement occurs under direct visualization. The direct visualization may be achieved by a device external to the delivery device, such as an endoscope, or may be achieved by one or more visualization devices attached to the delivery device or disposed within one or more portions (i.e., a lumen of a cannula) of the delivery device. In other variations, the advancement occurs under indirect visualization, such as fluoroscopy, ultrasound, or computer image guidance.

Once the delivery device has reached the target location, the expandable device may be released from the delivery device. In variations where the device is self-expandable, the device may self-expand into an expanded configuration. In variations where the device is expandable in response to one or more forces or stimuli, one or more appropriate forces or stimuli may be applied to the device to expand the device into an expanded configuration. In some instances, expansion of the device may act to anchor the device against or into tissue.

When used to treat nasal polyposis or other polypoid adema one or more of the devices described here may be delivered into either a nasal passage or one or more sinus cavities. Once expanded, each leg of the device may either sit against one or more nasal polyps, puncture one or more nasal polyps, push between two or more nasal polyps to contact the base of one or more nasal polyps, or do a combination thereof. When the device is configured to deliver one or more drugs, it may be especially beneficial to deliver one or more drugs to the base of one or more of the nasal polyps. When one or more legs presses against one or more nasal polyps, the one or more legs may dilate or otherwise move the nasal polyps. This may, in turn, open one or more blocked nasal passageways or sinus ostia.

Although the foregoing invention has, for the purposes of clarity and understanding been described in some detail by way of illustration and example, it will be apparent that certain changes and modifications may be practiced, and are intended to fall within the scope of the appended claims.

I claim:

1. A method for treating nasal polyposis, comprising:
   providing an expandable device, the expandable device having a low profile configuration and an expanded configuration, and comprising:
      a plurality of legs connected to a hub; and
      a coating layer having one or more therapeutic agents;
   advancing the expandable device in the low-profile configuration to a nasal passageway or paranasal sinus cavity having one or more nasal polyps;
   deploying the expandable device, wherein deploying the expandable device allows the plurality of legs to extend into the expanded configuration and to contact at least one of the one or more nasal polyps; and
   releasing the one or more therapeutic agents from the coating layer of expandable device into the one or more nasal polyps and surrounding tissue of the nasal passageway or paranasal sinus cavity,
   wherein the plurality of legs of the expandable device applies a force of from about 0.5 Newtons to about 15 Newtons on the nasal polyps surrounding tissue.

2. The method of claim 1, wherein extension of the plurality of legs acts to hold or reposition the one or more nasal polyps.

3. The method of claim 1, wherein, once deployed, one or more of the plurality of legs sits against one or more nasal polyps, punctures one or more nasal polyps, pushes between two or more of the nasal polys, or a combination thereof.

4. The method of claim 1, wherein the expandable device further comprising one or more meshes between at least two legs of the plurality of legs configured to catch and move one or more nasal polyps.

5. The method of claim 1, wherein the hub is a domed hub at the proximal end formed from a biodegradable copolymer at a first composition ratio, and wherein each of the legs of the plurality of legs is formed from the biodegradable copolymer at a second composition ratio different from the first composition ratio.

6. The method of claim 5, wherein the expandable device is advanced using a delivery device comprising a shaft and a sheath and wherein deploying comprises retracting the sheath such that the expandable device expands into the expanded configuration.

7. The method of claim 6, wherein the shaft comprises a distal portion disposed within the domed hub when the expandable device is in the low-profile configuration.

8. The method of claim 6, wherein the plurality of legs are releasably mounted on the shaft by the sheath when the expandable device is in the low-profile configuration.

9. The method of claim 1, wherein the expandable device is self-expandable between the low-profile configuration and the expanded configuration.

10. The method of claim 1, wherein the coating layer comprises a poly(lactide-co-caprolactone) copolymer.

11. A method for treating nasal polyposis, comprising:
    providing an expandable device, the expandable device having a low profile configuration and an expanded configuration, and comprising:
       a plurality of legs connected to a hub; and
       a coating layer having one or more therapeutic agents;
    advancing the expandable device in the low-profile configuration to a nasal passageway or paranasal sinus cavity having one or more nasal polyps;
    deploying the expandable device, wherein deploying the expandable device allows the plurality of legs to extend into the expanded configuration and to contact at least one of the one or more nasal polyps; and
    releasing the one or more therapeutic agents from the coating layer of expandable device into the one or more nasal polyps and surrounding tissue of the nasal passageway or paranasal sinus cavity,
    wherein as the nasal polyps recede due to release of the one or more therapeutic agents, the plurality of legs continue to expand to maintain contact with the nasal polyps and surrounding tissue of the nasal passageway or paranasal sinus cavity.

12. The method of claim 11, wherein extension of the plurality of legs acts to hold or reposition the one or more nasal polyps.

13. The method of claim 11, wherein, once deployed, one or more of the plurality of legs sits against one or more nasal polyps, punctures one or more nasal polyps, pushes between two or more of the nasal polys, or a combination thereof.

14. The method of claim 11, wherein the expandable device further comprising one or more meshes between at least two legs of the plurality of legs configured to catch and move one or more nasal polyps.

15. The method of claim 11, wherein the hub is a domed hub at the proximal end formed from a biodegradable copolymer at a first composition ratio, and wherein each of the legs of the plurality of legs is formed from the biodegradable copolymer at a second composition ratio different from the first composition ratio.

16. The method of claim 11, wherein the expandable device is advanced using a delivery device comprising a shaft and a sheath and wherein deploying comprises retracting the sheath such that the expandable device expands into the expanded configuration.

17. The method of claim 16, wherein the shaft comprises a distal portion disposed within the domed hub when the expandable device is in the low-profile configuration.

18. The method of claim 16, wherein the plurality of legs are releasably mounted on the shaft by the sheath when the expandable device is in the low-profile configuration.

19. The method of claim 11, wherein the expandable device is self-expandable between the low-profile configuration and the expanded configuration.

20. The method of claim 11, wherein the coating layer comprises a poly(lactide-co-caprolactone) copolymer.

* * * * *